(12) United States Patent
Hawryluk et al.

(10) Patent No.: US 8,906,914 B2
(45) Date of Patent: Dec. 9, 2014

(54) ETHYLENE DIAMINE MODULATORS OF FATTY ACID HYDROLASE

(75) Inventors: Natalie A. Hawryluk, San Diego, CA (US); J. Guy Breitenbucher, Escondido, CA (US); William M. Jones, San Diego, CA (US); Alison L. Chambers, San Diego, CA (US); John M. Keith, San Diego, CA (US); Mark Seierstad, Escondido, CA (US)

(73) Assignee: Janssen Pharmaceutica NV (BE)

( * ) Notice: Subject to any disclaimer, the term of this patent is extended or adjusted under 35 U.S.C. 154(b) by 238 days.

(21) Appl. No.: 13/390,984

(22) PCT Filed: Aug. 17, 2010

(86) PCT No.: PCT/US2010/045683
§ 371 (c)(1),
(2), (4) Date: Feb. 17, 2012

(87) PCT Pub. No.: WO2011/022348
PCT Pub. Date: Feb. 24, 2011

(65) Prior Publication Data
US 2012/0149696 A1   Jun. 14, 2012

Related U.S. Application Data

(60) Provisional application No. 61/234,955, filed on Aug. 18, 2009.

(51) Int. Cl.
| | |
|---|---|
| C07D 239/42 | (2006.01) |
| C07D 403/12 | (2006.01) |
| A61K 31/506 | (2006.01) |
| C07D 417/12 | (2006.01) |
| C07D 413/04 | (2006.01) |
| C07D 409/12 | (2006.01) |
| C07D 409/04 | (2006.01) |
| C07D 401/04 | (2006.01) |
| C07D 413/12 | (2006.01) |
| C07D 405/12 | (2006.01) |
| C07D 405/04 | (2006.01) |

(52) U.S. Cl.
CPC ............ *C07D 239/42* (2013.01); *C07D 417/12* (2013.01); *C07D 413/04* (2013.01); *C07D 409/12* (2013.01); *C07D 409/04* (2013.01); *C07D 401/04* (2013.01); *C07D 403/12* (2013.01); *C07D 413/12* (2013.01); *C07D 405/12* (2013.01); *C07D 405/04* (2013.01)
USPC ........ 514/235.8; 514/256; 544/122; 544/326; 544/327; 544/328; 544/329

(58) Field of Classification Search
USPC ........................ 544/122, 326, 327, 328, 329; 514/235.8, 256
See application file for complete search history.

(56) References Cited

U.S. PATENT DOCUMENTS

| | | |
|---|---|---|
| 6,462,054 B1 | 10/2002 | Boger et al. |
| 6,881,740 B1 | 4/2005 | Jarrott et al. |
| 6,891,043 B2 | 5/2005 | Boger et al. |
| 2003/0187026 A1 | 10/2003 | Li et al. |
| 2005/0239785 A1 | 10/2005 | Boger et al. |
| 2006/0058525 A1 | 3/2006 | Singh et al. |
| 2006/0100212 A1 | 5/2006 | Boger et al. |
| 2006/0111359 A1 | 5/2006 | Boger et al. |
| 2006/0173184 A1 | 8/2006 | Apodaca et al. |
| 2007/0004741 A1 | 1/2007 | Apodaca et al. |
| 2007/0203156 A1 | 8/2007 | Boger et al. |
| 2009/0264429 A1 | 10/2009 | Apodaca et al. |

FOREIGN PATENT DOCUMENTS

| | | |
|---|---|---|
| WO | WO 02 87569 A1 | 11/2002 |
| WO | WO 2004 033652 A2 | 4/2004 |
| WO | WO 2006 044617 A1 | 4/2006 |
| WO | WO 2006 044732 A2 | 4/2006 |
| WO | WO 2007 061862 A2 | 5/2007 |
| WO | WO 2007 098142 A2 | 8/2007 |
| WO | WO 2007/140005 A2 | 12/2007 |
| WO | WO 2007 140005 A2 | 12/2007 |
| WO | WO 2009 047359 A1 | 4/2009 |

OTHER PUBLICATIONS

Simone, Oncology: Introduction, Cecil Textbook of Medicine, 20th Edition, vol. 1, pp. 1004-1010, 1996.*
Damasio, Alzheimer's Disease and Related Dementias, Cecil Textbook of Medicine, 20th Edition, vol. 2, pp. 1992-1996 (1996).*
Layzer, Degenerative Diseases of the Nervous System, Cecil Textbook of Medicine, 20th Edition, vol. 2, pp. 2050-2057 (1996).*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Bundgaard, Design of Prodrugs: Introduction, p. 1, 1985.*

(Continued)

*Primary Examiner* — Deepak Rao
(74) *Attorney, Agent, or Firm* — Mary A. Appollina

(57) ABSTRACT

Certain ethylene diamine compounds of Formula (I) are described, which are useful as FAAH inhibitors. Such compounds may be used in pharmaceutical compositions and methods for the treatment of disease states, disorders, and conditions mediated by fatty acid amide hydrolase (FAAH) activity, such as anxiety, pain, inflammation, sleep disorders, eating disorders, energy metabolism disorders, and movement disorders (e.g., multiple sclerosis). Methods of synthesizing such compounds are also disclosed.

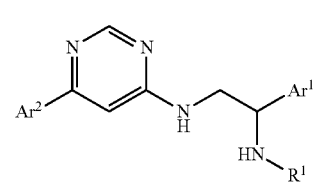

(I)

16 Claims, No Drawings

(56) References Cited

OTHER PUBLICATIONS

Silverman, Prodrugs and Drug Delivery Systems, The Organic Chemistry of Drug Design and Drug Action, pp. 352-400, 1992.*
Seierstad et al., Discovery and Development of Fatty Acid Amide Hydrolase (FAAH) Inhibitors, Journal of Medicinal Chemistry, vol. 51, No. 23, pp. 7327-7343, 2008.*
Pearce et al., Failure modes in anticancer drug discovery and development, Cancer Drug Design and Discovery Edited by Stephen Neidle, Chapter 18, pp. 424-435 (2008).*
Bagshawe et al "Antibody-Directed Enzyme Prodrug Therapy: A Review" Drug Dev Res 1995 vol. 34 pp. 220-230.
Baker et al "Endocannabinoids Control Spasticity in a Multiple Sclerosis Mode" FASEB J 2001 vol. 15(2) pp. 300-302.
Baker et al "Cannabinoids Contrac Spasticity and Tremor in a Multiple Sclerosis Model" Nature 2000 vol. 404 pp. 84-87.
Berge et al "Pharmaceutical Salts" J Pharm Sci 1977 vol. 66 pp. 1-19.
Bertolini et al "A New Rational Hypothesis for the Pharmacophore of the Active Metabolite of Leflunomide, A Potent Immunosuppressive Drug" J Med Chem 1997 vol. 40 pp. 2011-2016.
Bodor et al "Novel Approaches to the Design of Safer Drugs: Soft Drugs and Site-Specific Chemical Delivery Systems" Adv Drug Res 1984 vol. 13 pp. 224-331.
Boger et al "Exceptionally Potent Inhibitors of Fatty Acid Amide Hydrolase: The Enzyme Responsible for Degradation of Endgenous Oleamide and Anandamide" Proc Natl Acad Sci USA 2000 vol. 97(1) pp. 5044-5049.
Bouaboula et al "Anandamide Induced PPARγ Transcriptional Activation and 3T3-L1 Preadipocyte Differentiation" E J Pharmacol 2005 vol. 517 pp. 174-181.
Bundgaard et al Design of Prodrugs Ed. H. Bundgaard Elsevier 1985.
Cravatt et al "Molecular Characterization of an Enzyme That Degrades Neuromodulatory Fatty-Acid Amides" Nature 1996 vol. 384 pp. 83-87.
Cravatt et al "Supersensitivity to Anandamide and Enhanced Endogenous Cannabinoid Signaling in Mice Lacking Fatty Acide Amide Hydrolase" Proc Natl Acad Sci USA 2001 vol. 98(16) pp. 9371-9376.
Croxfsord et al "Cannabinoid-Mediated Neuroprotection, Not Immunosuppression, May Be More Relevant to Multiple Sclerosis" J Neuroimmunol 2008 vol. 183 pp. 120-129.
Fleisher et al "Improved Oral Drug Delivery: Solubility Limitations Overcome by the Use of Prodrugs" Adv Drug Delivery Rev 1996 vol. 19 pp. 115-130.
Gerber Lemaire et al "Synthesis of New Pyrrolidine Derivatives As Inhibitors of α-Mannosidse and of the Growth of Human Glioblastoma Cells" Heterocycles 2006 vol. 69 pp. 179-192.
Gobbi et al "Antidepressant-Like Activity and Modulation of Brain Monoaminergic Transmission by Blockade of Anandamie Hydrolysis" PNAS USA 2005 vol. 102(51) pp. 18620-18625.
Goya "Recent Advanced in Cannabionoid Receptor Agonsits and Antagonists" Expert Opin Ther Patents 2000 vol. 10 pp. 1529-1358.
Holt et al "Inhibitors of Fatty Acid Amide Hyrolase Reduce Carrageenan-Induced Hind Paw Inflammation in Pentobarbital-Treated Mice: Comparison With Indomethacin and Possible Involvement of Cannabinoid Receptors" Br J Pharmacol 2005 vol. 146 pp. 467-476.
Karsak et al "Cannabinoid Receptor Type 3 Gene Is Associated With Human Osteoporosis" Hum Mol Genet 2005 vol. 14 pp. 3389-3396.
Kathuria et al "Modulation of Anxiety Through Blockade of Anandamide Hydrolysis" Nat Med 2003 vol. 9(1) pp. 76-81.
Kirkham et al "Endocannabinoid Levels in Rat Limbic Forebrain and Hypothalamus in Relation to Fasting, Feeding, and Satiation: Stimulation of Eating by 2-Arachidonoyl Glycerol" Br J Pharmacol 2002 vol. 136 pp. 550-557.
Lambert et al "The Palmitoylethanolamide Family: A New Class of Anti-Inflammatory Agents?" Curr Med Chem 2002 vol. 9(6) pp. 663-674.
Larsen et al "Design and Application of Prodrugs" A Textbook of Drug Design and Development Krogsgaard-Larsen et al Eds Harwood Academic Publishers 1991.
Mendelson et al "The Hypnotic Actions of the Fatty Acid Amide, Oleamide" Neuropsychopharmacology 2001 vol. 25 pp. S36-S39.
Ofek et al "Peripheral Cannabinoid Receptor, CB2, Regulated Bone Mass" Proc Natl Acad Sci USA 2006 vol. 103 pp. 696-701.
Overton et al "GPR119, A Novel G Protein-Coupled Receptor Target for the Treatment of Type 2 Diabetes and Obesity" Br J Pharmacol 2008 vol. 153 pp. S76-S81.
Piomelli et al "The Molecular Logic of Endocannabinoid Signalling" Nat Rev Neurosci 2003 Voume 4(11) pp. 873-884.
Plutzky et al "Preventing Type 2 Diabetes and Cardiovascular Disease in Metabolic Syndrome: The Role of PPARα" Diab Vasc Dis Res 2007 vol. 4 (3) pp. S12-S14.
Robinson et al"Discovery of the Hemifumarate and (α-L-alanyloxy)Methyl Ether As Prodrugs of an Antirheumatic Oxindole: Prodrugs for the Enolic Oh Group"J Med Chem 1996 vol. 39 pp. 10-18.
Robson et al "Therapeutic Aspecs of Cannabis and Cannabinoids" Br J Psychiatry 2001 vol. 178 pp. 107-115.
Rodriguez De Fonesca et al "An Anorexic Lipid Mediator Regulated by Feeding" Nature 2001 vol. 414 pp. 209-212.
Devane et al "Isolation and Structure of a Brain Constituent That Binds to the Cannabinoid Receptor" Science 1992 vol. 258 pp. 1946-1949.
Cravatt et al "Chemical Characterization of a Family of Brain Lipids That Induce Sleep" Science 1995 vol. 268 pp. 1506-1509.
Shan et al "Prodrug Strategies Based on Intramolecular Cyclization Reactions" J Pharm Sci 1997 vol. 86(7) pp. 765-767.
Steffens et al "Low Dose Oral Cannabinoid Therapy Reduces Progression of Atherosclerosis in Mice" Nature 2005 vol. 434 pp. 782-786.
Svendsen et al "Does the Cannabinoid Dronabinol Reduce Central Pain in Multiple Sclerosis? Randomised Double Blind Placebo Controlled Crossover Trial" Br Med J 2004 vol. 329 pp. 253-260.
Stahl et al Handbook of Pharmaceutical Salts Properties Selection and Use Stahl and Wermuth Eds Wiley-VCH and VHCA Zurich 2002.
Ueda et al"Purificaction and Characterization of an Acid Amidase Selective for N-Palmitoylethanolamine, A Putative Endogenous Anti-Inflammatory Substance" J Biol Chem 2001 vol. 276(38) pp. 35552-35557.
Varvel et al "Fatty Acide Hydrolase(-/-) Mice Exhibit an Increased Sensitivity to the Disruptive Effects of Anandamide or Oleamide in a Working Memory Water Maze Task" J Pharmacol Exp Ther 2006 vol. 317(1) pp. 251-257.
Webb et al "Genetic Deletion of Fatty Acid Amide Hydrolase Results in Improved Long-Term Outcome in Chronic Autoimmune Encephalitis" Neurosci Lett 2008 vol. 439 pp. 106-110.

* cited by examiner

ETHYLENE DIAMINE MODULATORS OF FATTY ACID HYDROLASE

CROSS-REFERENCE TO RELATED APPLICATIONS

This application is a national phase of International Application No. PCT/US2010/045683 filed Aug. 17, 2010 and claims benefit of priority under 35 U.S.C. §119(e) of U.S. Provisional Application No. 61/234,955 filed on Aug. 18, 2009.

FIELD OF THE INVENTION

Certain ethylene diamine compounds, pharmaceutical compositions containing them, and methods of using them for the treatment of disease states, disorders, and conditions mediated by fatty acid amide hydrolase (FAAH) activity are provided.

BACKGROUND OF THE INVENTION

Medicinal benefits have been attributed to the cannabis plant for centuries. The primary bioactive constituent of cannabis is $\Delta^9$-tetrahydro-cannabinol (THC). The discovery of THC eventually led to the identification of two endogenous cannabinoid receptors responsible for its pharmacological actions, namely $CB_1$ and $CB_2$ (Goya, *Exp. Opin. Ther. Patents* 2000, 10, 1529). These discoveries not only established the site of action of THC, but also inspired inquiries into the endogenous agonists of these receptors, or "endocannabinoids". The first endocannabinoid identified was the fatty acid amide anandamide (AEA). AEA itself elicits many of the pharmacological effects of exogenous cannabinoids (Piomelli, *Nat. Rev. Neurosci.* 2003, 4(11), 873).

The catabolism of AEA is primarily attributable to the integral membrane bound protein fatty acid amide hydrolase (FAAH), which hydrolyzes AEA to arachidonic acid. FAAH was characterized in 1996 by Cravatt and co-workers (Cravatt, *Nature* 1996, 384, 83). It was subsequently determined that FAAH is additionally responsible for the catabolism of a large number of important lipid signaling fatty acid amides including: another major endocannabinoid, 2-arachidonoylglycerol (2-AG) (*Science* 1992, 258, 1946-1949); the sleep-inducing substance, oleamide (OEA) (*Science* 1995, 268, 1506); the appetite-suppressing agent, N-oleoylethanolamine (Rodriguez de Fonesca, *Nature* 2001, 414, 209); and the anti-inflammatory agent, palmitoylethanolamide (PEA) (Lambert, *Curr. Med. Chem.* 2002, 9(6), 663).

Small-molecule inhibitors of FAAH should elevate the concentrations of these endogenous signaling lipids and thereby produce their associated beneficial pharmacological effects. There have been some reports of the effects of various FAAH inhibitors in pre-clinical models.

In particular, two carbamate-based inhibitors of FAAH were reported to have analgesic properties in animal models. In rats, BMS-1 (see WO 02/087569), which has the structure shown below, was reported to have an analgesic effect in the Chung spinal nerve ligation model of neuropathic pain, and the Hargraves test of acute thermal nociception. URB-597 was reported to have efficacy in the zero plus maze model of anxiety in rats, as well as analgesic efficacy in the rat hot plate and formalin tests (Kathuria, *Nat. Med.* 2003, 9(1), 76). The sulfonylfluoride AM374 was also shown to significantly reduce spasticity in chronic relapsing experimental autoimmune encephalomyelitis (CREAE) mice, an animal model of multiple sclerosis (Baker, *FASEB J.* 2001, 15(2), 300).

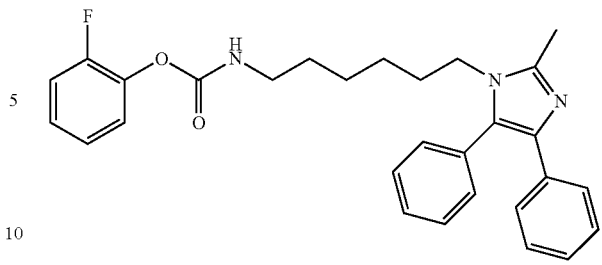

BMS-1

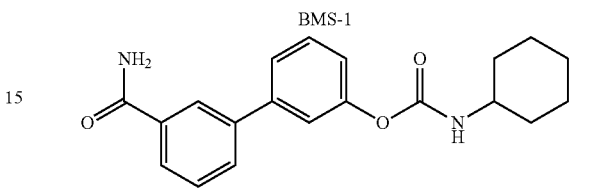

URB-597

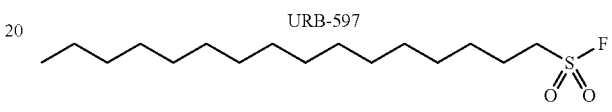

AM-374

In addition, the oxazolopyridine ketone OL-135 is reported to be a potent inhibitor of FAAH, and has been reported to have analgesic activity in both the hot plate and tail emersion tests of thermal nociception in rats (WO 04/033652).

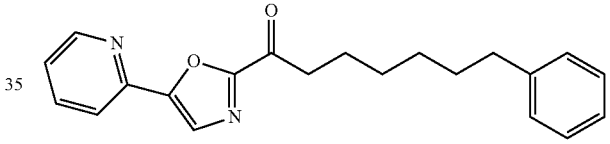

OL-135

Results of research on the effects of certain exogenous cannabinoids has elucidated that a FAAH inhibitor may be useful for treating various conditions, diseases, disorders, or symptoms. These include pain, nausea/emesis, anorexia, spasticity, movement disorders, epilepsy and glaucoma. To date, approved therapeutic uses for cannabinoids include the relief of chemotherapy-induced nausea and emesis among patients with cancer and appetite enhancement in patients with HIV/AIDs who experience anorexia as a result of wasting syndrome. Two products are commercially available in some countries for these indications, namely, dronabinol (Marinol®) and nabilone.

Apart from the approved indications, a therapeutic field that has received much attention for cannabinoid use is analgesia, i.e., the treatment of pain. Five small randomized controlled trials showed that THC is superior to placebo, producing dose-related analgesia (Robson, *Br. J. Psychiatry* 2001, 178, 107-115). Atlantic Pharmaceuticals is reported to be developing a synthetic cannabinoid, CT-3, a 1,1-dimethyl heptyl derivative of the carboxylic metabolite of tetrahydrocannabinol, as an orally active analgesic and anti-inflammatory agent. A pilot phase II trial in chronic neuropathic pain with CT-3 was reportedly initiated in Germany in May 2002.

A number of individuals with locomotor activity-related diseases, such as multiple sclerosis have claimed a benefit from cannabis for both disease-related pain and spasticity, with support from small controlled trials (Croxford et el., *J.*

*Neuroimmunol*, 2008, 193, 120-9; Svendsen, *Br. Med. J.* 2004, 329, 253). Likewise, various victims of spinal cord injuries, such as paraplegia, have reported that their painful spasms are alleviated after smoking marijuana. A report showing that cannabinoids appear to control spasticity and tremor in the CREAE model of multiple sclerosis demonstrated that these effects are mediated by $CB_1$ and $CB_2$ receptors (Baker, *Nature* 2000, 404, 84-87). Phase 3 clinical trials have been undertaken in multiple sclerosis and spinal cord injury patients with a narrow ratio mixture of tetrahydrocannabinol/cannabidiol (THC/CBD). It has been reported that FAAH knockout mice consistently recover to a better clinical score than wild type controls, and this improvement is not a result of anti-inflammatory activity, but rather may reflect some neuroprotection or remyelination promoting effect of lack of the enzyme (Webb et al, *Neurosci Lett.,* 2008, vol. 439, 106-110).

Reports of small-scale controlled trials to investigate other potential commercial uses of cannabinoids have been made. Trials in volunteers have been reported to have confirmed that oral, injected, and smoked cannabinoids produced dose-related reductions in intraocular pressure (IOP) and therefore may relieve glaucoma symptoms. Ophthalmologists have prescribed cannabis for patients with glaucoma in whom other drugs have failed to adequately control intraocular pressure (Robson, 2001, supra).

Inhibition of FAAH using a small-molecule inhibitor may be advantageous compared to treatment with a direct-acting $CB_1$ agonist. Administration of exogenous $CB_1$ agonists may produce a range of responses, including reduced nociception, catalepsy, hypothermia, and increased feeding behavior. These four in particular are termed the "cannabinoid tetrad." Experiments with FAAH –/– mice show reduced responses in tests of nociception, but did not show catalepsy, hypothermia, or increased feeding behavior (Cravatt, *Proc. Natl. Acad. Sci. USA* 2001, 98(16), 9371). Fasting caused levels of AEA to increase in rat limbic forebrain, but not in other brain areas, providing evidence that stimulation of AEA biosynthesis may be anatomically regionalized to targeted CNS pathways (Kirkham, *Br. J. Pharmacol.* 2002, 136, 550). The finding that AEA increases are localized within the brain, rather than systemic, suggests that FAAH inhibition with a small molecule could enhance the actions of AEA and other fatty acid amides in tissue regions where synthesis and release of these signaling molecules is occurring in a given pathophysiological condition (Piomelli, 2003, supra).

In addition to the effects of a FAAH inhibitor on AEA and other endocannabinoids, inhibitors of FAAH's catabolism of other lipid mediators may be used in treating certain other therapeutic indications. For example, PEA has demonstrated biological effects in animal models of inflammation (Holt, et al. *Br. J. Pharmacol.* 2005, 146, 467-476), immunosuppression, analgesia, and neuroprotection (Ueda, *J. Biol. Chem.* 2001, 276(38), 35552). Oleamide, another substrate of FAAH, induces sleep (Boger, *Proc. Natl. Acad. Sci. USA* 2000, 97(10), 5044; Mendelson, *Neuropsychopharmacology* 2001, 25, S36). Inhibition of FAAH has also been implicated in cognition (Varvel et al., *J. Pharmacol. Exp. Ther.* 2006, 317(1), 251-257) and depression (Gobbi et al., *PNAS, USA* 2005, 102(51), 18620-18625).

Two additional indications for FAAH are supported by recent data indicating that FAAH substrate activated receptors are important in energy metabolism, and in bone homeostasis (Overton et al., *Br. J. Pharmacol.* 2008, in press; and Plutzky, *Diab. Vasc. Dis. Res.* 2007, 4 *Suppl* 3, S12-4). It has been shown that the previously mentioned lipid signaling fatty acid amides catabolized by FAAH, oleoylethanolamide (OEA), is one of the most active agonists of the recently de-orphanised GPCR 119 (GPR119) (also termed glucose dependent insulinotropic receptor). This receptor is expressed predominantly in the pancreas in humans and activation improves glucose homeostasis via glucose-dependent insulin release in pancreatic beta-cells. GPR119 agonists can suppress glucose excursions when administered during oral glucose tolerance tests, and OEA has also been shown independently to regulate food intake and body weight gain when administered to rodents, indicating a probable benefit energy metabolism disorders, such as insulin resistance and diabetes. The FAAH substrate palmitoylethanolamide (PEA) is an agonist at the PPARα receptor. Evidence from surrogate markers in human studies with the PPARα agonist fenofibrate is supportive of the concept that PPARα agonism offers the potential for inducing a coordinated PPARα response that may improve dyslipidaemia, repress inflammation and limit atherosclerosis in patients with the metabolic syndrome or type 2 diabetes. The FAAH substrate anandamide (AEA) is an agonist at the PPARγ receptor. Anandamide treatment induces 3T3-L1 differentiation into adipocytes, as well as triglyceride droplet accumulation and expression of adiponectin (Bouaboula et al., *E. J. Pharmacol.* 2005, 517, 174-181). Low dose cannabinoid therapy has been shown to reduce atherosclerosis in mice, further suggesting a therapeutic benefit of FAAH inhibition in dyslipidemia, liver steatosis, steatohepatitis, obesity, and metabolic syndrome (Steffens et al., *Nature,* 2005, 434, 782-6).

Osteoporosis is one of the most common degenerative diseases. It is characterized by reduced bone mineral density (BMD) with an increased risk for bone fractures. $CB_2$-deficient mice have a markedly accelerated age-related trabecular bone loss and cortical expansion. A $CB_2$-selective agonism enhances endocortical osteoblast number and activity and restrains trabecular osteoclastogenesis and attenuates ovariectomy-induced bone loss (Ofek et al., *Proc. Natl. Acad. Sci. U.S.A.* 2006, 103, 696-701). There is a substantial genetic contribution to BMD, although the genetic factors involved in the pathogenesis of human osteoporosis are largely unknown. The applicability to human BMD is suggested by genetic studies in which a significant association of single polymorphisms and haplotypes was found encompassing the CNR2 gene on human chromosome 1p36, demonstrating a role for the peripherally expressed $CB_2$ receptor in the etiology of osteoporosis (Karsak et al., *Hum. Mol. Genet,* 2005, 14, 3389-96). Research also demonstrates a role in osteoarthritis.

Thus, small-molecule FAAH inhibitors should be useful in treating pain of various etiologies, anxiety, multiple sclerosis, Parkinson's disease and other movement disorders, nausea/emesis, eating disorders, epilepsy, glaucoma, inflammation, itch, immunosuppression, neuroprotection, depression, cognition enhancement, sleep disorders, dyslipidemia, liver steatosis, steatohepatitis, obesity, metabolic syndrome, osteoporosis, and other diseases/disorders referenced above, and potentially with fewer side effects than treatment with an exogenous cannabinoid.

Certain amino-substituted pyrimidine compounds have been described in the literature. Certain 2,6-substituted-4-monosubstituted pyrimidines were disclosed as prostaglandin D2 receptor antagonists (PCT Pat. Appl. Publ. No. WO 2006/044732). Certain 2,4-Pyrimidinediamine compounds appear in U.S. Pat. Appl. Publ. No. US 2006/0058525. U.S. Pat. Appl. Publ. No. US 2003/0187026 describes certain heterocyclic compounds as kinase inhibitors. Certain arylalkyl heterocyclic compounds are shown as pharmaceutical agents in U.S. Pat. No. 6,881,740. Certain piperazinyl and piperidinyl ureas, heteroaryl piperazinyl ureas, and heteroaryl-substituted ureas were disclosed as inhibitors of FAAH in U.S. Pat. Appl. Publ. No. US 2006/0173184, U.S. Pat. Appl. Publ. No. US 2007/0004741, respectively. Certain α-keto-oxazole and oxazolyl piperidine compounds were disclosed as inhibitors of FAAH In PCT Pat. Appl. Publ. No. WO 2007/061862 and WO 2007/140005, respectively. Certain α-keto heterocyclic compounds were disclosed as inhibitors of FAAH in U.S. Pat. Nos. 6,462,054 and 6,891,043, U.S. Pat. Appl. Publ. Nos. US 2005/0239785 and US 2006/0111359, and PCT Pat. Appl. Publ. No. WO 2004/033652. Certain oxadiazole ketone compounds were disclosed as inhibitors of FAAH in U.S. Pat. Appl. Publ. No. US 2006/0100212, and PCT Pat. Appl. Publ. No. WO 2006/044617. Certain oxazole ketone compounds were disclosed as inhibitors of FAAH in U.S. Pat. Appl. Publ. No. US 2007/0203156, and PCT Pat. Appl. Publ. No. WO 2007/098142. Certain aryl-hydroxyethylamino-pyrimidine and triazine FAAH modulators are disclosed in U.S. patent Ser. No. 12/378,734. Certain heterocycles as inhibitors of cyclin-dependent kinases are disclosed in PCT Pat. Appl. Publ. No. WO 2009/047359.

Despite the progress that has been achieved, there remains a desire for potent FAAH modulators with suitable pharmaceutical properties.

SUMMARY OF THE INVENTION

Certain ethylene diamine derivatives are herein described, which have been found to have FAAH-modulating activity. The invention is directed to the general and preferred embodiments defined, respectively, by the independent and dependent claims appended hereto, which are incorporated by reference herein.

In one general aspect, the invention is directed to compounds of Formula (I):

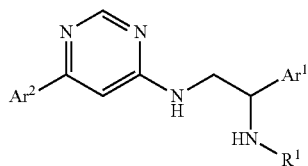

wherein
$R^1$ is —H, —C(O)CF$_3$, or —CO$_2$C(CH$_3$)$_3$;
Ar$^1$ is phenyl, napthyl, a 5 or 6 membered monocyclic heteroaryl group with carbon at the point of attachment, or a 9 or 10 membered bicyclic heteroaryl group with carbon at the point of attachment, each unsubstituted or substituted with;
(i) one, two, or three R$^c$ moieties,
where each R$^c$ moiety is independently —C$_{1-4}$alkyl, —C$_{1-4}$alkyl-OH, —C$_{1-4}$alkyl-CN, —OH, —OC$_{1-4}$ alkyl, perfluoroalkyl, perfluoroalkoxy, —S(O)$_{0-2}$C$_{1-4}$ alkyl, —SCF$_3$, —SO$_2$CF$_3$, —CHO, —CO$_2$C$_{1-4}$alkyl, —CO$_2$C$_{1-4}$alkyl, —CO$_2$H, —N(R$^d$)R$^e$, —SO$_2$NR$^d$R$^e$, —NR$^d$SO$_2$R$^e$, —C(O)NR$^d$R$^e$, —NO$_2$, —CN, imidazolyl, phenyl, pyridyl, pyrrolidinyl, thiophenyl, or halo,
where R$^d$ and R$^e$ are each independently H or —C$_{1-4}$ alkyl, or taken together R$^d$ and R$^e$ with the nitrogen of attachment form a 4-7 membered heterocycloalkyl ring; or
(ii) two or three R$^c$ moieties where two R$^c$ moieties are adjacent to each other and together form —O(CH$_2$)$_{1-3}$ O— unsubstituted or substituted with one or two fluoro groups, and the third R$^c$ moiety, when present, is —C$_{1-4}$ alkyl, —C$_{1-4}$alkyl-OH, —C$_{1-4}$alkyl-CN, perfluoroalkyl, —OH, —OC$_{1-4}$alkyl, perfluoroalkoxy, —S(O)$_{0-2}$C$_{1-4}$ alkyl, —SCF$_3$, —SO$_2$CF$_3$, —CHO, —COC$_{1-4}$alkyl, —CO$_2$C$_{1-4}$alkyl, —CO$_2$H, —N(R$^d$)R$^e$, —SO$_2$NR$^d$R$^e$, —NR$^d$SO$_2$R$^e$, —C(O)NR$^d$R$^e$, —NO$_2$, —CN, or halo,
where R$^d$ and R$^e$ are each independently —H or —C$_{1-4}$ alkyl;
Ar$^2$ is:
(i) phenyl substituted with;
one, two, or three R$^g$ moieties each at a meta or para position, and optionally with one or two additional R$^g$ moieties at an ortho position;
where each R$^g$ moiety is independently halo, OH, —C$_{1-4}$ alkyl, —C$_{1-4}$alkyl-OH, —C$_{1-4}$alkyl-CN, perfluoroalkyl, perfluoroalkoxy, —OC$_{1-4}$alkyl, —OC$_{1-4}$alkyl-(monocyclic cycloalkyl), —S(O)$_{0-2}$C$_{1-4}$alkyl, —SCF$_3$, —SO$_2$CF$_3$, —CHO, —COC$_{1-4}$alkyl, —CO$_2$C$_{1-4}$alkyl, —CO$_2$H, —N(R$^h$)R$^i$, —SO$_2$NR$^j$R$^k$, —NR$^h$SO$_2$R$^i$, —C(O)NR$^j$R$^k$, —NO$_2$, —CN; or a phenoxy, benzyl, phenethyl, or benzoyl group unsubstituted or substituted with —C$_{1-4}$alkyl, —OC$_{1-4}$alkyl, perfluoroalkyl, perfluoroalkoxy, —NO$_2$, —CN, or halo; or two adjacent R$^g$ moieties taken together form —O(CH$_2$)$_{1-2}$O— unsubstituted or substituted with one or two fluoro groups;
where R$^h$ is H or —C$_{1-4}$alkyl;
R$^i$ is —C$_{1-4}$alkyl or monocyclic cycloalkyl group;
or R$^h$ and R$^i$ taken together with the atoms to which they are attached form a monocyclic heterocycloalkyl ring;
R$^j$ is H or —C$_{1-4}$alkyl; and
R$^k$ is H, —C$_{1-4}$alkyl or monocyclic cycloalkyl group;
or R$^j$ and R$^k$ taken together with the atoms to which they are attached form a monocyclic heterocycloalkyl ring; or
(ii) a monocyclic heteroaryl group substituted with one, two, or three R$^g$ moieties; or
(iii) a naphthyl or bicyclic heteroaryl group unsubstituted or substituted with one, two, or three R$^l$ moieties;
where each R$^l$ moiety is independently —C$_{1-4}$alkyl, perfluoroalkyl, perfluoroalkoxy, —NO$_2$, —CN, or halo.

The invention also relates to pharmaceutically acceptable salts of compounds of Formula (I), pharmaceutically acceptable prodrugs of compounds of Formula (I), and pharmaceutically acceptable metabolites of compounds of Formula (I). In certain preferred embodiments, the compound of Formula (I) is a compound selected from those species described or exemplified in the detailed description below.

In a further general aspect, the invention relates to pharmaceutical compositions each comprising: (a) a therapeutically effective amount of at least one chemical entity selected from compounds of Formula (I), pharmaceutically acceptable salts of compounds of Formula (I), pharmaceutically acceptable prodrugs of compounds of Formula (I), and pharmaceutically acceptable metabolites of compounds of Formula (I); and (b) a pharmaceutically acceptable excipient.

In another aspect, embodiments of the invention are useful as FAAH modulators. Thus, the invention is directed to a method for modulating FAAH activity, comprising exposing FAAH to a therapeutically effective amount of at least one chemical entity selected from compounds of Formula (I), pharmaceutically acceptable salts of compounds of Formula (I), pharmaceutically acceptable prodrugs of compounds of Formula (I), and pharmaceutically active metabolites of compounds of Formula (I).

In another general aspect, the invention is directed to a method of treating a subject suffering from or diagnosed with a disease, disorder, or medical condition mediated by FAAH activity, comprising administering to the subject in need of such treatment an effective amount of at least one agent selected from compounds of Formula (I) and their pharmaceutically acceptable salts, pharmaceutically active prodrugs, and pharmaceutically active metabolites. In preferred embodiments of the inventive method, the disease, disorder, or medical condition is selected from: anxiety, depression, pain, sleep disorders, eating disorders, inflammation, multiple sclerosis and other movement disorders, HIV wasting syndrome, closed head injury, stroke, learning and memory disorders, Alzheimer's disease, epilepsy, Tourette's syndrome, Niemann-Pick disease, Parkinson's disease, Huntington's chorea, optic neuritis, autoimmune uveitis, symptoms of drug or alcohol withdrawal, nausea, emesis, sexual dysfunction, anxiety, post-traumatic stress disorder, cerebral vasospasm, glaucoma, irritable bowel syndrome, inflammatory bowel disease, immunosuppression, itch, gastroesophageal reflux disease, paralytic ileus, secretory diarrhea, gastric ulcer, rheumatoid arthritis, unwanted pregnancy, hypertension, cancer, hepatitis, allergic airway disease, autoimmune diabetes, intractable pruritis, neuroinflammation, diabetes, metabolic syndrome, osteoporosis, dyslipidemia, liver steatosis, and steatohepatitis.

Additional embodiments, features, and advantages of the invention will be apparent from the following detailed description and through practice of the invention.

DETAILED DESCRIPTION OF INVENTION AND ITS PREFERRED EMBODIMENTS

The invention may be more fully appreciated by reference to the following detailed description, including the following glossary of terms and the concluding examples. For the sake of brevity, the disclosures of the publications, including patents, cited in this specification are herein incorporated by reference.

As used herein, the terms "including", "containing" and "comprising" are used in their open, non-limiting sense.

The term "alkyl" refers to a straight- or branched-chain alkyl group having from 1 to 12 carbon atoms in the chain. Examples of alkyl groups include methyl (Me, which also may be structurally depicted by/symbol), ethyl (Et), n-propyl, isopropyl, butyl, isobutyl, sec-butyl, tert-butyl (tBu), pentyl, isopentyl, tert-pentyl, hexyl, isohexyl, and so on.

The term "cycloalkyl" refers to a saturated or partially saturated, monocyclic, fused polycyclic, or spiro polycyclic carbocycle having from 3 to 12 ring atoms per carbocycle. Illustrative examples of cycloalkyl groups include the following entities, in the form of properly bonded moieties:

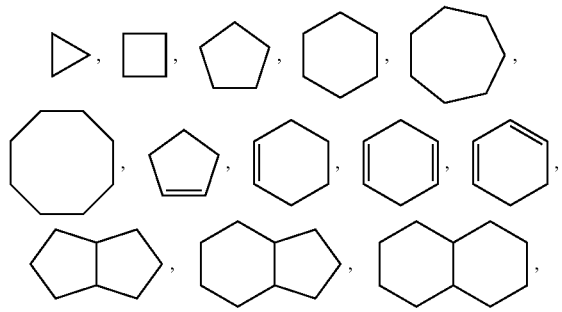

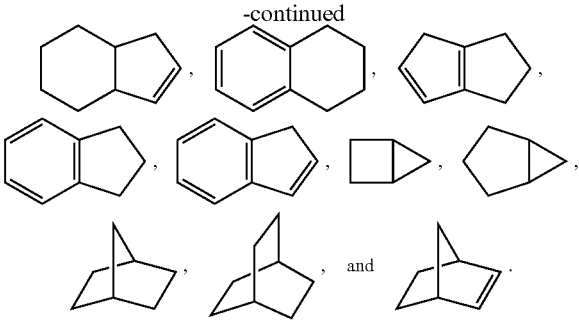

A "heterocycloalkyl" refers to a monocyclic, or fused, bridged, or spiro polycyclic ring structure that is saturated or partially saturated and has from 3 to 12 ring atoms per ring structure selected from carbon atoms and one, two, or three heteroatoms independently selected from nitrogen, oxygen, and sulfur. The ring structure may optionally contain up to two oxo groups on carbon or sulfur ring members. Illustrative examples of heterocycloalkyl groups include the following entities, in the form of properly bonded moieties:

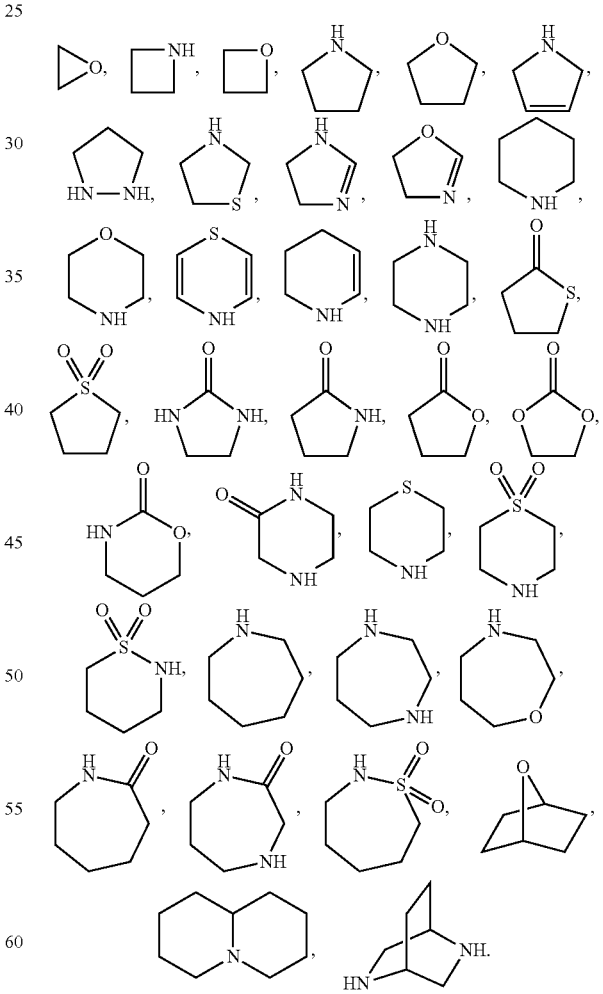

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

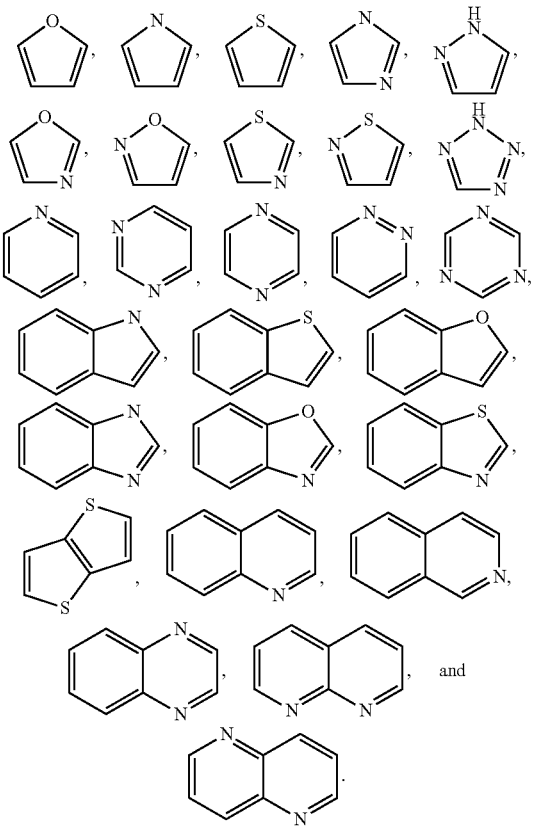

The term "halogen" represents chlorine, fluorine, bromine or iodine. The term "halo" represents chloro, fluoro, bromo or iodo.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

The terms "para", "meta", and "ortho" have the meanings as understood in the art. Thus, for example, a fully substituted phenyl group has substituents at both "ortho" (o) positions adjacent to the point of attachment of the phenyl ring, both "meta" (m) positions, and the one "para" (p) position across from the point of attachment as illustrated below.

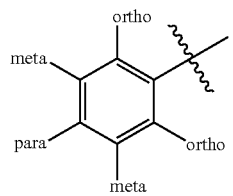

In one general embodiment, the invention relates to compounds that are encompassed by Formula (I) and pharmaceutically acceptable salts, pharmaceutically acceptable prodrugs, and pharmaceutically active metabolites of such compounds. In another general embodiment, the invention relates to pharmaceutical compositions each comprising a therapeutically effective amount of a FAAH-modulating agent selected from compounds of Formula (I) and pharmaceutically acceptable salts, pharmaceutically acceptable prodrugs, and pharmaceutically active metabolites of such compounds. Compounds encompassed by Formula (I) having asymmetric or chiral centers may exist in different enantiomeric forms. All stereoisomers of the compounds of the general formula and racemates or mixtures of various combinations thereof, are intended to be represented by the formula. Thus, except where a stereocenter is shown as having a specific stereoisomeric form, a general formula shown herein is intended to represent all racemates, enantiomerically pure forms, diastereomeric forms, atropisomeric forms, and mixtures thereof. Furthermore, certain structures may exist as geometric isomers (i.e., cis and trans isomers), as tautomers, or as atropisomers, which are intended to be encompassed by a structural formula. Additionally, a formula given herein is intended to embrace hydrates, solvates, and polymorphs of such compounds, and mixtures thereof.

The term "perfluoroalkyl" refers to a straight- or branched-chain alkyl group having from 1 to 4 carbon atoms in the chain optionally substituting hydrogens with fluorines. Examples of perfluoroalkyl groups include trifluoromethyl ($CF_3$), difluoromethyl ($CF_2H$), monofluoromethyl ($CH_2F$), pentafluoroethyl ($CF_2CF_3$), tetrafluoroethyl ($CHFCF_3$), trifluoroethyl ($CH_2CF_3$), tetrafluorotrifluoromethylethyl ($—CF(CF_3)_2$), and groups that in light of the ordinary skill in the art and the teachings provided herein would be considered equivalent to any one of the foregoing examples.

The term "perfluoroalkoxy" refers to a straight- or branched-chain alkoxy group having from 1 to 4 carbon atoms in the chain optionally substituting hydrogens with fluorines. Examples of perfluoroalkoxy groups include trifluoromethoxy ($OCF_3$), difluoromethoxy ($OCF_2H$), monofluoromethoxy ($OCH_2F$), pentafluoroethoxy ($OCF_2CF_3$), tetrafluoroethoxy ($OCHFCF_3$), trifluoroethoxy ($OCH_2CF_3$), tetrafluorotrifluoromethylethoxy ($—OCF(CF_3)_2$), and groups that in light of the ordinary skill in the art and the teachings provided herein would be considered equivalent to any one of the foregoing examples.

A structural formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{15}N$, $^{18}O$, $^{17}O$, $^{32}P$, $^{33}P$, $^{35}S$, $^{18}F$, $^{36}Cl$, and $^{125}I$, respectively. Such isotopically labeled compounds are useful in metabolic studies (preferably with $^{14}C$), reaction kinetic studies (with, for example $^{2}H$ or $^{3}H$), detection or imaging techniques [such as positron emission tomography (PET) or single-photon emission computed tomography (SPECT)], including drug or substrate tissue distribution assays, or in radioactive treatment of patients. In particular, an $^{18}F$- or $^{11}C$-labeled compound may be preferred for PET or SPECT studies. Further, substitution with heavier isotopes such as deuterium (i.e., $^{2}H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the moiety for the variable appearing elsewhere. In other words, where a formula variable appears more than once, the choice of the species from a specified list is independent of the choice of the species for the same variable elsewhere in the formula.

In certain embodiments of Formula (I), $R^1$ is —H, —C(O)CF$_3$, or —CO$_2$C(CH$_3$)$_3$.

In certain embodiments of Formula (I), $Ar^1$ is phenyl, napthyl, a 5 or 6 membered monocyclic heteroaryl group with carbon at the point of attachment, or a 9 or 10 membered bicyclic heteroaryl group with carbon at the point of attachment, each unsubstituted or substituted with one, two, or three $R^c$ moieties. In certain embodiments, each $R^c$ moiety is independently —C$_{1-4}$alkyl, —C$_{1-4}$alkyl-OH, —C$_{1-4}$alkyl-CN, —CF$_3$, —OH, —OC$_{1-4}$alkyl, —OCF$_3$, —OCHF$_2$, —OCH$_2$CF$_3$, —S(O)$_{0-2}$C$_{1-4}$alkyl, —SCF$_3$, —SO$_2$CF$_3$, —CHO, —COC$_{1-4}$alkyl, —CO$_2$C$_{1-4}$alkyl, —CO$_2$H, —N(R$^d$)R$^e$, —SO$_2$NR$^d$R$^e$, —NR$^d$SO$_2$R$^e$, —C(O)NR$^d$R$^e$, —NO$_2$, —CN, phenyl, pyridyl, or halo where $R^d$ and $R^e$ are each independently H or —C$_{1-4}$alkyl, or taken together $R^d$ and $R^e$ with the nitrogen of attachment form a 4-7 membered heterocycloalkyl ring. In certain embodiments, each $R^c$ substituent is selected from halo, —CF$_3$, —CN, —SCH$_3$, —SCF$_3$, —S(O)(O)CH$_3$, or two adjacent substituents together form —OCF$_2$O—. In further embodiments, two $R^c$ moieties are adjacent to each other and together form —O(CH$_2$)$_{1-3}$O— unsubstituted or substituted with one or two fluoro groups, and an optional third $R^c$ moiety, when present, is —C$_{1-4}$alkyl, —C$_{1-4}$alkyl-OH, —C$_{1-4}$alkyl-CN, —CF$_3$, —OH, —OC$_{1-4}$alkyl, —OCF$_3$, —OCHF$_2$, —OCH$_2$CF$_3$, —S(O)$_{0-2}$C$_{1-4}$alkyl, —SCF$_3$, —SO$_2$CF$_3$, —CHO, —COC$_{1-4}$alkyl, —CO$_2$C$_{1-4}$alkyl, —CO$_2$H, —N(R$^d$)R$^e$, —SO$_2$NR$^d$R$^e$, —NR$^d$SO$_2$R$^e$, —C(O)NR$^d$R$^e$, —NO$_2$, —CN, or halo, where $R^d$ and $R^e$ are each independently —H or —C$_{1-4}$alkyl.

In preferred embodiments of Formula (I), each $R^c$ moiety is independently fluoro, chloro, nitro, trifluoromethyl, methoxy, hydroxy, or trifluoromethoxy, or two adjacent $R^c$ moieties together form —O(CH$_2$)$_{1-2}$O— or —O(CF$_2$)O—. In some embodiments of Formula (I), $Ar^1$ is phenyl, 4-fluorophenyl, 4-nitrophenyl, 4-trifluoromethylphenyl, 4-chlorophenyl, 4-hydroxyphenyl, 4-methoxyphenyl, 4-hydroxy-3-methoxyphenyl, 3,4-dichlorophenyl, 3,4-difluorophenyl, 2-chlorophenyl, 3-chlorophenyl, 3-methoxyphenyl, 2-methoxyphenyl, 3,5-dichlorophenyl, 3-trifluoromethoxyphenyl, 3-fluorophenyl, 4-chloro-3-fluorophenyl, 3-chloro-4-fluorophenyl, 3-trifluoromethylphenyl, 2-pyridinyl, 3-pyridinyl, 4-pyridinyl, 1,3-benzodioxolyl, or 2,2-difluoro-1,3-benzodioxolyl. In still other embodiments of Formula (I), $Ar^1$ is unsubstituted phenyl, 4-fluorophenyl, or 4-trifluoromethoxyphenyl.

In certain embodiments of Formula (I), $Ar^2$ is phenyl substituted with one, two, or three $R^g$ moieties each at a meta or para position, and optionally with one or two additional $R^g$ moieties at an ortho position. In certain embodiments, $Ar^2$ is a monocyclic heteroaryl group substituted with one, two, or three $R^g$ moieties. In further embodiments, $Ar^2$ is naphthyl or bicyclic heteroaryl group unsubstituted or substituted with one, two, or three $R^l$ moieties where each $R^l$ moiety is independently C$_{1-4}$alkyl, perfluoroalkyl, perfluoroalkoxy, NO$_2$, —CN, or halo.

In certain embodiments, each $R^g$ moiety is independently halo, —C$_{1-4}$alkyl, —C$_{1-4}$alkyl-OH, perfluoroalkyl, perfluoroalkoxy, (monocyclic cycloalkyl), —S(O)$_{0-2}$C$_{1-4}$alkyl, —SCF$_3$, —SO$_2$CF$_3$, —CHO, —COC$_{1-4}$alkyl, —CO$_2$C$_{1-4}$alkyl, —CO$_2$H, —N(R$^h$)R$^i$, —SO$_2$NR$^j$R$^k$, —NR$^h$SO$_2$R$^i$, —C(O)NR$^j$R$^k$, —NO$_2$, —CN; or a phenoxy, benzyl, phenethyl, or benzoyl group unsubstituted or substituted with —C$_{1-4}$alkyl, perfluoroalkyl, perfluoroalkoxy, —NO$_2$, —CN, or halo. In certain embodiments, two adjacent $R^g$ moieties taken together form —O(CH$_2$)$_{1-2}$O-unsubstituted or substituted with one or two fluoro groups. In certain embodiments, each said $R^g$ moiety is independently chloro, fluoro, —CF$_3$, —OCF$_3$, —OCH$_2$CH$_3$, —OCH$_2$CF$_3$, —OCHF$_2$, —SCF$_3$, —SCH$_2$CH$_3$, —S(O)(O)N(CH$_3$)$_2$, or two adjacent $R^g$ moieties together form —OCF$_2$O—.

In certain embodiments, $R^h$ is H or —C$_{1-4}$alkyl, $R^i$ is —C$_{1-4}$alkyl or monoyclic cycloalkyl group, $R^h$ and $R^i$ taken together with the atoms to which they are attached form a monocyclic heterocycloalkyl ring, $R^j$ is H or —C$_{1-4}$alkyl, and $R^k$ is H, —C$_{1-4}$alkyl or a monoyclic cycloalkyl group. In certain embodiments, $R^j$ and $R^k$ taken together with the atoms to which they are attached form a monocyclic heterocycloalkyl ring In further embodiments of Formula (I), $Ar^2$ is a phenyl substituted at either or both of the meta and para positions with one, two or three $R^g$ moieties. In some embodiments of Formula (I), $Ar^2$ is a thiophenyl, pyridinyl, pyrimidinyl, or pyrazolyl group, each substituted with one, two, or three $R^g$ moieties. In some embodiments, $Ar^2$ is 3-trifluoromethyl-benzo[d]isoxazol-6-yl or 1-benzothiophen-2-yl substituted at the 5 position with methyl or trifluoromethoxy.

In some embodiments of Formula (I), each $R^g$ moiety is independently methyl, ethyl, isopropyl, tert-butyl, hydroxymethyl, 1-hydroxyethyl, cyanomethyl, cyano-dimethyl-methyl, trifluoromethyl, methoxy, ethoxy, propoxy, isopropoxy, butoxy, isobutoxy, trifluoromethoxy, difluoromethoxy, trifluoroethoxy, cyclopropylmethoxy, methylsulfanyl, ethylsulfanyl, isopropylsulfanyl, methylsulfonyl, formyl, acetyl, dimethylamino, morpholin-4-yl, sulfamoyl, dimethylsulfamoyl, cyclopropylsulfamoyl, piperidine-1-sulfonyl, pyrrolidine-1-sulfonyl, nitro, cyano, chloro, fluoro, iodo, phenoxy, benzyl, benzoyl, or phenethyl, or two adjacent $R^g$ moieties together form —O(CH$_2$)$_{1-2}$O— or —O(CF$_2$)O—. In further preferred embodiments of Formula (I), $Ar^2$ is 3,4-dimethylphenyl, 4-tert-butylphenyl, 4-cyanophenyl, 4-acetylphenyl, 4-methylphenyl, 4-chlorophenyl, 4-fluorophenyl, 4-trifluoromethylphenyl, 4-methoxyphenyl, 4-nitrophenyl, 3-methylphenyl, 3-trifluoromethoxyphenyl, 4-ethylphenyl, 4-isopropylphenyl, 3,4-dichlorophenyl, 3-chlorophenyl, 3-chloro-4-trifluoromethylphenyl, 4-ethoxyphenyl, 4-isopropoxyphenyl, 4-phenoxy-phenyl, 3-chloro-4-ethoxyphenyl, 3-chloro-4-isopropoxyphenyl, 3-fluoro-4-methylphenyl, 4-hydroxymethylphenyl, 4-formylphenyl, 3-formylphenyl, 4-trifluoroethoxyphenyl, 3-trifluoroethoxyphenyl, 4-chloro-3-methylphenyl, 4-chloro-3-fluorophenyl, 4-chloro-3-trifluoromethylphenyl, 3-fluoro-4-trifluoromethoxyphenyl, 4-ethoxy-3-fluorophenyl, 4-ethoxy-3-methylphenyl, 4-cyclopropylmethoxyphenyl, 4-butoxy-3-fluorophenyl, 4-butoxyphenyl, 3-fluoro-4-propoxyphenyl, 3-fluoro-4-isopropoxyphenyl, 4-isobutoxyphenyl, 4-methoxy-3-methylphenyl, 3-chloro-4-methylphenyl, 3,5-dimethylphenyl, 3-fluoro-4-trifluoromethylphenyl, 3-fluoro-5-trifluoromethylphenyl, 3-chloro-5-fluorophenyl, 4-propoxyphenyl, 4-isopropoxy-3-methylphenyl, 4-difluoromethoxy-3,5-difluorophenyl, 4-(cyano-dimethyl-methyl) phenyl, 4-acetyl-3-fluorophenyl, 3,5-dimethyl-4-isopropoxyphenyl, 3,4,5-trifluorophenyl, 4-benzoylphenyl, 3,5-difluorophenyl, 3,4-difluorophenyl, 4-dimethylaminophenyl, 4-methylsulfonylphenyl, 4-cyclopropylsulfamoylphenyl, 3-fluoro-4-methoxyphenyl, 1,4-benzodioxin-6-yl, 4-dimethylsulfamoylphenyl, 4-piperidine-1-sulfonylphenyl, 4-pyrrolidine-1-sulfonylphenyl, 3-chloro-4-fluorophenyl, 4-methylsulfanylphenyl, 4-cyano-3-fluorophenyl, 3-cyano-4-fluorophenyl, 4-isopropylsulfanylphenyl, 4-cyanomethylphenyl, 4-ethylsulfanylphenyl, 3-ethoxyphenyl, 3-propoxyphenyl, 3-butoxyphenyl, 4-trifluoromethoxyphenyl, 3-trifluoromethylphenyl, 4-(2-o-tolyl-ethyl)phenyl, 3-fluoro-4-(1-hydroxy-ethyl)phenyl, 4-iodophenyl, 4-ethoxy-3-trifluoromethylphenyl, 3,4-dimethoxyphenyl, 3-methoxyphenyl, 2,4-bis(trifluoromethyl)phenyl, 2-methoxy-4-(trifluoromethoxy)phenyl, 4-ethoxy-2-methylphenyl, 2,2-difluoro-1,3-benzodioxol-5-yl, 1,3-benzodioxol-5-yl, 5-acetyl-thiophen-2-yl, 6-methoxypyridin-3-yl, 6-ethoxypyridin-3-yl, 6-morpholin-4-ylpyridin-3-yl, 6-fluoro-5-methylpyridin-3-yl, 6-cyanopyridin-3-yl, 6-(dimethylamino)pyridine-3-yl, 2-morpholin-4-ylpyrimidin-5-yl, or 1-benzyl-1H-pyrazol-4-yl.

In other preferred embodiments of Formula (I), $Ar^2$ is a naphthyl, benzoxadiazolyl, indolyl, benzothiophenyl, quinolinyl, or indazolyl, each unsubstituted or substituted with one, two, or three $R^f$ moieties. In some embodiments of Formula (I), each $R^f$ moiety is independently methyl. In further preferred embodiments of Formula (I), $Ar^2$ is naphthyl, 2,1,3-benzoxadiazol-5-yl, 1H-indol-5-yl, 1H-indol-6-yl, 1-methyl-1H-indol-2-yl, 1-methyl-1H-indol-5-yl, 5-methyl-1-benzothiophen-2-yl, benzothiophen-3-yl, benzothiophen-5-yl, quinolin-3-yl, or 3-methyl-1H-indazol-6-yl.

In certain embodiments of Formula (I), $R^g$ and/or $R^f$ is perfluoroalkyl or perfluoroalkoxy.

In preferred embodiments of Formula (I), the secondary amine group adjacent to $Ar^1$ is in the

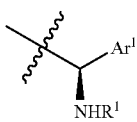

configuration. In further embodiments, the amine group is in the

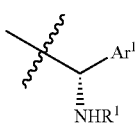

configuration.

Further preferred embodiments of Formula (I) encompass combinations of two or more of the preferred embodiments for each of $R^1$, $Ar^1$, and $Ar^2$ listed above. In certain embodiments, $Ar^1$ is phenyl optionally substituted with one or two $R^c$ substituents selected from halo, —$CF_3$, —CN, —$SCH_3$, —$SCF_3$, —S(O)(O)$CH_3$, or two adjacent substituents together form —$OCF_2O$— and $R^1$ is H. In certain embodiments, $Ar^1$ is (i) phenyl optionally substituted with one or two $R^c$ moieties selected from halo, —$CF_3$, —CN, —$OCHF_2$, —$OCH_3$, —$OCF_3$, —$CF_3$, —$SCH_3$, —$SCF_3$, —S(O)(O)$CH_3$, imidazolyl, pyrrolidinyl, pyridyl, phenyl, thiophenyl, or two adjacent substituents together form —$O(CH_2)_{2-3}O$— or —$OCF_2O$—; (ii) napthyl; (iii) thiophenyl optionally substituted with pyridinyl; (iv) thiazolyl; (v) benzothiophenyl; (vi) isoxazolyl; and $Ar^2$ is (i) phenyl optionally substituted with one, two, or three $R^g$ moieties each at a meta or para position, wherein each said $R^g$ moiety is independently chloro, fluoro, —$CF_3$, —CH(OH)$CH_3$, —OH, —$OCF_3$, —$OCH_3$, —$OCH_2CH_3$, —$OCH_2CF_3$, —$OCHF_2$, —$SCF_3$, —$SCH_2CH_3$, —S(O)(O)N($CH_3$)$_2$, —S(O)(O)NHC($CH_3$)$_3$, —S(O)(O)-thiomorpholin-4-yl, or two adjacent $R^g$ moieties together form —$OCH_2O$— unsubstituted or substituted with two fluoro atoms; (ii) 1-benzothiophen-2-yl optionally substituted at the 5- or 6-position with F, $CF_3$, methyl or trifluoromethoxy; (iii) benzo[d]isoxazol-6-yl optionally substituted at the 3 position with —$CF_3$, —$CH_3$, or —$CH_2CF_3$; (iv) quinolin-6-yl; or (v) 5-acetyl-thiophen-2-yl. In further embodiments, $Ar^2$ is a phenyl substituted with one, two or three $R^g$ moieties each at a meta or para position wherein each said $R^g$ moiety is independently chloro, fluoro, —$CF_3$, —$OCF_3$, —$OCH_2CH_3$, —$OCH_2CF_3$, —$OCHF_2$, —$SCF_3$, —$SCH_2CH_3$, —S(O)(O)N($CH_3$)$_2$, or two adjacent $R^g$ moieties together form —$OCF_2O$— and $R^1$ is H. In further embodiments, $Ar^1$ is (i) phenyl optionally substituted with one or two $R^c$ moieties selected from halo, —$CF_3$, —CN, —$SCH_3$, —$SCF_3$, —S(O)(O)$CH_3$, or two adjacent substituents together form —$OCF_2O$—; or (ii) napthyl; and $Ar^2$ is: (i) phenyl optionally substituted with one, two, or three $R^g$ moieties each at a meta or para position, wherein each said $R^g$ moiety is independently chloro, fluoro, —$CF_3$, —$OCF_3$, —$OCH_2CH_3$, —$OCH_2CF_3$, —$OCHF_2$, —$SCF_3$, —$SCH_2CH_3$, —S(O)(O)N($CH_3$)$_2$, or two adjacent $R^g$ moieties together form —$OCF_2O$—; (ii) 1-benzothiophen-2-yl substituted at the 5 position with methyl or trifluoromethoxy; or (iii) 3-trifluoromethyl-benzo[d]isoxazol-6-yl.

The invention also relates to pharmaceutically acceptable salts of the free acids or bases represented by Formula (I) preferably of the preferred embodiments described above and of the specific compounds exemplified herein. A "pharmaceutically acceptable salt" is intended to mean a salt of a free acid or base of a compound represented by Formula (I) that is non-toxic, biologically tolerable, or otherwise biologically suitable for administration to the subject. See, generally, S. M. Berge, et al., "Pharmaceutical Salts", J. Pharm. Sci., 1977, 66:1-19, and *Handbook of Pharmaceutical Salts, Properties, Selection, and Use*, Stahl and Wermuth, Eds., Wiley-VCH and VHCA, Zurich, 2002.

Preferred pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt. Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methyl benzoates, dinitrobenzoates, hydroxybenzoates, methoxybenzoates, phthalates, sulfonates, xylenesulfonates, phenylacetates, phenylpropionates, phenyl butyrates, citrates, lactates, γ-hydroxybutyrates, glycolates, tartrates, methane-sulfonates, propanesulfonates, naphthalene-1-sulfonates, naphthalene-2-sulfonates, and mandelates.

If a compound of Formula (I) contains a basic nitrogen, the desired pharmaceutically acceptable salt may be prepared by any suitable method available in the art, for example, by treatment of the free base with an inorganic acid, such as hydrochloric acid, hydrobromic acid, sulfuric acid, sulfamic acid, nitric acid, boric acid, phosphoric acid, and the like; or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid; an amino acid, such as aspartic acid or glutamic acid; an aromatic acid, such as benzoic acid, 2-acetoxybenzoic acid, naphthoic acid, or cinnamic acid; a sulfonic acid, such as laurylsulfonic acid, p-toluenesulfonic acid, methanesulfonic acid, or ethanesulfonic acid; or any compatible mixture of acids such as those given as examples herein.

If a compound of Formula (I) is an acid such as a carboxylic acid or sulfonic acid, the desired pharmaceutically acceptable salt may be prepared by any suitable method, for example, by treatment of the free acid with an inorganic or organic base, such as an amine (primary, secondary or tertiary), an alkali metal hydroxide, alkaline earth metal hydroxide, or any compatible mixture of bases such as those given as examples herein. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of the compounds of Formula (I). The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

Examples of prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formula (I). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-7}$alkyl, $C_{5-7}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in *Adv. Drug Delivery Rev.* 1996, 19, 115. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in *J. Med. Chem.* 1996, 39, 10. Free amines can also be derivatized as amides, sulfonamides or phosphonamides. All of these prodrug moieties may incorporate groups including ether, amine, and carboxylic acid functionalities.

The present invention also relates to pharmaceutically active metabolites of compounds of Formula (I). A "pharmaceutically active metabolite" means a pharmacologically active product of metabolism in the body of a compound of Formula (I) or a salt thereof. Prodrugs and active metabolites of a compound may be determined using routine techniques known or available in the art. See, e.g., Bertolini et al., *J. Med. Chem.* 1997, 40, 2011-2016; Shan et al., *J. Pharm. Sci.* 1997, 86 (7), 765-767; Bagshawe, *Drug Dev. Res.* 1995, 34, 220-230; Bodor, *Adv. Drug Res.* 1984, 13, 224-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

The compounds of Formula (I), and their pharmaceutically acceptable salts, pharmaceutically acceptable prodrugs, and pharmaceutically active metabolites (collectively, "active agents") of the present invention are useful as FAAH inhibitors in the methods of the invention. The active agents may be used in the inventive methods for the treatment of medical conditions, diseases, or disorders mediated through inhibition or modulation of FAAH, such as those described herein. Active agents according to the invention may therefore be used as an analgesic, anti-depressant, cognition enhancer, neuroprotectant, sedative, appetite stimulant, or contraceptive.

Exemplary medical conditions, diseases, and disorders mediated by FAAH activity include anxiety, depression, pain, sleep disorders, eating disorders, inflammation, multiple sclerosis and other movement disorders, HIV wasting syndrome, closed head injury, stroke, learning and memory disorders, Alzheimer's disease, epilepsy, Tourette's syndrome, epilepsy, Niemann-Pick disease, Parkinson's disease, Huntington's chorea, optic neuritis, autoimmune uveitis, symptoms of drug or alcohol withdrawal, nausea, emesis, sexual dysfunction, post-traumatic stress disorder, cerebral vasospasm, diabetes, metabolic syndrome, osteoarthritis and osteoporosis.

Thus, the active agents may be used to treat subjects diagnosed with or suffering from such a disease, disorder, or condition. The term "treat" or "treating" as used herein is intended to refer to administration of an agent or composition of the invention to a subject for the purpose of effecting a therapeutic benefit through modulation of FAAH activity. Treating includes reversing, ameliorating, alleviating, inhibiting the progress of, lessening the severity of, reducing the incidence of, or preventing a disease, disorder, or condition, or one or more symptoms of such disease, disorder or condition mediated through modulation of FAAH activity. The term "subject" refers to a mammalian patient in need of such treatment, such as a human. "Modulators" include both inhibitors and activators, where "inhibitors" refer to compounds that decrease, prevent, inactivate, desensitize or down-regulate FAAH expression or activity, and "activators" are compounds that increase, activate, facilitate, sensitize, or up-regulate FAAH expression or activity.

Accordingly, the invention relates to methods of using the active agents described herein to treat subjects diagnosed with or suffering from a disease, disorder, or condition mediated through FAAH activity, such as: anxiety, pain, sleep disorders, eating disorders, inflammation, movement disorders (e.g., multiple sclerosis), glucose and lipid metabolism (e.g. diabetes) and bone homeostasis (e.g. osteoporosis).

Symptoms or disease states are intended to be included within the scope of "medical conditions, disorders, or diseases." For example, pain may be associated with various diseases, disorders, or conditions, and may include various etiologies. Illustrative types of pain treatable with a FAAH-modulating agent, in one example herein a FAAH-inhibiting agent, according to the invention include cancer pain, postoperative pain, GI tract pain, spinal cord injury pain, visceral hyperalgesia, thalamic pain, headache (including stress headache and migraine), low back pain, neck pain, musculoskeletal pain, peripheral neuropathic pain, central neuropathic pain, neurogenerative disorder related pain, and menstrual pain. HIV wasting syndrome includes associated symptoms such as appetite loss and nausea. Parkinson's disease includes, for example, levodopa-induced dyskinesia. Treatment of multiple sclerosis may include treatment of symptoms such as spasticity, neurogenic pain, central pain, or bladder dysfunction. Symptoms of drug withdrawal may be caused by, for example, addiction to opiates or nicotine. Nausea or emesis may be due to chemotherapy, postoperative, or opioid related causes. Treatment of sexual dysfunction may include improving libido or delaying ejaculation. Treatment of cancer may include treatment of glioma. Sleep disorders include, for example, sleep apnea, insomnia, and disorders calling for treatment with an agent having a sedative or narcotic-type effect. Eating disorders include, for example, anorexia or appetite loss associated with a disease such as cancer or HIV infection/AIDS.

In treatment methods according to the invention, an effective amount of at least one active agent according to the invention is administered to a subject suffering from or diagnosed as having such a disease, disorder, or condition. A "therapeutically effective amount" or "effective amount" means an amount or dose of a FAAH-modulating agent sufficient to generally bring about a desired therapeutic benefit in patients in need of treatment for a disease, disorder, or condition mediated by FAAH activity. Effective amounts or doses of the active agents of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. An exemplary dose is in the range of from about 0.0001 to about 200 mg of active agent per kg of subject's body weight per day, preferably about 0.001 to 100 mg/kg/day, or about 0.01 to 35 mg/kg/day, or about 0.1 to 10 mg/kg daily in single or divided dosage units (e.g., BID, TID, QID). For a 70-kg human, an illustrative range for a suitable dosage amount is from about 0.05 to about 7 g/day, or about 0.2 to about 5 g/day. Once improvement of the patient's disease, disorder, or condition has occurred, the dose may be adjusted for maintenance treatment. For example, the dosage or the frequency of administration, or both, may be reduced as a function of the symptoms, to a level at which the desired therapeutic effect is maintained. Of course, if symptoms have been alleviated to an appropriate level, treatment may cease. Patients may, however, require intermittent treatment on a long-term basis upon any recurrence of symptoms.

In addition, the active agents of the invention may be used in combination with additional active ingredients in the treatment of the above conditions. The additional active ingredients may be coadministered separately with an active agent of Formula (I), or included with such an agent in a pharmaceutical composition according to the invention. In an exemplary embodiment, additional active ingredients are those that are known or discovered to be effective in the treatment of conditions, disorders, or diseases mediated by FAAH activity, such as another FAAH modulator or a compound active against another target associated with the particular condition, disorder, or disease. The combination may serve to increase efficacy (e.g., by including in the combination a compound potentiating the potency or effectiveness of an active agent according to the invention), decrease one or more side effects, or decrease the required dose of the active agent according to the invention. In one illustrative embodiment, a composition according to the invention may contain one or more additional active ingredients selected from opioids, non-steroidal anti-inflammatory drugs (NSAID) (e.g., ibuprofen, cyclooxygenase-2 (COX-2) inhibitors, and naproxen), gabapentin, pregabalin, tramadol, acetaminophen, and aspirin.

The active agents of the invention are used, alone or in combination with one or more additional active ingredients, to formulate pharmaceutical compositions of the invention. A pharmaceutical composition of the invention comprises: (a) an effective amount of at least one active agent in accordance with the invention; and (b) a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of a agent and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the active agents of the invention can be provided in the form of tablets or capsules, or as a solution, emulsion, or suspension. To prepare the oral compositions, the active agents may be formulated to yield a dosage of, e.g., from about 5 mg to 5 g daily, or from about 50 mg to 5 g daily, in single or divided doses. For example, a total daily dosage of about 5 mg to 5 g daily may be accomplished by dosing once, twice, three, or four times per day.

Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, compositions may be formulated for rectal administration as a suppository. For parenteral use, including intravenous, intramuscular, intraperitoneal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 μg/kg/minute of agent admixed with a pharmaceutical carrier over a period ranging from several minutes to several days.

For topical administration, the agents may be mixed with a pharmaceutical carrier at a concentration of about 0.1% to about 10% of drug to vehicle. Another mode of administering the agents of the invention may utilize a patch formulation to affect transdermal delivery.

Active agents may alternatively be administered in methods of this invention by inhalation, via the nasal or oral routes, e.g., in a spray formulation also containing a suitable carrier.

Exemplary active agents useful in methods of the invention will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I).

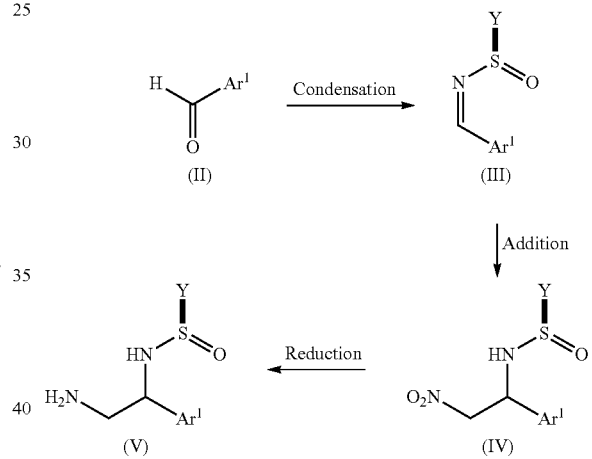

Scheme A

Chiral N-protected ethylene diamines (V) are accessed via condensation of an aldehyde with a chiral sufinamide as shown in Scheme A. Aldehydes (II) are treated with a chiral sufinamide, preferably (R) or (S) t-butyl or tolylsulfinamide, in the presence of Ti(OEt)$_4$ in solvents such as THF at temperatures ranging from 0° C. to rt to give the corresponding imine (III). In the schemes, Y is t-butyl or tolyl. Compounds (1V) are formed by addition of nitromethane (CH$_3$NO$_2$) in the presence of base, such as NaOH, KOH, KOt-Bu, NaOt-Bu, TBAF, or NaH, in solvents such as THF or MeOH, at temperatures between 0° C. and the reflux temperature of the solvent. Ethylene diamines (V) are obtained by reduction of the nitro group of compounds (1V) using generally known methods such as hydrogenation over Pd catalyst using H$_2$, NH$_4$HCO$_2$, or cyclohexadiene as the hydrogen source in solvents such as MeOH and EtOH at temperatures between room temperature and the reflux temperature of the solvent. Alternatively, the nitro group can be reduced through the use of a stoichiometric reductant such as Zn metal powder in the presence of NH$_4$Cl or HOAc in a solvent such as MeOH, EtOH, or THF at temperatures between room temperature and the reflux temperature of the solvent. Sulfinamide protected ethylene diamines (V) are installed via nucleophilic aromatic substitution ($S_NAr$) reactions shown in Scheme B and are subsequently deprotected using known methods described therein.

Scheme B

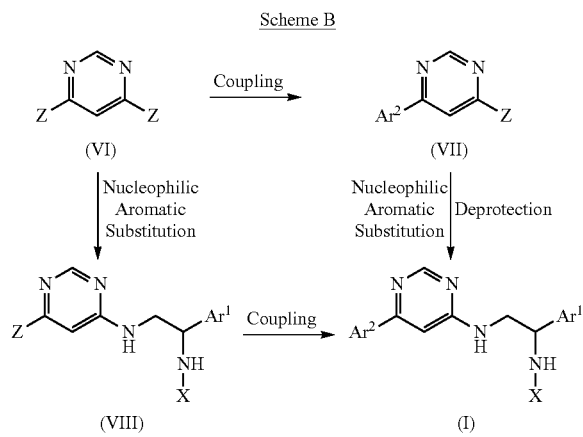

Referring to Scheme B, compounds of Formula (I) are prepared from pyrimidines (VI), where Z is halo or another suitable substituent. Various substituted pyrimidines are commercially available or are prepared using known methods. Pyrimidines of formula (VII) are obtained via palladium-mediated cross-coupling of reagents (VI) with suitable aryl boronic acids. Preferably, pyrimidines of formula (VI) are treated with the desired boronic acid in the presence of a base such as $K_3PO_4$ or KF, in a suitable polar solvent such as $CH_3CN$, 1,2-dimethoxyethane (DME), tetrahydrofuran (THF), water, or a mixture thereof, at a temperature from about 50° C. to about 180° C. using conventional heating or a microwave reactor. Pyrimidines (VII) are converted to compounds of Formula (I) via nucleophilic aromatic substitution ($S_NAr$) with N-protected aryl-substituted ethylene diamines, such as compounds of Formula (V) or other appropriate commercially available chemical reagents, in the presence of a suitable base such as $NaHCO_3$, $(i-Pr)_2EtN$, $Et_3N$, or a mixture thereof, either neat or in a solvent such as 1,4-dioxane, THF, t-amyl alcohol, n-BuOH, or a mixture thereof, at a temperature from about 80° C. to about 150° C. Suitable protecting groups (X) for the amine include t-butyl carbamate (Boc), benzyl, acetyl, and t-butyl- or tolyl sufinamide.

In alternative embodiments, pyrimidines of Formula (I) are obtained by $S_NAr$ displacement of compounds (VI) with N-protected ethylene diamines, such as compounds of Formula (V) or other appropriate commercially available chemical reagents, followed by palladium-mediated cross-coupling using known procedures. Certain embodiments of compounds of Formula (I) contain a protected form of an amine. Certain embodiments of compounds of Formula (I) contain a deprotected form of an amine. Where deprotection of Formula (I) compounds is desired, the protecting group may be removed using generally accepted methods. More specifically, a group such as a t-butyl carbamate or t-butyl sulfinamide may be removed with an acid such as trifluoroacetic acid or HCl, in a solvent such as $Et_2O$, dioxane, EtOH, or MeOH to afford the acid salts of compounds (1).

The free base of compounds (1) can be obtained by known methods to one skilled in the art. In preferred methods, the free base is obtained by filtration of the salt through $PL-HCO_3$ MP resin using an alcoholic solvent, preferably MeOH.

Compounds of Formula (I) may be converted to their corresponding salts by applying general techniques described in the art. For example, a compound of Formula (I) may be treated with trifluoroacetic acid, HCl, or citric acid in a solvent such as $Et_2O$, 1,4-dioxane, DCM, THF, or MeOH to provide the corresponding salt forms.

Compounds prepared according to the schemes described above may be obtained as single enantiomers or diastereomers by enantio- or diastero-specific synthesis, or by resolution. Compounds prepared according to the schemes above may alternatively be obtained as racemic (1:1) or non-racemic (not 1:1) mixtures or as mixtures of diastereomers or regioisomers. Where racemic and non-racemic mixtures of enantiomers are obtained, single enantiomers may be isolated using conventional separation methods, such as chiral chromatography, recrystallization, diastereomeric salt formation, derivatization into diastereomeric adducts, biotransformation, or enzymatic transformation. Where regioisomeric or diastereomeric mixtures are obtained, single isomers may be separated using conventional methods such as chromatography or crystallization.

The following specific examples are provided to further illustrate the invention and various preferred embodiments.

EXAMPLES

Chemistry

In obtaining the characterization data described in the examples below, the following analytical protocols were followed unless otherwise indicated.

NMR spectra were obtained on Bruker model DRX spectrometers (400, 500, or 600 MHz). The format of $^1H$ NMR data below is: chemical shift in ppm downfield of the tetramethylsilane reference (multiplicity, coupling constant J in Hz, integration).

Mass spectra were obtained on an Agilent series 1100 MSD using electrospray ionization (ESI) in either positive or negative modes as indicated. Calculated mass corresponds to the exact mass.

Thin-layer chromatography was performed using Merck silica gel 60 $F_{254}$ 2.5 cm×7.5 cm 250 μm or 5.0 cm×10.0 cm 250 μm pre-coated silica gel plates. Preparative thin-layer chromatography was performed using EM Science silica gel 60 $F_{254}$ 20 cm×20 cm 0.5 mm pre-coated plates with a 20 cm×4 cm concentrating zone.

Normal phase purification was typically done by normal phase flash column chromatography (FCC) with RediSep® silica gel columns using EtOAc/hexanes or $CH_2Cl_2$/MeOH as eluent unless otherwise specified.

Reverse phase high performance liquid chromatography (HPLC) was performed under the following conditions: Instrument, Shimadzu; Column, Phenomenex Gemini column 5 μm C18 (150×21.2 mm) or Waters Xterra RP18 OBD 5 μm (100×30 mm); Gradient, 95:5 to 0:100 water (0.05% TFA)/$CH_3CN$ (0.05% TFA); Flow rate, 30-80 mL/min; Detection, UV at A=220-254 nM, Gilson; Column, Phenomenex LUNA column 5 μm C18 (250×50 mm) or Waters XBridge Prep C18 OBD 5 μm (30×150 mm); Gradient, 95:5 to 0:100 water (0.05% TFA)/$CH_3CN$ (0.05% TFA); Flow rate, 30-80 mL/min; Detection, UV at A=220-254 nM.

Microwave reactions were carried out in either a CEM Discover® or a Biotage Initiator™ Microwave at specified temperatures.

Where solutions were "concentrated", they were concentrated using a rotary evaporator under reduced pressure. Unless otherwise specified, reaction solutions were stirred at room temperature (rt) under a $N_{2(g)}$ atmosphere.

Hydrochloride salts were obtained by treating the corresponding free bases with HCl (4 N in dioxane or 1.25 N in MeOH) at rt. The mixtures were either concentrated to obtain the HCl salt, or the resulting solid was isolated by filtration.

Trifluoroacetic acid salts were obtained by purification of the crude reaction product by preparative reverse phase HPLC.

Intermediate 1: 4-Chloro-6-(3-chloro-4-trifluoromethyl-phenyl)-pyrimidine

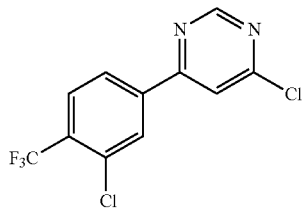 [SMILES: FC(F)(F)c1ccc(-c2cc(Cl)ncn2)cc1Cl]

To a solution of $CH_3CN$ and water (75:25 mL) that has been degassed by bubbling $N_2$ into the solvent was added 4,6-dichloro-pyrimidine (3.63 g, 22.7 mmol) and $Ph_3P$ (840 mg, 2.20 mmol). De-gassing was continued for an additional 15 min before adding 3-chloro-4-trifluoromethylphenyl boronic acid (5 g, 22 mmol), $Pd(OAc)_2$ (250 mg, 1.11 mmol) and $K_3PO_4$ (9.4 g, 44.3 mmol). The resulting mixture was stirred at rt for 2 h before diluting with water and extracting with EtOAc. The organic layer was dried ($Na_2SO_4$), and concentrated. The crude residue was purified (FCC) to give the title compound (2.3 g, 35%).

Intermediate 2: 2,2-Difluoro-5-(4,4,5,5-tetramethyl-[1,3,2]dioxaborolan-2-yl)-benzo[1,3]dioxole

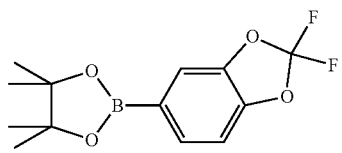 [SMILES: CC1(C)OB(c2ccc3c(c2)OC(F)(F)O3)OC1(C)C]

To an 80 mL microwave vessel was added 5-bromo-2,2-difluoro-benzo[1,3]dioxole (2.0 g, 8.44 mmol), bis(pinocolato)diboron (2.36 g, 9.28 mmol), potassium acetate (1.66 g, 16.9 mmol), $Pd(dppf)Cl_2 \cdot CH_2Cl_2$ (689 mg, 0.84 mmol) and 1,4-dioxane (25 mL). The vessel was purged with $N_2$ and then heated via microwave irradiation for 45 min at 140° C. The reaction mixture was diluted, filtered through a pad of Celite® and then filtered through a 0.45 μM nylon filter to remove residual palladium particulates, dried ($Na_2SO_4$) and concentrated. The crude material was purified (FCC) to yield the title compound as a green oil (1.41 g, 59%).

Intermediate 3: 4,4,5,5-Tetramethyl-2-(5-trifluoromethoxy-benzo[b]thiophen-2-yl)-[1,3,2]dioxaborolane

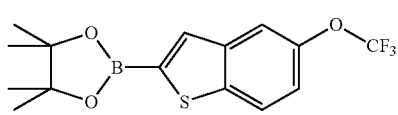 [SMILES: CC1(C)OB(c2cc3cc(OC(F)(F)F)ccc3s2)OC1(C)C]

Step A: 5-Trifluoromethoxy-benzo[b]thiophene. A mixture of 5-trifluoromethoxy-benzo[b]thiophene-2-carboxylic acid (2.00 g, 7.63 mmol) and 1,8-diazabicyclo[5.4.0]undec-7-ene (DBU) (5.0 mL, 32 mmol) in DMA (12 mL) was heated via microwave irradiation at 200° C. for 1 h. The reaction was cooled to rt, diluted with HCl (1 N aq., 15 mL) and extracted with EtOAc (15 mL). The organic layer was washed with water (10 mL), dried ($Na_2SO_4$) and concentrated. The residue was taken up in $Et_2O$ (25 mL) and washed with water (25 mL). The aqueous layer was extracted with $Et_2O$ (10 mL×2). The combined $Et_2O$ layers were dried ($Na_2SO_4$) and concentrated. The crude material was purified (FCC) to yield the title compound (518 mg, 31%).

Step B: 4,4,5,5-Tetramethyl-2-(5-trifluoromethoxy-benzo[b]thiophen-2-yl)-[1,3,2]dioxaborolane. To a 2-necked round bottom flask was added $[Ir(OMe)(COD)]_2$ (15 mg, 0.02 mmol) and 4,4'-di-tert-butyl-2,2'-bipyridine (dtbpy) (12 mg, 0.05 mmol) and the flask was evacuated and refilled with $N_2$. The flask was charged with a solution consisting of 5-trifluoromethoxy-benzo[b]thiophene (330 mg, 1.5 mmol) and hexane (9 mL), followed by pinacolborane (0.28 mL, 1.9 mmol). The reaction mixture was allowed to stir at rt for 3.5 h before diluting with $CH_2Cl_2$ (10 mL) and washing with water (10 mL). The organic layer was dried ($Na_2SO_4$), concentrated and purified (FCC) to yield the title compound (350 mg, 68%).

Intermediate 4: 4-trifluoromethylsulfanyl-benzene boronic acid

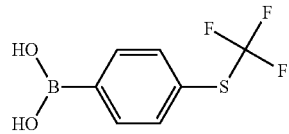 [SMILES: OB(O)c1ccc(SC(F)(F)F)cc1]

Step A: 4,4,5,5-Tetramethyl-2-(4-trifluoromethylsulfanyl-phenyl)-[1,3,2]dioxaborolane. The title compound was prepared using methods analogous to those described for Intermediate 2 substituting 1-bromo-4-trifluoromethylsulfanyl-benzene as a starting material.

Step B: 4-trifluoromethylsulfanyl-benzene boronic acid. To a round-bottomed flask was added 4,4,5,5-tetramethyl-2-(4-trifluoromethylsulfanyl-phenyl)-[1,3,2]dioxaborolane (960 mg, 3.16 mmol) and sodium periodate (2.03 g, 9.48 mmol) in THF and water (4:1, 26 mL). The resulting suspension was stirred at rt for 30 min. HCl (1 N aq., 2.21 mL) was added to the suspension and the reaction mixture was stirred at rt for 18 h. The resulting precipitate was removed by filtration and washed with hexanes. The filtrate was diluted with water (25 mL) and extracted with EtOAc (25 mL). The aqueous layer was extracted with EtOAc (10 mL×2), and the combined organic layers dried ($Na_2SO_4$) and concentrated to yield the title compound (512 mg, 73%).

Intermediate 5: 3-Trifluoromethyl-benzo[d]isoxazole-6-boronic acid

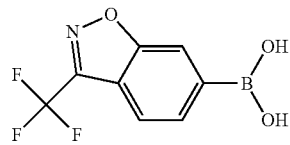 [SMILES: OB(O)c1ccc2c(C(F)(F)F)noc2c1]

Step A: 1-(4-Bromo-2-fluoro-phenyl)-2,2,2-trifluoro-ethanol. A mixture of 4-bromo-2-fluoro-benzaldehyde (8.12 g, 40.0 mmol) and (trifluoromethyl)trimethylsilane (7.50 mL, 48.0 mmol) in THF (40 mL) was cooled to 0° C. before treating with TBAF (1 M in THF, 0.6 mL) and warming to rt. After 3 h, an additional portion of TBAF (1 M in THF, 8.0 mL) was added. The resultant mixture was allowed to stir for 10 min before adding HCl (1 N aq., 40 mL) and extracting with Et$_2$O (40 mL). The Et$_2$O layer was dried (MgSO$_4$) and concentrated to yield the title compound (10.7 g, 98%).

Step B: 1-(4-Bromo-2-fluoro-phenyl)-2,2,2-trifluoro-ethanone. Dess-Martin periodinane (16.57 g, 39.06 mmol) was added to a solution of 1-(4-bromo-2-fluoro-phenyl)-2,2,2-trifluoro-ethanol (10.66 g, 39.06 mmol) in DCM (100 mL) and the reaction mixture was stirred at rt for 1.5 h. Na$_2$S$_2$O$_3$ (10% aq., 100 mL) was added and the resulting mixture extracted with CH$_2$Cl$_2$ (100 mL). The organic layer was washed with Na$_2$S$_2$O$_3$ (50 mL×2), NaHCO$_3$ (satd. aq., 100 mL×2), and brine (100 mL×2). The organic layers were dried (Na$_2$SO$_4$) and concentrated. The crude material was purified (FCC) to yield the title compound (3.20 g, 30%).

Step C: 1-(4-Bromo-2-fluoro-phenyl)-2,2,2-trifluoro-ethanone oxime. To a solution consisting of 1-(4-bromo-2-fluoro-phenyl)-2,2,2-trifluoro-ethanone (3.12 g, 11.5 mmol) and MeOH (50 mL) was added hydroxylamine hydrochloride (4.00 g, 57.5 mmol) and sodium acetate (5.90 g, 71.9 mmol). The resulting mixture was heated at 64° C. for 19 h, after which time additional hydroxylamine hydrochloride (2.40 g, 34.5 mmol) and sodium acetate (3.54 g, 43.1 mmol) were added. Heating was continued for 24 h and the mixture filtered to remove solids. The filtrate was diluted with EtOAc (150 mL), washed with water (150 mL), dried (Na$_2$SO$_4$) and concentrated. The title compound was obtained as a 70:30 ratio of the E and Z oxime isomers (3.28 g, 100%).

Step D: 6-Bromo-3-trifluoromethyl-benzo[d]isoxazole. A solution consisting of 1-(4-bromo-2-fluoro-phenyl)-2,2,2-trifluoro-ethanone oxime (3.2 g, 11 mmol), 1,8-diazabicyclo[5.4.0]undec-7-ene (DBU) (1.1 mL, 7.4 mmol) and THF (42 mL) was heated at 150° C. via microwave irradiation for 30 min. The reaction mixture was diluted with CH$_2$Cl$_2$ (25 mL) and washed with HCl (1 N aq., 25 mL). The organic layer was then dried (Na$_2$SO$_4$), concentrated and purified (FCC) to yield the title compound (1.97 g, 66%).

Step E: 3-Trifluoromethyl-benzo[d]isoxazole-6-boronic acid. Title compound was prepared using methods analogous to those described in Intermediate 4.

Example 1

(1R)—N$^2$-{6-[3-Chloro-4-(trifluoromethyl)phenyl]pyrimidin-4-yl}-1-phenylethane-1,2-diamine hydrochloride acid salt

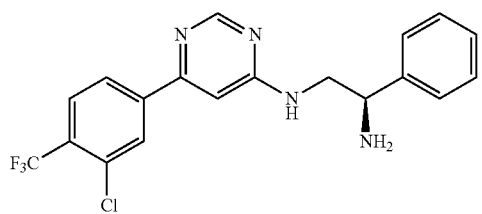 [SMILES: N[C@@H](CNc1cc(-c2ccc(C(F)(F)F)c(Cl)c2)ncn1)c1ccccc1]

Step A: tert-Butyl[(1R)-2-({6-[3-chloro-4-(trifluoromethyl)phenyl]pyrimidin-4-yl}amino)-1-phenylethyl]carbamate. To a solution of 4-chloro-6-(3-chloro-4-trifluoromethyl-phenyl)-pyrimidine (220 mg, 0.75 mmol) in dioxane (6 mL) was added [2-amino-(1R)-phenyl-ethyl]-carbamic acid tert-butyl ester (177 mg, 0.75 mmol) (Gerber-Lemaire et. al. Heterocycles 2006, 69, 179-192) and NaHCO$_3$ (378 mg, 4.50 mmol). The reaction mixture was heated at 100° C. for 16 h, then cooled to rt and diluted with CH$_2$Cl$_2$ (25 mL), washed with water (20 mL), dried (MgSO$_4$) and concentrated. The crude material was purified (FCC) to yield the final product (208 mg, 56%).

Step B: A HCl solution (2 M in Et$_2$O, 1.01 mL) was added to tert-butyl[(1R)-2-({6-[3-chloro-4-(trifluoromethyl)phenyl]pyrimidin-4-yl}amino)-1-phenylethyl]carbamate (200 mg, 0.41 mmol) in CH$_2$Cl$_2$ (4 mL). The reaction mixture was stirred at rt overnight. The precipitate was filtered and washed with Et$_2$O to yield the title compound (138 mg, 79%). MS (ESI): mass calcd. for C$_{19}$H$_{16}$ClF$_3$N$_4$, 392.10; m/z found, 393.1 [M+H]$^+$. $^1$H NMR (CD$_3$OD): 8.85 (s, 1H), 8.13 (s, 1H), 8.04 (d, J=8.3 Hz, 1H), 7.93 (d, J=8.3 Hz, 1H), 7.56-7.44 (m, 5H), 7.15 (s, 1H), 4.74-4.70 (m, 1H), 4.26 (dd, J=14.1, 7.1 Hz, 1H), 4.14 (dd, J=14.4, 7.1 Hz, 1H).

Examples 2 to 3 were prepared using methods analogous to those described in Example 1.

Example 2

(1R)-{2-[6-(3-Chloro-4-trifluoromethyl-phenyl)-pyrimidin-4-ylamino]-1-phenyl-ethyl}-carbamic acid tert-butyl ester

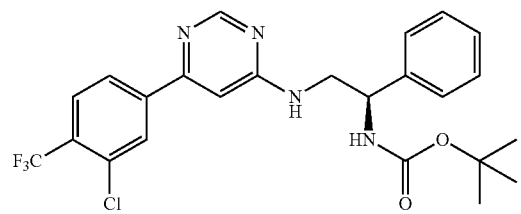 [SMILES: CC(C)(C)OC(=O)N[C@@H](CNc1cc(-c2ccc(C(F)(F)F)c(Cl)c2)ncn1)c1ccccc1]

MS (ESI): mass calcd. for C$_{24}$H$_{24}$ClF$_3$N$_4$O$_2$, 492.15; m/z found, 493.2 [M+H]$^+$. $^1$H NMR (CDCl$_3$): 8.66 (s, 1H), 8.20-8.17 (br s, 1H), 8.02-7.79 (br s, 1H), 7.77 (d, J=8.2 Hz, 1H), 7.40-7.38 (m, 2H), 7.34-7.33 (m, 3H), 6.98-6.80 (br s, 1H), 5.60-5.50 (br s, 1H), 5.33-5.19 (br s, 1H), 4.92-4.87 (m, 1H), 3.97-3.88 (br s, 1H), 3.76-3.68 (br s, 1H), 1.47-1.38 (br s, 9H).

Example 3

(1S)—N$^2$-{6-[3-Chloro-4-(trifluoromethyl)phenyl]pyrimidin-4-yl}-1-phenylethane-1,2-diamine hydrochloride acid salt

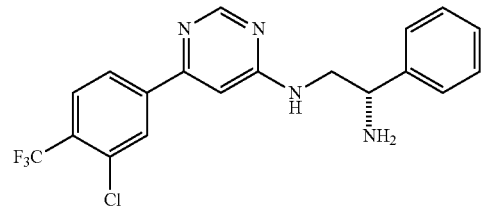 [SMILES: N[C@H](CNc1cc(-c2ccc(C(F)(F)F)c(Cl)c2)ncn1)c1ccccc1]

MS (ESI): mass calcd. for C$_{19}$H$_{16}$ClF$_3$N$_4$, 392.10; m/z found, 393.1 [M+H]$^+$. $^1$H NMR (CD$_3$OD): 8.85 (s, 1H), 8.13

(s, 1H), 8.04 (d, J=8.3 Hz, 1H), 7.93 (d, J=8.3 Hz, 1H), 7.56-7.44 (m, 5H), 7.15 (s, 1H), 4.74-4.70 (m, 1H), 4.26 (dd, J=14.1, 7.1 Hz, 1H), 4.14 (dd, J=14.4, 7.1 Hz, 1H).

Example 4

(1R)—N²-{6-[3-Fluoro-4-(trifluoromethyl)phenyl]pyrimidin-4-yl}-1-phenylethane-1,2-diamine hydrochloride acid salt

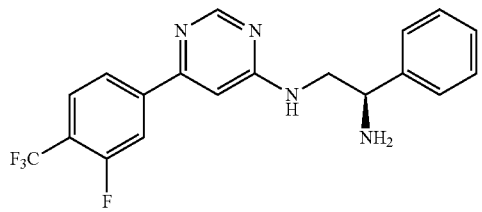 [SMILES: N[C@@H](CNc1cc(-c2ccc(C(F)(F)F)c(F)c2)ncn1)c1ccccc1]

Step A: [2-(6-Chloro-pyrimidin-4-ylamino)-1-phenyl-ethyl]-carbamic acid tert-butyl ester. To a solution of 4,6-dichloropyrimidine (4.32 g, 29.0 mmol) in dioxane (150 mL) was added [2-amino-(1R)-phenyl-ethyl]-carbamic acid tert-butyl ester (6.86 g, 29.0 mmol) and NaHCO₃ (14.6 g, 174 mmol). The reaction mixture was heated to 100° C. overnight. The reaction mixture was cooled to rt, diluted with CH₂Cl₂ (150 mL) and washed with water (200 mL×2). The combined organic layers were dried (Na₂SO₄), and concentrated under reduced pressure. The residue was purified (FCC) to yield the desired product (8.11 g, 80%).

Step B: tert-Butyl-[(1R)-2-({6-[3-fluoro-4-(trifluoromethyl)phenyl]pyrimidin-4-yl}amino)-1-phenylethyl]carbamate. [2-(6-Chloro-pyrimidin-4-ylamino)-1-phenyl-ethyl]-carbamic acid tert-butyl ester (87 mg, 0.25 mmol), 3-fluoro-4-(trifluoromethyl)-phenyl boronic acid (57 mg, 0.28 mmol), Pd(PPh₃)₄ (2.9 mg, 2.5 μmol) and K₃PO₄ (110 mg, 0.50 mmol) were placed in a sealed tube which was evacuated and refilled with N₂. 1,2-Dimethoxyethane (2 mL) and water (0.5 mL) were added to the sealed tube. The reaction mixture was stirred at 85° C. overnight. The reaction mixture was cooled to rt and was filtered through a pad of MgSO₄. The pad was washed with CH₂Cl₂. The crude filtrate was concentrated under reduced pressure and the residue was purified via reverse phase chromatography to yield the title compound (87.0 mg, 59%).

Step C: (1R)—N²-{6-[3-Fluoro-4-(trifluoromethyl)phenyl]pyrimidin-4-yl}-1-phenylethane-1,2-diamine hydrochloride acid salt. Title compound was prepared using methods similar to those described in Example 1. MS (ESI): mass calcd. for $C_{19}H_{16}F_4N_4$, 376.13; m/z found, 377.2 [M+H]⁺. ¹H NMR (CD₃OD): 8.86 (s, 1H), 7.99-7.96 (m, 1H), 7.89 (d, J=11.0 Hz, 1H), 7.83 (d, J=7.7 Hz, 1H), 7.56-7.54 (m, 2H), 7.52-7.46 (m, 3H), 7.14 (s, 1H), 4.73-4.71 (m, 1H), 4.25 (dd, J=14.0, 6.9 Hz, 1H), 4.13 (dd, J=14.0, 6.6 Hz, 1H).

Examples 5 to 23 were prepared using methods analogous to those described in Example 4.

Example 5

(1R)-1-Phenyl-N²-{6-[4-(trifluoromethyl)phenyl]pyrimidin-4-yl}ethane-1,2-diamine hydrochloride acid salt

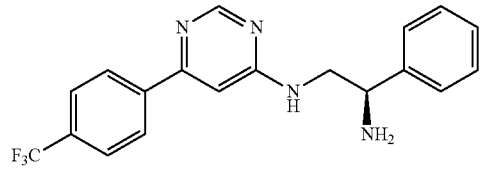 [SMILES: N[C@@H](CNc1cc(-c2ccc(C(F)(F)F)cc2)ncn1)c1ccccc1]

MS (ESI): mass calcd. for $C_{19}H_{17}F_3N_4$, 358.14; m/z found, 359.2 [M+H]⁺. ¹H NMR (CD₃OD): 8.86 (s, 1H), 8.03 (d, J=8.2 Hz, 2H), 7.94 (d, J=8.2 Hz, 2H), 7.55-7.46 (m, 5H), 7.12 (s, 1H), 4.73-4.70 (m, 1H), 4.26 (dd, J=14.3, 6.9 Hz, 1H), 4.13 (dd, J=14.8, 7.1 Hz, 1H).

Example 6

(1R)-1-Phenyl-N²-{6-[4-(trifluoromethoxy)phenyl]pyrimidin-4-yl}ethane-1,2-diamine hydrochloride acid salt

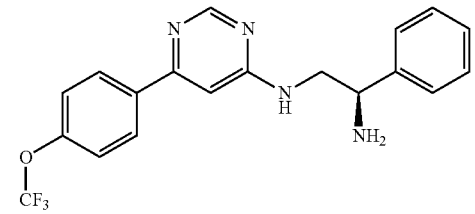

MS (ESI): mass calcd. for $C_{19}H_{17}F_3N_4O$, 374.14; m/z found, 375.2 [M+H]⁺. ¹H NMR (CD₃OD): 8.83 (s, 1H), 7.96 (d, J=8.2 Hz, 2H), 7.56-7.47 (m, 7H), 7.07 (s, 1H), 4.72-4.70 (m, 1H), 4.24 (dd, J=14.0, 6.9 Hz, 1H), 4.12 (dd, J=14.0, 6.6 Hz, 1H).

Example 7

(1R)—N²-{6-[3-Chloro-4-(trifluoromethoxy)phenyl]pyrimidin-4-yl}-1-phenylethane-1,2-diamine hydrochloride acid salt

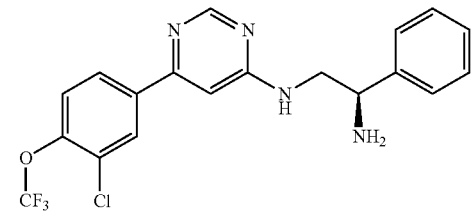

MS (ESI): mass calcd. for $C_{19}H_{16}ClF_3N_4O$, 408.10; m/z found, 409.1 [M+H]⁺. ¹H NMR (CD₃OD): 8.84 (s, 1H), 8.12 (s, 1H), 7.90-7.88 (m, 1H), 7.73-7.71 (m, 1H), 7.55-7.46 (m, 5H), 7.10 (s, 1H), 4.73-4.70 (m, 1H), 4.26 (dd, J=14.3, 7.1 Hz, 1H), 4.13 (dd, J=14.0, 6.6 Hz, 1H).

Example 8

(1R)—N²-{6-[3-Fluoro-4-(trifluoromethoxy)phenyl]pyrimidin-4-yl}-1-phenylethane-1,2-diamine hydrochloride acid salt

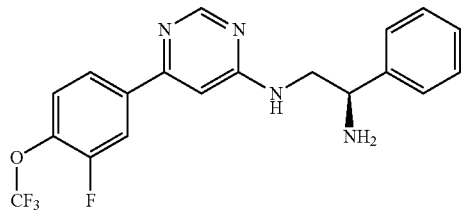

MS (ESI): mass calcd. for $C_{19}H_{16}F_4N_4O$, 392.13; m/z found, 393.2 [M+H]⁺. ¹H NMR (CD₃OD): 8.83 (s, 1H), 7.91 (d, J=10.7 Hz, 1H), 7.77-7.75 (m, 1H), 7.73-7.70 (m, 1H), 7.54-7.46 (m, 5H), 7.08 (s, 1H), 4.72-4.69 (m, 1H), 4.24 (dd, J=14.3, 7.1 Hz, 1H), 4.11 (dd, J=14.3, 6.6 Hz, 1H).

Example 9

(1R)—N²-[6-(5-Methyl-1-benzothiophen-2-yl)pyrimidin-4-yl]-1-phenylethane-1,2-diamine hydrochloride acid salt

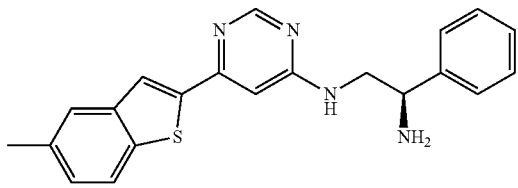 [SMILES: Cc1ccc2sc(-c3cc(NC[C@H](N)c4ccccc4)ncn3)cc2c1]

MS (ESI): mass calcd. for $C_{21}H_{20}N_4S$, 360.14; m/z found, 361.2 [M+H]⁺. ¹H NMR (CD₃OD): 8.75 (s, 1H), 8.12 (s, 1H), 7.87 (d, J=8.2 Hz, 1H), 7.79 (s, 1H), 7.53-7.48 (m, 5H), 7.39 (dd, J=8.2, 1.4 Hz, 1H), 7.03 (s, 1H), 4.70-4.68 (m, 1H), 4.23 (dd, J=14.3, 6.9 Hz, 1H), 4.09 (dd, J=14.3, 6.9 Hz, 1H), 2.49 (s, 3H).

Example 10

(1R)—N²-{6-[4-Ethoxy-3-(trifluoromethyl)phenyl]pyrimidin-4-yl}-1-phenylethane-1,2-diamine hydrochloride acid salt

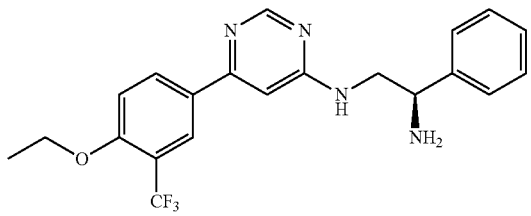 [SMILES: CCOc1ccc(-c2cc(NC[C@H](N)c3ccccc3)ncn2)cc1C(F)(F)F]

MS (ESI): mass calcd. for $C_{21}H_{21}F_3N_4O$, 402.17; m/z found, 403.2 [M+H]⁺. ¹H NMR (CD₃OD): 8.80 (s, 1H), 8.08-8.06 (m, 2H), 7.55-7.43 (m, 6H), 7.06 (s, 1H), 4.73-4.70 (m, 1H), 4.30 (q, J=7.1 Hz, 2H), 4.24 (dd, J=14.0, 6.9 Hz, 1H), 4.13 (dd, J=14.3, 6.6 Hz, 1H), 1.47 (t, J=7.1 Hz, 3H).

Example 11

(1R)-1-Phenyl-N²-(6-{4-[(trifluoromethyl)sulfanyl]phenyl}pyrimidin-4-yl)ethane-1,2-diamine hydrochloride acid salt

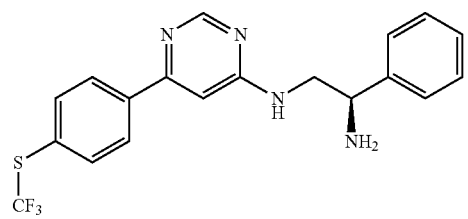 [SMILES: N[C@@H](CNc1cc(-c2ccc(SC(F)(F)F)cc2)ncn1)c1ccccc1]

MS (ESI): mass calcd. for $C_{19}H_{17}F_3N_4S$, 390.11; m/z found, 391.2 [M+H]⁺. ¹H NMR (CD₃OD): 8.84 (s, 1H), 7.95 (s, 4H), 7.55-7.47 (m, 5H), 7.10 (s, 1H), 4.72-4.70 (m, 1H), 4.25 (dd, J=14.3, 7.1 Hz, 1H), 4.12 (dd, J=14.0, 7.1 Hz, 1H).

Example 12

(1R)—N²-{6-[4-(Difluoromethoxy)-3,5-difluorophenyl]pyrimidin-4-yl}-1-phenylethane-1,2-diamine hydrochloride acid salt

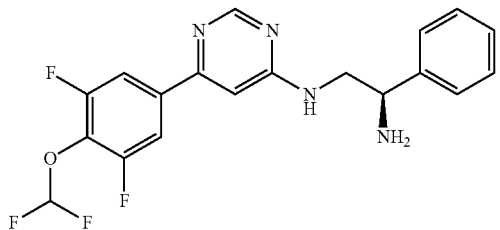 [SMILES: N[C@@H](CNc1cc(-c2cc(F)c(OC(F)F)c(F)c2)ncn1)c1ccccc1]

MS (ESI): mass calcd. for $C_{19}H_{16}F_4N_4O$, 392.13; m/z found, 393.2 [M+H]⁺. ¹H NMR (CD₃OD): 8.83 (s, 1H), 7.70 (d, J=7.7 Hz, 2H), 7.55-7.46 (m, 5H), 7.08 (s, 1H), 7.01 (t, J=72.2 Hz, 1H), 4.72-4.69 (m, 1H), 4.24 (dd, J=14.3, 7.1 Hz, 1H), 4.12 (dd, J=14.0, 6.0 Hz, 1H).

Example 13

(1R)-1-Phenyl-N²-[6-(3-(trifluoromethyl)-benzo[d]isoxazol-6-yl)pyrimidin-4-yl]-ethane-1,2-diamine hydrochloride acid salt

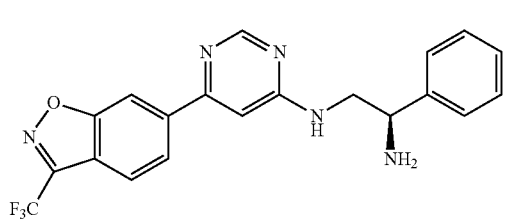 [SMILES: N[C@@H](CNc1cc(-c2ccc3c(C(F)(F)F)noc3c2)ncn1)c1ccccc1]

MS (ESI): mass calcd. for $C_{20}H_{16}F_3N_5O$, 399.13; m/z found, 400.2 [M+H]⁺. ¹H NMR (CD₃OD): 8.91 (s, 1H), 8.38

(s, 1H), 8.19 (d, J=8.3 Hz, 1H), 7.97 (d, J=8.6 Hz, 1H), 7.57-7.50 (m, 5H), 7.21 (s, 1H), 4.77-4.72 (m, 1H), 4.29 (dd, J=14.1, 6.8 Hz, 1H), 4.17 (dd, J=14.4, 7.1 Hz, 1H).

Example 14

(1R)—N²-[6-(4-Chlorophenyl)pyrimidin-4-yl]-1-phenylethane-1,2-diamine hydrochloride acid salt

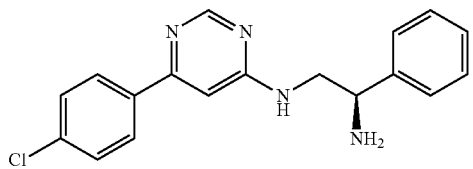 [SMILES: N[C@@H](CNc1cc(-c2ccc(Cl)cc2)ncn1)c1ccccc1]

MS (ESI): mass calcd. for $C_{18}H_{17}ClN_4$, 324.11; m/z found, 325.1 [M+H]⁺. ¹H NMR (CD₃OD): 8.81 (s, 1H), 7.83 (d, J=8.5 Hz, 2H), 7.67 (d, J=8.5 Hz, 2H), 7.54-7.48 (m, 5H), 7.05 (s, 1H), 4.72-4.69 (m, 1H), 4.24 (dd, J=14.2, 6.7 Hz, 1H), 4.11 (dd, J=14.0, 6.6 Hz, 1H).

Example 15

(1R)—N²-[6-(3-Chlorophenyl)pyrimidin-4-yl]-1-phenylethane-1,2-diamine hydrochloride acid salt

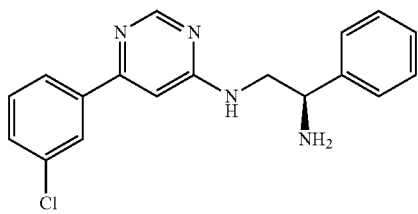 [SMILES: N[C@@H](CNc1cc(-c2cccc(Cl)c2)ncn1)c1ccccc1]

MS (ESI): mass calcd. for $C_{18}H_{17}ClN_4$, 324.11; m/z found, 325.1 [M+H]⁺. ¹H NMR (CD₃OD): 8.82 (s, 1H), 7.89-7.88 (m, 1H), 7.77 (d, J=7.7 Hz, 1H), 7.73-7.69 (m, 1H), 7.63 (t, J=8.0 Hz, 1H), 7.54-7.47 (m, 5H), 7.06 (s, 1H), 4.72-4.69 (m, 1H), 4.24 (dd, J=14.3, 6.7 Hz, 1H), 4.12 (dd, J=13.5, 6.3 Hz, 1H).

Example 16

(1R)—N²-[6-(3,4-Dichlorophenyl)pyrimidin-4-yl]-1-phenylethane-1,2-diamine hydrochloride acid salt

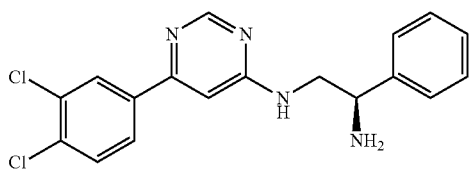 [SMILES: N[C@@H](CNc1cc(-c2ccc(Cl)c(Cl)c2)ncn1)c1ccccc1]

MS (ESI): mass calcd. for $C_{18}H_{16}Cl_2N_4$, 358.08; m/z found, 359.1 [M+H]⁺. ¹H NMR (CD₃OD): 8.82 (s, 1H), 8.06 (d, J=1.9 Hz, 1H), 7.81 (d, J=8.5 Hz, 1H), 7.77-7.75 (m, 1H), 7.54-7.47 (m, 5H), 7.07 (s, 1H), 4.72-4.69 (m, 1H), 4.23 (dd, J=14.3, 7.1 Hz, 1H), 4.12 (dd, J=14.3, 6.7 Hz, 1H).

Example 17

(1R)—N²-{6-[4-Chloro-3-(trifluoromethyl)phenyl]pyrimidin-4-yl}-1-phenylethane-1,2-diamine hydrochloride acid salt

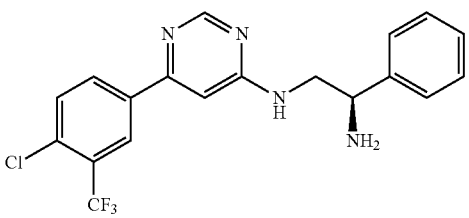 [SMILES: N[C@@H](CNc1cc(-c2ccc(Cl)c(C(F)(F)F)c2)ncn1)c1ccccc1]

MS (ESI): mass calcd. for $C_{19}H_{16}ClF_3N_4$, 392.10; m/z found, 393.1 [M+H]⁺. ¹H NMR (CD₃OD): 8.84 (s, 1H), 8.25 (d, J=2.2 Hz, 1H), 8.08-8.06 (m, 1H), 7.91 (d, J=8.2 Hz, 1H), 7.54-7.47 (m, 5H), 7.10 (s, 1H), 4.72-4.69 (m, 1H), 4.25 (dd, J=14.0, 6.9 Hz, 1H), 4.12 (dd, J=14.0, 6.9 Hz, 1H).

Example 18

(1R)-1-Phenyl-N²-{6-[3-(trifluoromethoxy)phenyl]pyrimidin-4-yl}ethane-1,2-diamine hydrochloride acid salt

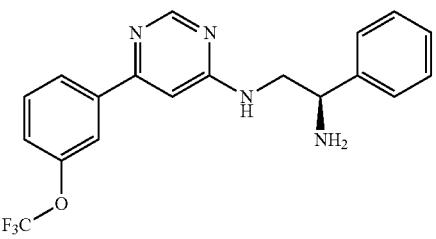 [SMILES: N[C@@H](CNc1cc(-c2cccc(OC(F)(F)F)c2)ncn1)c1ccccc1]

MS (ESI): mass calcd. for $C_{19}H_{17}F_3N_4O$, 374.14; m/z found, 375.2 [M+H]⁺. ¹H NMR (CD₃OD): 8.84 (s, 1H), 7.84 (d, J=7.7 Hz, 1H), 7.78-7.74 (m, 2H), 7.64 (d, J=8.2 Hz, 1H), 7.55-7.47 (m, 5H), 7.10 (s, 1H), 4.73-4.70 (m, 1H), 4.25 (dd, J=14.3, 7.1 Hz, 1H), 4.13 (dd, J=14.0, 7.1 Hz, 1H).

Example 19

(1R)—N²-[6-(4-Ethoxyphenyl)pyrimidin-4-yl]-1-phenylethane-1,2-diamine hydrochloride acid salt

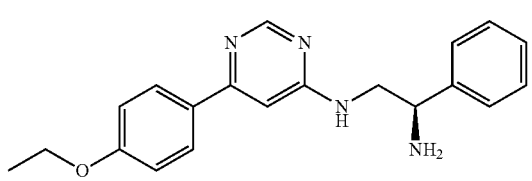 [SMILES: CCOc1ccc(-c2cc(NC[C@H](N)c3ccccc3)ncn2)cc1]

MS (ESI): mass calcd. for $C_{20}H_{22}N_4O$, 334.18; m/z found, 335.2 [M+H]⁺. ¹H NMR (CD₃OD): 8.76 (s, 1H), 7.80 (d, J=8.5 Hz, 2H), 7.54-7.47 (m, 5H), 7.15 (d, J=9.1 Hz, 2H), 6.99 (s, 1H), 4.71-4.68 (m, 1H), 4.23 (dd, J=14.3, 6.7 Hz, 1H), 4.15 (q, J=7.1 Hz, 2H), 4.10 (dd, J=14.3, 6.6 Hz, 1H), 1.43 (t, J=7.1 Hz, 3H).

Example 20

(1R)-1-Phenyl-$N^2$-{6-[4-(2,2,2-trifluoroethoxy)phenyl]pyrimidin-4-yl}ethane-1,2-diamine hydrochloride acid salt

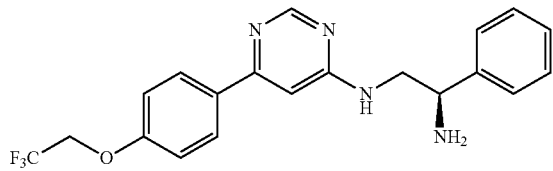 [SMILES: N[C@@H](CNc1cc(-c2ccc(OCC(F)(F)F)cc2)ncn1)c1ccccc1]

MS (ESI): mass calcd. for $C_{20}H_{19}F_3N_4O$, 388.15; m/z found, 389.2 [M+H]$^+$. $^1$H NMR (CD$_3$OD): 8.78 (s, 1H), 7.85 (d, J=8.8 Hz, 2H), 7.54-7.47 (m, 5H), 7.28 (d, J=9.1 Hz, 2H), 7.01 (s, 1H), 4.72-4.67 (m, 3H), 4.23 (dd, J=14.0, 7.1 Hz, 1H), 4.10 (dd, J=14.0, 6.9 Hz, 1H).

Example 21

(1R)—$N^2$-{6-[3-Fluoro-4-(2,2,2-trifluoroethoxy)phenyl]pyrimidin-4-yl}-1-phenylethane-1,2-diamine hydrochloride acid salt

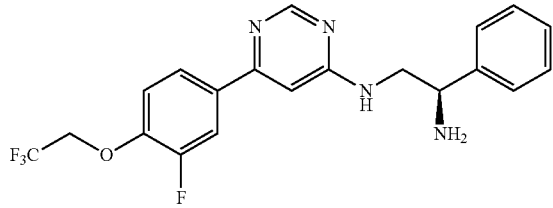 [SMILES: N[C@@H](CNc1cc(-c2ccc(OCC(F)(F)F)c(F)c2)ncn1)c1ccccc1]

MS (ESI): mass calcd. for $C_{20}H_{18}F_4N_4O$, 406.14; m/z found, 407.2 [M+H]$^+$. $^1$H NMR (CD$_3$OD): 8.79 (s, 1H), 7.73 (d, J=11.0 Hz, 1H), 7.69 (d, J=8.2 Hz, 1H), 7.54-7.44 (m, 6H), 7.04 (s, 1H), 4.79 (q, J=8.2 Hz, 2H), 4.72-4.69 (m, 1H), 4.24 (dd, J=14.3, 7.1 Hz, 1H), 4.11 (dd, J=14.3, 7.1 Hz, 1H).

Example 22

(1R)—$N^2$-{6-[4-(Ethylsulfanyl)phenyl]pyrimidin-4-yl}-1-phenylethane-1,2-diamine hydrochloride acid salt

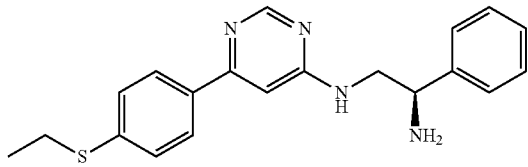

MS (ESI): mass calcd. for $C_{20}H_{22}N_4S$, 350.16; m/z found, 351.2 [M+H]$^+$. $^1$H NMR (CD$_3$OD): 8.78 (s, 1H), 7.75 (d, J=8.5 Hz, 2H), 7.54-7.47 (m, 7H), 7.03 (s, 1H), 4.71-4.68 (m, 1H), 4.24 (dd, J=14.3, 7.1 Hz, 1H), 4.11 (m, J=14.5, 7.1 Hz, 1H), 3.10 (q, J=7.4 Hz, 2H), 1.37 (t, J=7.4 Hz, 3H).

Example 23

4-(6-{[(2R)-2-Amino-2-phenylethyl]amino}pyrimidin-4-yl)-N,N-dimethylbenzenesulfonamide hydrochloride acid salt

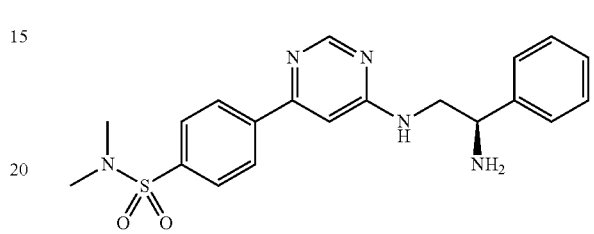

MS (ESI): mass calcd. for $C_{20}H_{23}N_5O_2S$, 397.16; m/z found, 398.2 [M+H]$^+$. $^1$H NMR (CD$_3$OD): 8.87 (s, 1H), 8.07-8.01 (m, 4H), 7.56-7.46 (m, 5H), 7.15 (s, 1H), 4.74-4.72 (m, 1H), 4.27 (dd, J=14.3, 6.9 Hz, 1H), 4.14 (dd, J=14.3, 6.9 Hz, 1H), 2.75 (s, 6H).

Example 24

(1R)—$N^2$-[6-(2,2-Difluoro-1,3-benzodioxol-5-yl)pyrimidin-4-yl]-1-phenylethane-1,2-diamine hydrochloride acid salt

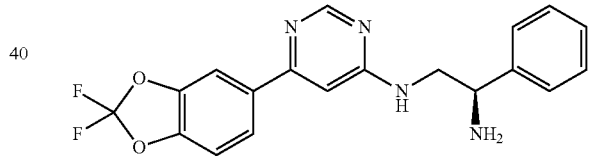

The title compound was prepared using methods analogous to those described in Example 4 with the following modifications performed in step B.

Step B: tert-Butyl[(1R)-2-({6-[2,2-difluoro-1,3-benzodioxo-5-yl]pyrimidin-4-yl}amino)-1-phenylethyl]carbamate. [2-(6-Chloro-pyrimidin-4-ylamino)-1-phenyl-ethyl]-carbamic acid tert-butyl ester (87.2 mg, 0.25 mmol), 2,2-difluoro-5-(4,4,5,5-tetramethyl-[1,3,2]dioxaborolan-2-yl)-benzo[1,3]dioxole (71.0 mg, 0.25 mmol), Pd(OAc)$_2$ (1.1 mg, 0.005 mmol), 2-dicyclohexylphosphino-2',6'-dimethoxy-1,1'-biphenyl (S-Phos) (4.1 mg, 0.01 mmol) and K$_3$PO$_4$ (159 mg, 0.75 mmol) were dissolved in 1,4-dioxane (2.0 mL) and water (0.2 mL) in a microwave tube. The tube was evacuated and refilled with N$_2$ and heated at 90° C. overnight. The reaction mixture was cooled to rt and filtered through a pad of MgSO$_4$. The pad was washed with CH$_2$Cl$_2$ and the filtrate was concentrated under reduced pressure. The crude residue was purified (FCC) to yield the desired product (81 mg, 69%).

Step C: (1R)—$N^2$-[6-(2,2-Difluoro-1,3-benzodioxol-5-yl)pyrimidin-4-yl]-1-phenylethane-1,2-diamine. MS (ESI): mass calcd. for $C_{19}H_{16}F_2N_4O_2$, 370.12; m/z found, 371.2 [M+H]$^+$. $^1$H NMR (CD$_3$OD): 8.83 (s, 1H), 7.74 (s, 1H), 7.68

(d, J=8.8 Hz, 1H), 7.55-7.47 (m, 6H), 7.04 (s, 1H), 4.72-4.70 (m, 1H), 4.25 (dd, J=14.3, 6.9 Hz, 1H), 4.13 (dd, J=14.3, 6.9 Hz, 1H).

Example 25 was prepared using methods analogous to those described in Example 24.

Example 25

(1R)-1-Phenyl-N$^2$-{6-[5-(trifluoromethoxy)-1-benzothiophen-2-yl]pyrimidin-4-yl}ethane-1,2-diamine hydrochloride acid salt

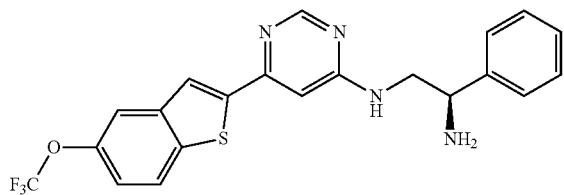 [SMILES: N[C@@H](CNc1cc(-c2cc3cc(OC(F)(F)F)ccc3s2)ncn1)c1ccccc1]

MS (ESI): mass calcd. for $C_{21}H_{17}F_3N_4OS$, 430.11; m/z found, 431.1 [M+H]$^+$. $^1$H NMR (CD$_3$OD): 8.79 (s, 1H), 8.22 (s, 1H), 8.11 (d, J=8.8 Hz, 1H), 7.94 (s, 1H), 7.53-7.46 (m, 6H), 7.09 (s, 1H), 4.72-4.69 (m, 1H), 4.24 (dd, J=14.0, 7.1 Hz, 1H), 4.10 (dd, J=14.3, 7.1 Hz, 1H).

Example 26

N-[(1R)-2-({6-[3-chloro-4-(trifluoromethyl)phenyl]pyrimidin-4-yl}amino)-1-phenylethyl]-2,2,2-trifluoroacetamide

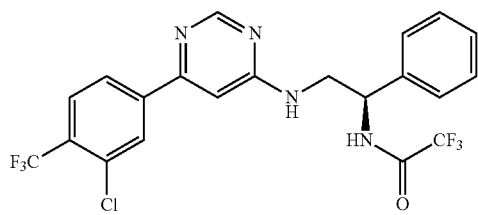 [SMILES: O=C(N[C@@H](CNc1cc(-c2ccc(C(F)(F)F)c(Cl)c2)ncn1)c1ccccc1)C(F)(F)F]

To a solution of (1R)—N$^2$-{6-[3-chloro-4-(trifluoromethyl)phenyl]pyrimidin-4-yl}-1-phenylethane-1,2-diamine (215 mg, 0.50 mmol) in anhydrous THF (4 mL) and triethylamine (0.15 mL, 1.1 mmol) at 0° C. was added dropwise a solution of trifluoroacetic anhydride (0.10 mL, 0.75 mmol) in anhydrous THF (0.15 mL). The reaction was stirred for 2.5 h. and then diluted with water (20 mL) and EtOAc (20 mL). The layers were separated and the organic layer was washed with a 2 N aq. HCl (10 mL), followed by brine (10 mL), dried (MgSO$_4$) and concentrated under reduced pressure. The reaction mixture was purified (FCC) to yield the title compound (173 mg, 71%). MS (ESI): mass calcd. for $C_{21}H_{15}ClF_6N_4O$, 488.08; m/z found, 489.1 [M+H]$^+$. $^1$H NMR (CDCl$_3$): 8.73 (d, J=0.8 Hz, 1H), 8.14 (s, 1H), 7.94 (d, J=7.6 Hz, 1H), 7.79 (d, J=8.3 Hz, 1H), 7.41-7.37 (m, 2H), 7.35-7.28 (m, 3H), 6.79 (s, 1H), 5.27-5.18 (br s, 1H), 5.14-5.10 (m, 1H), 4.01-3.93 (m, 1H), 3.87 (ddd, J=14.7, 6.1, 3.3 Hz, 1H).

Example 27

(1R)—N$^2$-[6-(3-Chloro-4-trifluoromethyl-phenyl)-pyrimidin-4-yl]-1-(4-fluoro-phenyl)-ethane-1,2-diamine

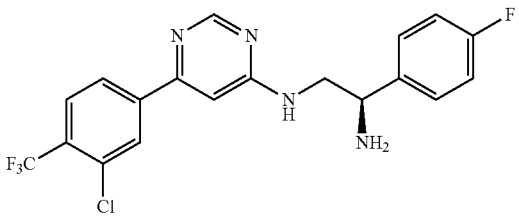 [SMILES: N[C@@H](CNc1cc(-c2ccc(C(F)(F)F)c(Cl)c2)ncn1)c1ccc(F)cc1]

Step A: (1R)-2-Methyl-propane-2-sulfinic acid 4-fluoro-benzylideneamide. To a solution consisting of 4-fluorobenzaldehyde (0.69 mL, 8.06 mmol), (1R)-2-methyl-propane-2-sulfinic acid amide (1.08 g, 8.89 mmol) and THF (90 mL) was added Ti(OEt)$_4$ (3.4 mL, 16.1 mmol). The reaction mixture was stirred for 16 h at rt. NaCl (sat. aq., 100 mL) was added to the reaction mixture and a white solid precipitated. The mixture was diluted with H$_2$O (500 mL) and filtered through a pad of Celite®. The resultant filtrate was extracted with EtOAc (100 mL) and washed with sat. aq. NaCl (2×100 mL). The organic layer was separated, dried (MgSO$_4$), and concentrated under reduced pressure. The crude residue was purified (FCC) to give the title compound as a pale yellow oil (1.57 g, 85%). MS (ESI$^+$): calcd for $C_{11}H_{14}FNOS$ m/z 227.08. found 228.1 (M+H)$^+$. $^1$H NMR (CDCl$_3$): 8.55 (s, 1H), 7.87 (dd, J=8.8, 5.5, 2H), 7.17 (t, J=8.6, 2H), 1.27 (s, 9H).

Step B: (R,R)-2-Methyl-propane-2-sulfinic acid [1-(4-fluoro-phenyl)-2-nitro-ethyl]-amide. To a cooled mixture of nitromethane (2.19 mL, 40.7 mmol) and THF (30 mL at 0° C. was added t-BuOK (1 M in THF, 8.14 mL) dropwise. A white precipitate formed. Stirring was continued for 10 min at 0° C. and then a solution of (1R)-2-methyl-propane-2-sulfinic acid 4-fluoro-benzylideneamide (0.925 g, 4.07 mmol) in THF (10 mL) was added dropwise. The reaction was stirred for an additional 10 min at 0° C. before slowly warming to rt overnight. After 16 h, glacial acetic acid (2 mL) was added to the reaction mixture which lowered the pH to 5. The mixture was then washed with brine (2×100 mL). The organic layer was dried (MgSO$_4$), filtered and concentrated under reduced pressure. The crude residue was purified (FCC) providing (R,S)-2-methyl-propane-2-sulfinic acid [1-(4-fluoro-phenyl)-2-nitro-ethyl]-amide (59 mg, 5%) and (R,R)-2-methyl-propane-2-sulfinic acid [1-(4-fluoro-phenyl)-2-nitro-ethyl]-amide (669 mg, 57%) respectively. MS (ESI$^+$): calcd for $C_{12}H_{17}FN_2O_3S$ m/z 288.09. found 289.1 (M+H)$^+$. $^1$H NMR (CDCl$_3$): 7.35 (dd, J=8.7, 5.2 Hz, 2H), 7.07 (t, J=8.6 Hz, 2H), 5.11-5.06 (m, 1H), 4.85 (dd, J=13.3, 7.5 Hz, 1H), 4.75 (dd, J=13.3, 5.0 Hz, 1H), 4.58 (d, J=5.2 Hz, 1H), 1.22 (s, 9H).

Step C: (R,R)-2-Methyl-propane-2-sulfinic acid [2-amino-1-(4-fluoro-phenyl)-ethyl]-amide. Zn powder (5.07 g, 77.6 mmol) was added to a solution of (R,R)-2-methyl-propane-2-sulfinic acid [1-(4-fluoro-phenyl)-2-nitro-ethyl]-amide (2.24 g, 7.76 mmol) and NH$_4$Cl (4.15 g, 77.6 mmol) in 5:1 acetone/H$_2$O (24 mL) at rt. After 10 min, the reaction mixture was filtered and the filtrate concentrated under reduced pressure. The crude residue was crystallized using CH$_2$Cl$_2$ (20 mL) and hexanes (50 mL) to provide (R,R)-2-methyl-propane-2-sulfinic acid [2-amino-1-(4-fluoro-phenyl)-ethyl]-amide (1.8 g, 89%). MS (ESI+): calcd for $C_{12}H_{19}FN_2OS$ m/z 258.12. found 259.1 (M+H)+.

Step D: (R,R)-2-Methyl-propane-2-sulfinic acid [2-[6-(3-chloro-4-trifluoromethyl-phenyl)-pyrimidin-4-ylamino]-1-(4-fluoro-phenyl)-ethyl]-amide. A solution of 4-chloro-6-(3-chloro-4-trifluoromethyl-phenyl)-pyrimidine (0.200 g, 0.68 mmol), (R,R)-2-methyl-propane-2-sulfinic acid [2-amino-1-(4-fluoro-phenyl)-ethyl]-amide (0.720 g, 2.79 mmol) and DIPEA (0.18 mL, 1.02 mmol) in DMF (5 mL) was heated at 80° C. for 16 h. The reaction mixture was cooled to rt, diluted with EtOAc (20 mL) and washed with NaCl (sat. aq., 2×30 mL). The organic layer was dried (MgSO4) and concentrated under reduced pressure. The crude residue was purified (FCC) to give the title compound (0.172 g, 50%) as a yellow solid. MS (ESI+): calcd for $C_{23}H_{23}ClF_4N_4OS$ m/z 514.12. found 515.1 (M+H)+.

Step E: (1R)—$N^2$-[6-(3-Chloro-4-trifluoromethyl-phenyl)-pyrimidin-4-yl]-1-(4-fluoro-phenyl)-ethane-1,2-diamine. A solution of (R,R)-2-methyl-propane-2-sulfinic acid [2-[6-(3-chloro-4-trifluoromethyl-phenyl)-pyrimidin-4-ylamino]-1-(4-fluoro-phenyl)-ethyl]-amide (0.172 g, 0.337 mmol) in MeOH (5 mL) was added HCl (4 N in dioxane, 0.34 mL) at rt. After 30 min, the reaction mixture was purified directly via reverse phase chromatography. The desired fractions were then free-based by washing with sat. aq. NaHCO3 (2×30 mL) and extracting with EtOAc (2×25 mL). The organic layers were combined, dried (MgSO4), filtered and concentrated under reduced pressure to give the title compound (75 mg, 54%) as a white solid. MS (ESI+): calcd for $C_{19}H_{15}ClF_4N_4$ m/z 410.09. found 411.1 (M+H)+. $^1$H NMR (CDCl3): 8.60 (s, 1H), 8.05 (s, 1H), 7.86 (d, J=8.2 Hz, 1H), 7.73 (d, J=8.3 Hz, 1H), 7.35 (dd, J=8.6, 5.3 Hz, 2H), 7.05 (t, J=8.6 Hz, 2H), 6.66 (s, 1H), 5.89 (s, 1H), 4.27 (s, 1H), 3.76-3.64 (m, 1H), 3.59-3.50 (m, 1H), 3.03-2.85 (m, 2H).

Examples 28 to 65 were prepared using methods analogous to those described for Example 27, using the appropriate commercially available aldehyde.

Example 28

(1S)—$N^2$-[6-(3-Chloro-4-trifluoromethyl-phenyl)-pyrimidin-4-yl]-1-(4-fluoro-phenyl)-ethane-1,2-diamine

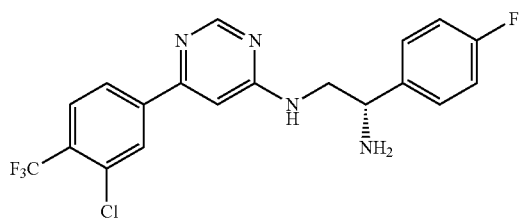 [SMILES: N[C@H](CNc1cc(-c2ccc(C(F)(F)F)c(Cl)c2)ncn1)c1ccc(F)cc1]

MS (ESI+): calcd for $C_{19}H_{15}ClF_4N_4$ m/z 410.09. found 411.1 (M+H)+. $^1$H NMR (CDCl3): 8.65 (s, 1H), 8.10 (s, 1H), 7.91 (d, J=8.3 Hz, 1H), 7.76 (d, J=8.2 Hz, 1H), 7.36 (dd, J=8.7, 5.3 Hz, 2H), 7.06 (t, J=8.7 Hz, 2H), 6.68 (s, 1H), 5.55 (s, 1H), 4.28-4.20 (m, 1H), 3.75-3.62 (m, 1H), 3.56-3.51 (m, 1H), 1.71-1.60 (m, 2H).

Example 29

(1S)—$N^2$-[6-(3-Chloro-4-trifluoromethyl-phenyl)-pyrimidin-4-yl]-1-(4-trifluoromethyl-phenyl)-ethane-1,2-diamine

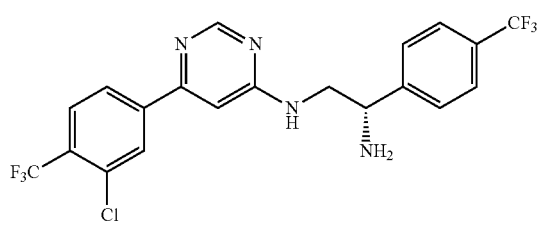 [SMILES: N[C@H](CNc1cc(-c2ccc(C(F)(F)F)c(Cl)c2)ncn1)c1ccc(C(F)(F)F)cc1]

MS (ESI+): calcd for $C_{20}H_{15}ClF_6N_4$ m/z 460.09. found 461.1 (M+H)+. $^1$H NMR (CDCl3): 8.62 (s, 1H), 8.05 (s, 1H), 7.86 (d, J=7.5 Hz, 1H), 7.73 (d, J=8.3 Hz, 1H), 7.62 (d, J=8.1 Hz, 2H), 7.52 (d, J=8.1 Hz, 2H), 6.67 (s, 1H), 5.83 (s, 1H), 4.41 (s, 1H), 4.07 (s, 2H), 3.84-3.75 (m, 1H), 3.65-3.55 (m, 1H).

Example 30

(1R)—$N^2$-[6-(3-Chloro-4-trifluoromethyl-phenyl)-pyrimidin-4-yl]-1-(4-trifluoromethyl-phenyl)-ethane-1,2-diamine

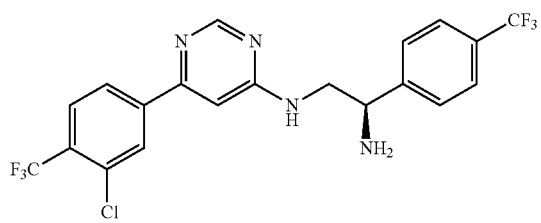 [SMILES: N[C@@H](CNc1cc(-c2ccc(C(F)(F)F)c(Cl)c2)ncn1)c1ccc(C(F)(F)F)cc1]

MS (ESI+): calcd for $C_{20}H_{15}ClF_6N_4$ m/z 460.09. found 461.1 (M+H)+. $^1$H NMR (CDCl3): 8.61 (s, 1H), 8.04 (s, 1H), 7.84 (d, J=8.2 Hz, 1H), 7.73 (d, J=8.3 Hz, 1H), 7.62 (d, J=8.2 Hz, 2H), 7.51 (d, J=8.1 Hz, 2H), 6.66 (s, 1H), 5.88 (s, 1H), 4.53-4.31 (m, 3H), 3.87-3.73 (m, 1H), 3.66-3.55 (m, 1H).

Example 31

(1S)—$N^2$-[6-(3-Chloro-4-trifluoromethyl-phenyl)-pyrimidin-4-yl]-1-(2,2-difluoro-benzo[1,3]dioxol-5-yl)-ethane-1,2-diamine

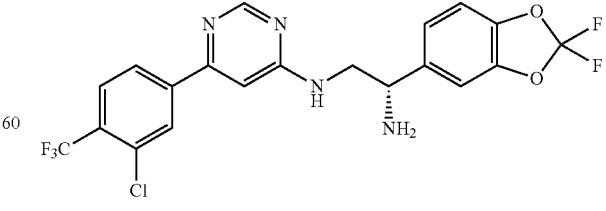

MS (ESI+): calcd for $C_{20}H_{14}ClF_5N_4O_2$ m/z 472.07. found 473.1 (M+H)+. $^1$H NMR (CDCl3): 8.65 (s, 1H), 8.09 (s, 1H), 7.90 (d, J=8.2 Hz, 1H), 7.75 (d, J=8.3 Hz, 1H), 7.16 (s, 1H), 7.09 (d, J=8.2 Hz, 1H), 7.03 (d, J=8.1 Hz, 1H), 6.69 (s, 1H), 5.57 (s, 1H), 4.31 (s, 1H), 3.79-3.62 (m, 1H), 3.60-3.48 (m, 1H), 2.78-2.20 (m, 2H).

Example 32

(1R)—N²-[6-(3-Chloro-4-trifluoromethyl-phenyl)-pyrimidin-4-yl]-1-(2,2-difluoro-benzo[1,3]dioxol-5-yl)-ethane-1,2-diamine

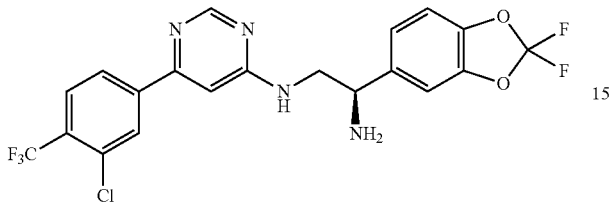

MS (ESI⁺): calcd for $C_{20}H_{14}ClF_5N_4O_2$ m/z 472.07. found 473.1 (M+H)⁺. ¹H NMR (CDCl₃): 8.58 (s, 1H), 8.01 (s, 1H), 7.82 (d, J=8.6 Hz, 1H), 7.71 (d, J=8.3 Hz, 1H), 7.16 (s, 1H), 7.09 (d, J=7.2 Hz, 1H), 7.01 (d, J=8.2 Hz, 1H), 6.66 (s, 1H), 6.00 (s, 1H), 5.57-5.28 (m, 2H), 4.40 (s, 1H), 3.84-3.73 (m, 1H), 3.68-3.57 (m, 1H).

Example 33

(1S)-4-{1-Amino-2-[6-(3-chloro-4-trifluoromethyl-phenyl)-pyrimidin-4-ylamino]-ethyl}-benzonitrile

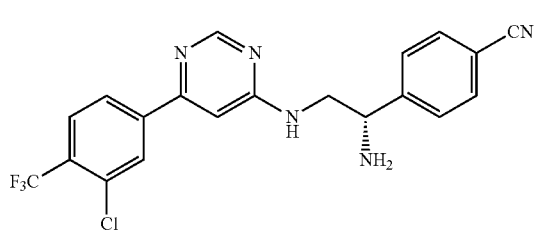 [SMILES: N#Cc1ccc([C@H](N)CNc2cc(-c3ccc(C(F)(F)F)c(Cl)c3)ncn2)cc1]

MS (ESI⁺): calcd for $C_{20}H_{15}ClF_3N_5$ m/z 417.10. found 418.1 (M+H)⁺. ¹H NMR (CDCl₃): 8.65 (s, 1H), 8.10 (s, 1H), 7.92 (d, J=8.2, 1H), 7.76 (d, J=8.3, 1H), 7.65 (d, J=8.5, 2H), 7.54 (d, J=8.3, 2H), 6.72 (s, 1H), 5.61 (s, 1H), 4.35 (s, 1H), 3.79-3.70 (m, 1H), 3.59-3.47 (m, 1H), 1.76-1.60 (m, 2H).

Example 34

(1R)-4-{1-Amino-2-[6-(3-chloro-4-trifluoromethyl-phenyl)-pyrimidin-4-ylamino]-ethyl}-benzonitrile

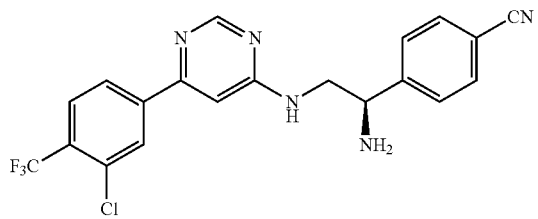 [SMILES: N#Cc1ccc([C@@H](N)CNc2cc(-c3ccc(C(F)(F)F)c(Cl)c3)ncn2)cc1]

MS (ESI⁺): calcd for $C_{20}H_{15}ClF_3N_5$ m/z 417.10. found 418.1 (M+H)⁺. ¹H NMR (CDCl₃): 8.66 (s, 1H), 8.10 (s, 1H), 7.92 (d, J=9.0 Hz, 1H), 7.76 (d, J=8.3 Hz, 1H), 7.65 (d, J=8.4 Hz, 2H), 7.54 (d, J=8.2 Hz, 2H), 6.72 (d, J=1.0 Hz, 1H), 5.62-5.52 (m, 1H), 4.39-4.30 (m, 1H), 3.79-3.71 (m, 1H), 3.58-3.49 (m, 1H), 1.76-1.58 (m, 2H).

Example 35

N²-[6-(3-Chloro-4-trifluoromethyl-phenyl)-pyrimidin-4-yl]-1-(2-fluoro-phenyl)-ethane-1,2-diamine

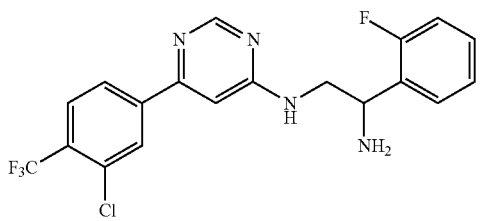 [SMILES: NC(CNc1cc(-c2ccc(C(F)(F)F)c(Cl)c2)ncn1)c1ccccc1F]

MS (ESI⁺): calcd for $C_{19}H_{15}ClF_4N_4$ m/z 410.09. found 411.1 (M+H)⁺. ¹H NMR (CDCl₃): 8.64 (s, 1H), 8.12 (s, 1H), 7.93 (d, J=8.1 Hz, 1H), 7.77 (d, J=8.2 Hz, 1H), 7.43 (t, J=7.0 Hz, 1H), 7.32-7.26 (m, 1H), 7.16 (t, J=7.1 Hz, 1H), 7.11-7.04 (m, 1H), 6.74 (s, 1H), 5.70 (s, 1H), 4.49 (s, 1H), 3.83-3.72 (m, 1H), 3.63-3.50 (m, 1H), 2.23-1.90 (m, 2H).

Example 36

(1S)—N²-[6-(3-Chloro-4-trifluoromethyl-phenyl)-pyrimidin-4-yl]-1-(3-fluoro-phenyl)-ethane-1,2-diamine, trifluoroacetic acid salt

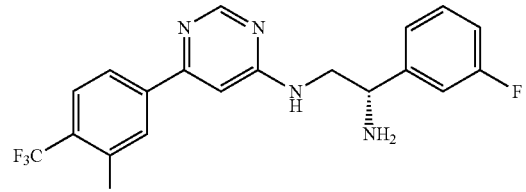

MS (ESI⁺): calcd for $C_{19}H_{15}ClF_4N_4$ m/z 410.09. found 411.1 (M+H)⁺. ¹H NMR (d₆-DMSO): 8.67-8.55 (m, 3H), 8.28 (s, 1H), 8.17-8.09 (m, 1H), 8.00 (d, J=8.4 Hz, 1H), 7.75 (s, 1H), 7.50 (dd, J=14.1, 8.0 Hz, 1H), 7.41 (d, J=10.0 Hz, 1H), 7.34 (d, J=7.8 Hz, 1H), 7.29-7.22 (m, 1H), 7.13 (s, 1H), 4.61 (s, 1H), 3.96-3.76 (m, 2H).

Example 37

(1R)—N²-[6-(3-Chloro-4-trifluoromethyl-phenyl)-pyrimidin-4-yl]-1-(3-fluoro-phenyl)-ethane-1,2-diamine, trifluoroacetic acid salt

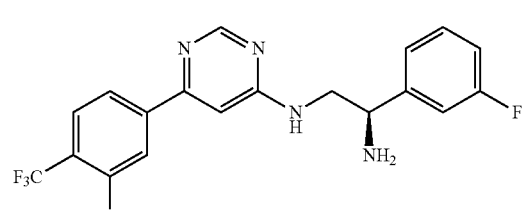

MS (ESI⁺): calcd for $C_{19}H_{15}ClF_4N_4$ m/z 410.09. found 411.1 (M+H)⁺. ¹H NMR (d₆-DMSO): 8.63 (s, 1H), 8.57 (s, 2H), 8.28 (s, 1H), 8.17-8.09 (m, 1H), 8.00 (d, J=8.3 Hz, 1H), 7.73 (s, 1H), 7.50 (dd, J=14.2, 7.9 Hz, 1H), 7.40 (d, J=9.9 Hz, 1H), 7.33 (d, J=7.6 Hz, 1H), 7.29-7.21 (m, 1H), 7.13 (s, 1H), 4.61 (s, 1H), 3.96-3.88 (m, 2H).

Example 38

(1S)—N$^2$-1-(4-Chloro-phenyl)-[6-(3-chloro-4-trifluoromethyl-phenyl)-pyrimidin-4-yl]-ethane-1,2-diamine, trifluoroacetic acid salt

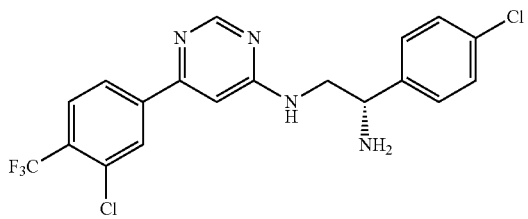 [SMILES: N[C@H](CNc1cc(-c2ccc(C(F)(F)F)c(Cl)c2)ncn1)c1ccc(Cl)cc1]

MS (ESI$^+$): calcd for $C_{19}H_{15}Cl_2F_3N_4$ m/z 426.06. found 427.1 (M+H)$^+$. $^1$H NMR (d$_6$-DMSO): 8.63 (s, 1H), 8.54 (s, 2H), 8.27 (s, 1H), 8.16-8.09 (m, 1H), 8.00 (d, J=8.4 Hz, 1H), 7.75-7.67 (m, 1H), 7.53 (s, 4H), 7.11 (d, J=1.0 Hz, 1H), 4.59 (s, 1H), 3.95-3.86 (m, 1H), 3.83-3.73 (m, 1H).

Example 39

(1R)—N$^2$-1-(4-Chloro-phenyl)-[6-(3-chloro-4-trifluoromethyl-phenyl)-pyrimidin-4-yl]-ethane-1,2-diamine, trifluoroacetic acid salt

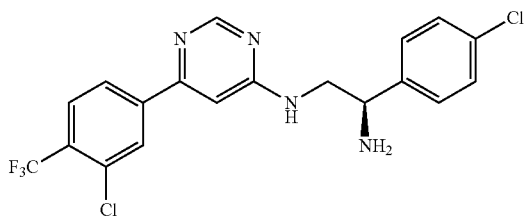 [SMILES: N[C@@H](CNc1cc(-c2ccc(C(F)(F)F)c(Cl)c2)ncn1)c1ccc(Cl)cc1]

MS (ESI$^+$): calcd for $C_{19}H_{15}Cl_2F_3N_4$ m/z 426.06. found 427.1 (M+H)$^+$. $^1$H NMR (d$_6$-DMSO): 8.63 (s, 1H), 8.54 (s, 2H), 8.27 (s, 1H), 8.16-8.09 (m, 1H), 8.00 (d, J=8.4 Hz, 1H), 7.75-7.67 (m, 1H), 7.53 (s, 4H), 7.11 (d, J=1.0 Hz, 1H), 4.59 (s, 1H), 3.95-3.86 (m, 1H), 3.83-3.73 (m, 1H).

Example 40

(1S)—N$^2$-[6-(3-Chloro-4-trifluoromethyl-phenyl)-pyrimidin-4-yl]-1-(3,4-difluoro-phenyl)-ethane-1,2-diamine, trifluoroacetic acid salt

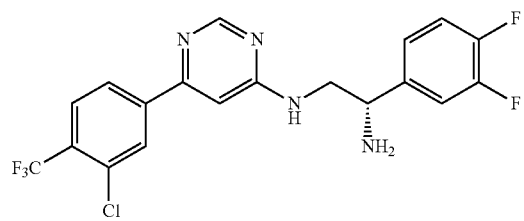

MS (ESI$^+$): calcd for $C_{19}H_{14}ClF_5N_4$ m/z 428.08. found 429.1 (M+H)$^+$. $^1$H NMR (d$_6$-DMSO): 8.63 (s, 1H), 8.26 (d, J=9.0 Hz, 1H), 8.10 (d, J=9.4 Hz, 1H), 8.00 (d, J=8.3 Hz, 1H), 7.74-7.58 (m, 2H), 7.58 (s, 1H), 7.36 (s, 1H), 7.12 (s, 1H), 4.60 (s, 1H), 3.98-3.89 (m, 2H).

Example 41

(1R)—N$^2$-[6-(3-Chloro-4-trifluoromethyl-phenyl)-pyrimidin-4-yl]-1-(3,4-difluoro-phenyl)-ethane-1,2-diamine, trifluoroacetic acid salt

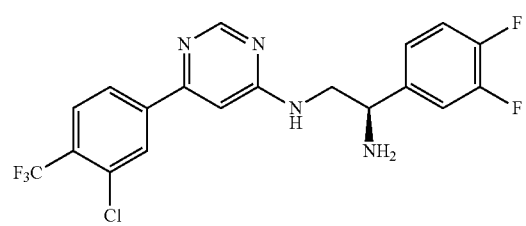 [SMILES: N[C@@H](CNc1cc(-c2ccc(C(F)(F)F)c(Cl)c2)ncn1)c1ccc(F)c(F)c1]

MS (ESI$^+$): calcd for $C_{19}H_{14}ClF_5N_4$ m/z 428.08. found 429.1 (M+H)$^+$. $^1$H NMR (d$_6$-DMSO): 8.63 (s, 1H), 8.28 (s, 1H), 8.12 (s, 1H), 8.00 (d, J=8.3 Hz, 1H), 7.77 (s, 1H), 7.70-7.61 (m, 1H), 7.53 (dt, J=10.6, 8.5 Hz, 1H), 7.36 (d, J=8.5 Hz, 1H), 7.14 (d, J=7.3 Hz, 1H), 4.60 (s, 1H), 3.94 (dt, J=12.8, 6.3 Hz, 1H), 3.88-3.75 (m, 1H).

Example 42

(1S)—N$^2$-[6-(3-Chloro-4-trifluoromethyl-phenyl)-pyrimidin-4-yl]-1-(3,4-dichloro-phenyl)-ethane-1,2-diamine

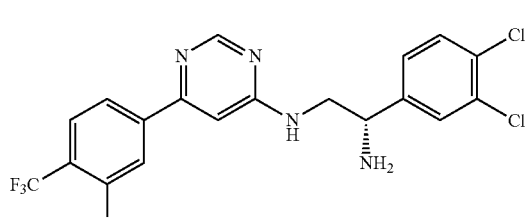

MS (ESI$^+$): calcd for $C_{19}H_{14}Cl_3F_3N_4$ m/z 460.02. found 461.0 (M+H)$^+$. $^1$H NMR (CDCl$_3$): 8.66 (s, 1H), 8.11 (s, 1H), 7.92 (d, J=8.2 Hz, 1H), 7.77 (d, J=8.3 Hz, 1H), 7.52 (d, J=2.0 Hz, 1H), 7.43 (d, J=8.3 Hz, 1H), 7.23 (dd, J=8.3, 2.0 Hz, 1H), 6.70 (s, 1H), 5.49 (s, 1H), 4.24 (dd, J=7.1, 5.5 Hz, 1H), 3.76-3.64 (m, 1H), 3.58-3.45 (m, 1H), 1.57 (s, 2H).

Example 43

(1R)—N$^2$-[6-(3-Chloro-4-trifluoromethyl-phenyl)-pyrimidin-4-yl]-1-(3,4-dichloro-phenyl)-ethane-1,2-diamine

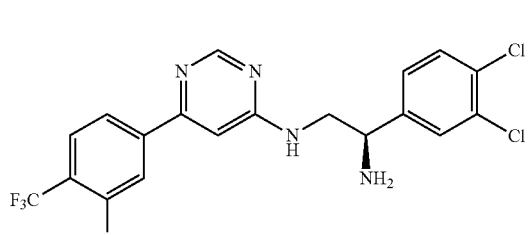

MS (ESI$^+$): calcd for $C_{19}H_{14}Cl_3F_3N_4$ m/z 460.02. found 461.0 (M+H)$^+$. $^1$H NMR (CDCl$_3$): 8.66 (s, 1H), 8.11 (s, 1H), 7.91 (d, J=8.2 Hz, 1H), 7.76 (d, J=8.3 Hz, 1H), 7.52 (d, J=2.0

Hz, 1H), 7.43 (d, J=8.3 Hz, 1H), 7.23 (dd, J=8.3, 2.0 Hz, 1H), 6.70 (s, 1H), 5.55 (s, 1H), 4.24 (dd, J=7.4, 5.3 Hz, 1H), 3.76-3.65 (m, 1H), 3.57-3.46 (m, 1H), 1.60 (s, 2H).

Example 44

(1S)—N$^2$-1-(4-Chloro-3-fluoro-phenyl)-[6-(3-chloro-4-trifluoromethyl-phenyl)-pyrimidin-4-yl]-ethane-1,2-diamine

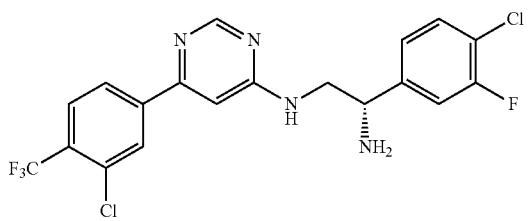 [SMILES: N[C@H](CNc1cc(-c2ccc(C(F)(F)F)c(Cl)c2)ncn1)c1ccc(Cl)c(F)c1]

MS (ESI$^+$): calcd for $C_{19}H_{14}Cl_2F_4N_4$ m/z 444.05. found 445.1 (M+H)$^+$. $^1$H NMR (CDCl$_3$): 8.66 (s, 1H), 8.11 (s, 1H), 7.92 (d, J=8.2 Hz, 1H), 7.77 (d, J=8.2 Hz, 1H), 7.39 (t, J=7.8 Hz, 1H), 7.23 (dd, J=9.9, 1.9 Hz, 1H), 7.13 (dd, J=8.2, 1.5 Hz, 1H), 6.70 (s, 1H), 5.45 (s, 1H), 4.25 (dd, J=7.2, 5.4 Hz, 1H), 3.76-3.65 (m, 1H), 3.56-3.46 (m, 1H), 1.57 (s, 2H).

Example 45

(1R)—N$^2$-1-(4-Chloro-3-fluoro-phenyl)-[6-(3-chloro-4-trifluoromethyl-phenyl)-pyrimidin-4-yl]-ethane-1,2-diamine

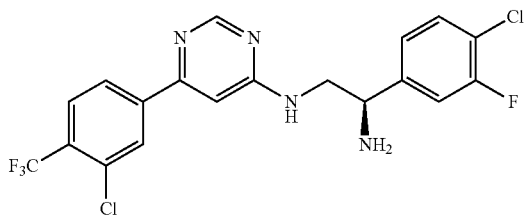 [SMILES: N[C@@H](CNc1cc(-c2ccc(C(F)(F)F)c(Cl)c2)ncn1)c1ccc(F)c(Cl)c1]

MS (ESI$^+$): calcd for $C_{19}H_{14}Cl_2F_4N_4$ m/z 444.05. found 445.1 (M+H)$^+$. $^1$H NMR (CDCl$_3$): 8.67 (s, 1H), 8.11 (s, 1H), 7.92 (d, J=7.4 Hz, 1H), 7.77 (d, J=8.3 Hz, 1H), 7.42-7.35 (m, 1H), 7.23 (dd, J=9.9, 2.0 Hz, 1H), 7.13 (dd, J=8.2, 2.0 Hz, 1H), 6.70 (d, J=0.9 Hz, 1H), 5.45 (s, 1H), 4.26 (dd, J=7.4, 5.2 Hz, 1H), 3.76-3.66 (m, 1H), 3.56-3.48 (m, 1H), 1.74 (s, 2H).

Example 46

(1S)—N$^2$-1-(3-Chloro-4-fluoro-phenyl)-[6-(3-chloro-4-trifluoromethyl-phenyl)-pyrimidin-4-yl]-ethane-1,2-diamine

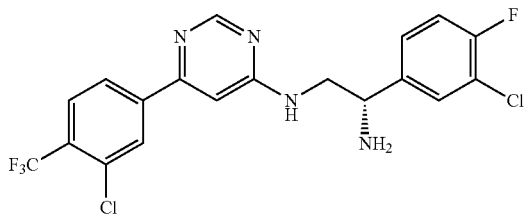

MS (ESI$^+$): calcd for $C_{19}H_{14}Cl_2F_4N_4$ m/z 444.05. found 445.1 (M+H)$^+$. $^1$H NMR (CDCl$_3$): 8.66 (s, 1H), 8.11 (s, 1H), 7.92 (d, J=8.3 Hz, 1H), 7.77 (d, J=8.3 Hz, 1H), 7.47 (dd, J=7.0, 2.1 Hz, 1H), 7.29-7.23 (m, 1H), 7.13 (t, J=8.6 Hz, 1H), 6.71 (s, 1H), 5.54 (s, 1H), 4.24 (dd, J=7.3, 5.3 Hz, 1H), 3.76-3.63 (m, 1H), 3.57-3.46 (m, 1H), 1.57 (s, 2H).

Example 47

(1R)—N$^2$-1-(3-Chloro-4-fluoro-phenyl)-[6-(3-chloro-4-trifluoromethyl-phenyl)-pyrimidin-4-yl]-ethane-1,2-diamine

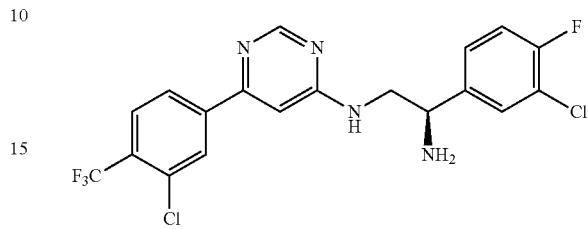

MS (ESI$^+$): calcd for $C_{19}H_{14}Cl_2F_4N_4$ m/z 444.05. found 445.1 (M+H)$^+$. $^1$H NMR (CDCl$_3$): 8.65 (s, 1H), 8.10 (s, 1H), 7.91 (d, J=8.6 Hz, 1H), 7.76 (d, J=8.3 Hz, 1H), 7.47 (dd, J=7.0, 2.2 Hz, 1H), 7.29-7.23 (m, 1H), 7.13 (t, J=8.6 Hz, 1H), 6.71 (d, J=0.6 Hz, 1H), 5.66 (s, 1H), 4.24 (dd, J=7.6, 5.2 Hz, 1H), 3.75-3.64 (m, 1H), 3.56-3.46 (m, 1H), 1.91 (s, 2H).

Example 48

(1S)-3-{1-Amino-2-[6-(3-chloro-4-trifluoromethyl-phenyl)-pyrimidin-4-ylamino]-ethyl}-benzonitrile

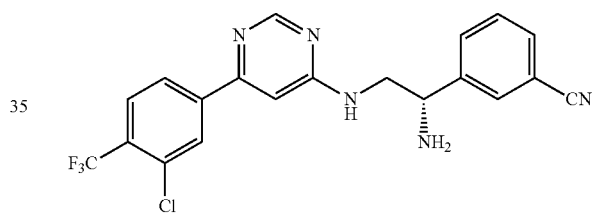

MS (ESI$^+$): calcd for $C_{20}H_{15}ClF_3N_5$ m/z 417.10. found 418.1 (M+H)$^+$. $^1$H NMR (CDCl$_3$): 8.67 (d, J=0.7 Hz, 1H), 8.12 (s, 1H), 7.93 (d, J=7.5 Hz, 1H), 7.80-7.74 (m, 2H), 7.66 (d, J=7.8 Hz, 1H), 7.60 (d, J=7.7 Hz, 1H), 7.49 (t, J=7.8 Hz, 1H), 6.73 (s, 1H), 5.57 (s, 1H), 4.37 (dd, J=7.7, 4.8 Hz, 1H), 3.82-3.71 (m, 1H), 3.61-3.52 (m, 1H), 2.12-1.99 (m, 2H).

Example 49

(1R)-3-{1-Amino-2-[6-(3-chloro-4-trifluoromethyl-phenyl)-pyrimidin-4-ylamino]-ethyl}-benzonitrile

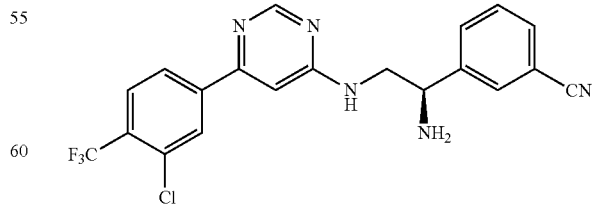

MS (ESI$^+$): calcd for $C_{20}H_{15}ClF_3N_5$ m/z 417.10. found 418.1 (M+H)$^+$. $^1$H NMR (CDCl$_3$): 8.63 (s, 1H), 8.08 (s, 1H), 7.89 (d, J=8.2 Hz, 1H), 7.76-7.72 (m, 2H), 7.67 (d, J=7.8 Hz, 1H), 7.57 (d, J=7.7 Hz, 1H), 7.47 (t, J=7.7 Hz, 1H), 6.73 (s, 1H), 5.89 (s, 1H), 4.42-4.32 (m, 1H), 3.77-3.72 (m, 1H), 3.62-3.52 (m, 1H), 2.80 (s, 2H).

Example 50

(1R)—N$^2$-1-(3-Chloro-4-fluoro-phenyl)-[6-(3-chloro-4-trifluoromethyl-phenyl)-pyrimidin-4-yl]-ethane-1,2-diamine

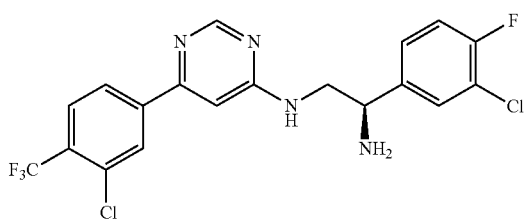 [SMILES: N[C@@H](CNc1cc(-c2ccc(C(F)(F)F)c(Cl)c2)ncn1)c1ccc(F)c(Cl)c1]

MS (ESI$^+$): calcd for C$_{19}$H$_{14}$Cl$_2$F$_4$N$_4$ m/z 444.05. found 445.1 (M+H)$^+$. $^1$H NMR (CDCl$_3$): 8.65 (s, 1H), 8.10 (s, 1H), 7.95-7.87 (m, 1H), 7.77 (t, J=6.8 Hz, 1H), 7.47 (dd, J=7.0, 2.2 Hz, 1H), 7.29-7.22 (m, 1H), 7.12 (dd, J=10.5, 6.7 Hz, 1H), 6.71 (d, J=0.6 Hz, 1H), 5.66 (s, 1H), 4.24 (dd, J=7.6, 5.2 Hz, 1H), 3.76-3.62 (m, 1H), 3.57-3.45 (m, 1H), 1.91 (s, 2H).

Example 51

(1R)—N$^2$-[6-(3-Chloro-4-trifluoromethyl-phenyl)-pyrimidin-4-yl]-1-naphthalen-2-yl-ethane-1,2-diamine

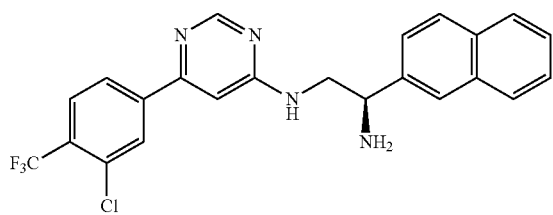 [SMILES: N[C@@H](CNc1cc(-c2ccc(C(F)(F)F)c(Cl)c2)ncn1)c1ccc2ccccc2c1]

MS (ESI$^+$): calcd for C$_{23}$H$_{18}$ClF$_3$N$_4$ m/z 442.12. found 443.1 (M+H)$^+$. $^1$H NMR (CDCl$_3$): 8.65 (d, J=8.8 Hz, 1H), 8.02 (d, J=10.0 Hz, 1H), 7.86-7.76 (m, 5H), 7.68 (dd, J=11.5, 7.5 Hz, 1H), 7.51-7.41 (m, 3H), 6.58 (s, 1H), 5.86-5.57 (m, 1H), 4.35 (dd, J=7.1, 5.7 Hz, 1H), 3.75 (s, 1H), 3.68-3.52 (m, 1H), 1.75 (s, 2H).

Example 52

(1R)-4-{1-Amino-2-[6-(3-chloro-4-trifluoromethyl-phenyl)-pyrimidin-4-ylamino]-ethyl}-2-fluoro-benzonitrile

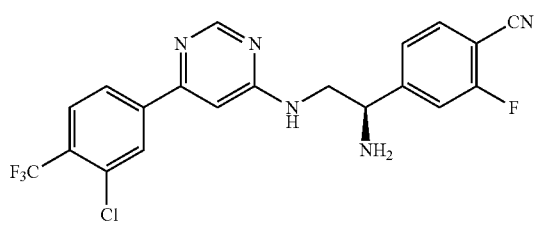 [SMILES: N#Cc1ccc([C@@H](N)CNc2cc(-c3ccc(C(F)(F)F)c(Cl)c3)ncn2)cc1F]

MS (ESI$^+$): calcd for C$_{20}$H$_{14}$ClF$_4$N$_5$ m/z 435.09. found 436.1 (M+H)$^+$. $^1$H NMR (CDCl$_3$): 8.65 (d, J=0.7 Hz, 1H), 8.11 (s, 1H), 7.94 (dd, J=8.2, 0.7 Hz, 1H), 7.76 (d, J=8.3 Hz, 1H), 7.59 (dt, J=14.1, 7.1 Hz, 1H), 7.43-7.33 (m, 2H), 6.89 (s, 1H), 6.18 (s, 1H), 4.40 (dd, J=7.7, 4.7 Hz, 1H), 3.84-3.73 (m, 1H), 3.53 (ddd, J=13.6, 7.7, 5.9 Hz, 1H).

Example 53

(1R)—N$^2$-[6-(3-Chloro-4-trifluoromethyl-phenyl)-pyrimidin-4-yl]-1-(3,4-dichloro-phenyl)-ethane-1,2-diamine

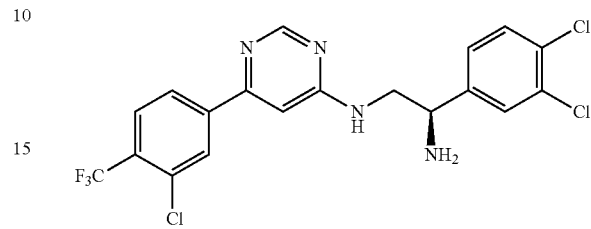

MS (ESI$^+$): calcd for C$_{19}$H$_{14}$Cl$_3$F$_3$N$_4$ m/z 460.02. found 461.0 (M+H)$^+$. $^1$H NMR (CDCl$_3$): 8.65 (d, J=12.1 Hz, 1H), 8.11 (s, 1H), 7.91 (d, J=8.2 Hz, 1H), 7.81-7.71 (m, 1H), 7.52 (d, J=2.0 Hz, 1H), 7.43 (d, J=8.3 Hz, 1H), 7.23 (dd, J=8.3, 2.0 Hz, 1H), 6.69 (d, J=12.2 Hz, 1H), 5.55 (s, 1H), 4.36-4.15 (m, 1H), 3.79-3.64 (m, 1H), 3.61-3.44 (m, 1H), 1.77-1.45 (m, 2H).

Example 54

(1R)—N$^2$-[6-(3-Chloro-4-trifluoromethyl-phenyl)-pyrimidin-4-yl]-1-(4-methylsulfanyl-phenyl)-ethane-1,2-diamine

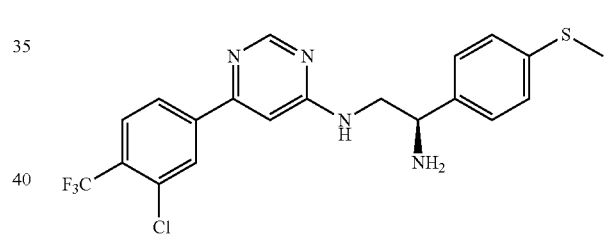

MS (ESI$^+$): calcd for C$_{20}$H$_{18}$ClF$_3$N$_4$S m/z 438.09. found 439.1 (M+H)$^+$. $^1$H NMR (CDCl$_3$): 8.66 (d, J=11.8 Hz, 1H), 8.09 (s, 1H), 7.90 (d, J=8.2 Hz, 1H), 7.75 (d, J=8.3 Hz, 1H), 7.34-7.19 (m, 6H), 6.66 (s, 1H), 5.61 (s, 1H), 4.18 (dt, J=14.8, 7.4 Hz, 1H), 3.65 (s, 1H), 3.51 (dt, J=16.6, 7.9 Hz, 1H), 2.47 (s, 3H).

Example 55

(1R)-3-{1-Amino-2-[6-(3-chloro-4-trifluoromethyl-phenyl)-pyrimidin-4-ylamino]-ethyl}-benzonitrile

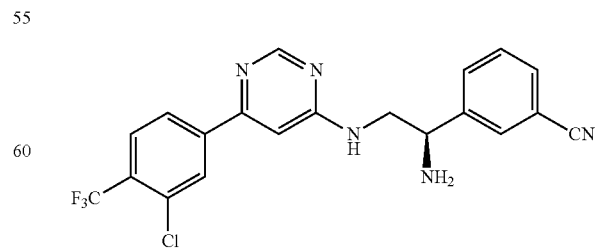

MS (ESI$^+$): calcd for C$_{20}$H$_{15}$ClF$_3$N$_5$ m/z 417.10. found 418.1 (M+H)$^+$. $^1$H NMR (CDCl$_3$): 8.63 (s, 1H), 8.08 (d, J=7.4 Hz, 1H), 7.90 (dd, J=8.8, 8.2 Hz, 1H), 7.74 (d, J=8.1 Hz, 2H), 7.67 (d, J=7.8 Hz, 1H), 7.57 (dt, J=7.6, 1.2 Hz, 1H), 7.46 (dd, J=14.5, 6.7 Hz, 1H), 6.76-6.71 (m, 1H), 5.98-5.81 (m, 1H), 4.42-4.27 (m, 1H), 3.75 (s, 1H), 3.62-3.52 (m, 1H), 2.80 (s, 2H).

Example 56

(1R)—N²-[6-(3-Chloro-4-trifluoromethyl-phenyl)-pyrimidin-4-yl]-1-(2-methoxy-phenyl)-ethane-1,2-diamine

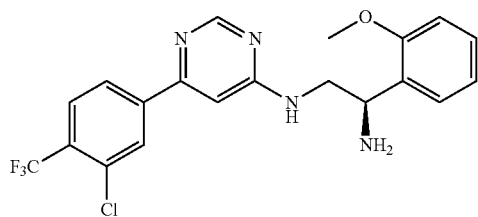 [SMILES: COc1ccccc1[C@@H](N)CNc1cc(-c2ccc(C(F)(F)F)c(Cl)c2)ncn1]

MS (ESI⁺): calcd for $C_{20}H_{18}ClF_3N_4O$ m/z 422.11. found 423.2 (M+H)⁺. ¹H NMR (CDCl₃): 8.62 (s, 1H), 8.09 (s, 1H), 7.93 (d, J=8.1 Hz, 1H), 7.76 (d, J=8.2 Hz, 1H), 7.34 (d, J=7.4 Hz, 1H), 7.28-7.22 (m, 1H), 6.96 (ddd, J=20.4, 13.5, 4.5 Hz, 2H), 6.73 (d, J=0.7 Hz, 1H), 5.87 (s, 1H), 4.50-4.39 (m, 1H), 3.94-3.83 (m, 3H), 3.74 (dd, J=18.7, 11.0 Hz, 1H), 3.49 (d, J=14.3 Hz, 1H).

Example 57

(1S)-3-{1-Amino-2-[6-(3-chloro-4-trifluoromethyl-phenyl)-pyrimidin-4-ylamino]-ethyl}-benzonitrile

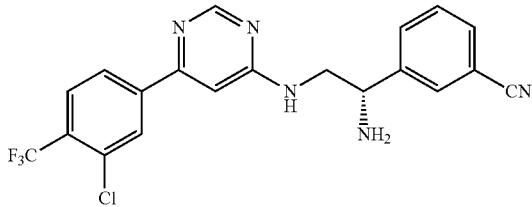 [SMILES: N#Cc1cccc([C@H](N)CNc2cc(-c3ccc(C(F)(F)F)c(Cl)c3)ncn2)c1]

MS (ESI⁺): calcd for $C_{20}H_{15}ClF_3N_5$ m/z 417.10. found 418.1 (M+H)⁺. ¹H NMR (CDCl₃): 8.67 (s, 1H), 8.12 (s, 1H), 7.93 (d, J=8.3 Hz, 1H), 7.77 (dd, J=14.7, 6.4 Hz, 2H), 7.66 (d, J=7.8 Hz, 1H), 7.62-7.58 (m, 1H), 7.52-7.46 (m, 1H), 6.73 (s, 1H), 5.57 (s, 1H), 4.37 (dd, J=7.7, 4.8 Hz, 1H), 3.73 (d, J=19.8 Hz, 1H), 3.65-3.50 (m, 1H), 2.07 (d, J=20.2 Hz, 2H).

Example 58

(1S)—N²-1-(3-Chloro-4-fluoro-phenyl)-[6-(3-chloro-4-trifluoromethyl-phenyl)-pyrimidin-4-yl]-ethane-1,2-diamine

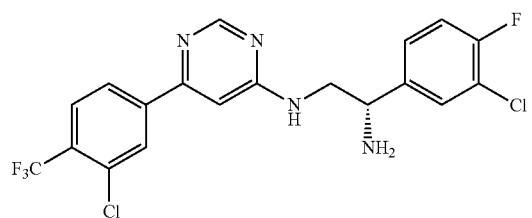

MS (ESI⁺): calcd for $C_{19}H_{14}Cl_2F_4N_4$ m/z 444.05. found 445.1 (M+H)⁺. ¹H NMR (CDCl₃): 8.67 (d, J=5.6 Hz, 1H), 8.11 (s, 1H), 7.92 (d, J=8.3 Hz, 1H), 7.77 (d, J=8.3 Hz, 1H), 7.46 (dt, J=9.0, 4.5 Hz, 1H), 7.25 (dd, J=4.5, 2.2 Hz, 1H), 7.13 (t, J=8.6 Hz, 1H), 6.71 (s, 1H), 5.54 (s, 1H), 4.24 (dd, J=7.3, 5.3 Hz, 1H), 3.78-3.62 (m, 1H), 3.63-3.45 (m, 1H), 1.54 (d, J=25.6 Hz, 2H).

Example 59

(1S)—N²-[6-(3-Chloro-4-trifluoromethyl-phenyl)-pyrimidin-4-yl]-1-(3,4-dichloro-phenyl)-ethane-1,2-diamine

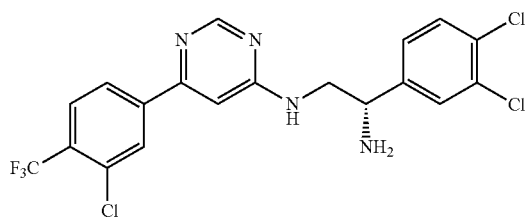

MS (ESI⁺): calcd for $C_{19}H_{14}Cl_3F_3N_4$ m/z 460.02. found 461.0 (M+H)⁺. ¹H NMR (CDCl₃): 8.66 (s, 1H), 8.11 (s, 1H), 7.92 (d, J=8.2 Hz, 1H), 7.77 (d, J=8.3 Hz, 1H), 7.52 (d, J=2.0 Hz, 1H), 7.46-7.40 (m, 1H), 7.23 (dd, J=8.3, 2.0 Hz, 1H), 6.70 (s, 1H), 5.49 (s, 1H), 4.32-4.15 (m, 1H), 3.78-3.61 (m, 1H), 3.63-3.45 (m, 1H), 1.54 (d, J=24.7 Hz, 2H).

Example 60

(1S)—N²-1-(4-Chloro-3-fluoro-phenyl)-[6-(3-chloro-4-trifluoromethyl-phenyl)-pyrimidin-4-yl]-ethane-1,2-diamine

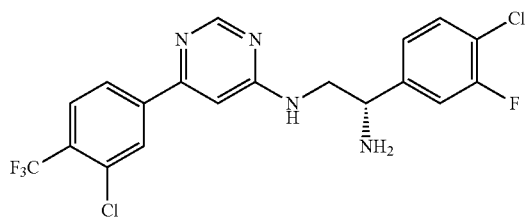 [SMILES: N[C@H](CNc1cc(-c2ccc(C(F)(F)F)c(Cl)c2)ncn1)c1ccc(F)c(Cl)c1]

MS (ESI⁺): calcd for $C_{19}H_{14}Cl_2F_4N_4$ m/z 444.05. found 445.1 (M+H)⁺. ¹H NMR (CDCl₃): 8.67 (d, J=6.8 Hz, 1H), 8.11 (s, 1H), 7.92 (d, J=8.2 Hz, 1H), 7.77 (d, J=8.2 Hz, 1H), 7.42-7.35 (m, 1H), 7.23 (dd, J=9.9, 1.9 Hz, 1H), 7.15-7.09 (m, 1H), 6.70 (s, 1H), 5.45 (s, 1H), 4.25 (dd, J=7.2, 5.4 Hz, 1H), 3.76-3.64 (m, 1H), 3.57-3.46 (m, 1H).

Example 61

(1R)—N²-[6-(3-Chloro-4-trifluoromethyl-phenyl)-pyrimidin-4-yl]-1-(4-trifluoromethylsulfanyl-phenyl)-ethane-1,2-diamine

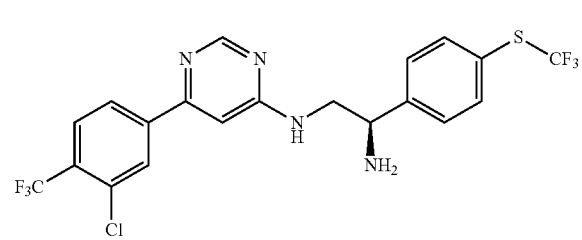 [SMILES: N[C@@H](CNc1cc(-c2ccc(C(F)(F)F)c(Cl)c2)ncn1)c1ccc(SC(F)(F)F)cc1]

MS (ESI⁺): calcd for $C_{20}H_{15}ClF_6N_4S$ m/z 492.06. found 493.1 (M+H)⁺. ¹H NMR (d₆-DMSO): 8.58 (s, 1H), 8.26 (s, 1H), 8.10 (s, 1H), 8.03-7.96 (m, 1H), 7.92 (d, J=8.2 Hz, 2H), 7.69 (t, J=21.0 Hz, 3H), 7.12 (s, 1H), 4.36 (s, 1H), 3.61 (s, 2H).

Example 62

(1R)-5-{1-Amino-2-[6-(3-chloro-4-trifluoromethyl-phenyl)-pyrimidin-4-ylamino]-ethyl}-2-fluoro-benzonitrile

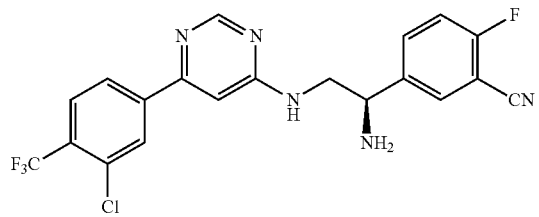 [SMILES: N#Cc1cc([C@@H](N)CNc2cc(-c3ccc(C(F)(F)F)c(Cl)c3)ncn2)ccc1F]

MS (ESI⁺): calcd for $C_{20}H_{14}ClF_4N_5$ m/z 435.09. found 436.1 (M+H)⁺. ¹H NMR (d₆-DMSO): 8.52 (d, J=20.1 Hz, 1H), 8.25 (s, 1H), 8.12 (d, J=15.5 Hz, 1H), 7.99 (d, J=8.2 Hz, 1H), 7.69 (d, J=7.9 Hz, 2H), 7.62 (d, J=8.2 Hz, 2H), 7.12 (s, 1H), 4.24 (s, 1H), 3.60 (d, J=33.2 Hz, 2H).

Example 63

(1R)—N²-[6-(3-Chloro-4-trifluoromethyl-phenyl)-pyrimidin-4-yl]-1-(4-methanesulfonyl-phenyl)-ethane-1,2-diamine

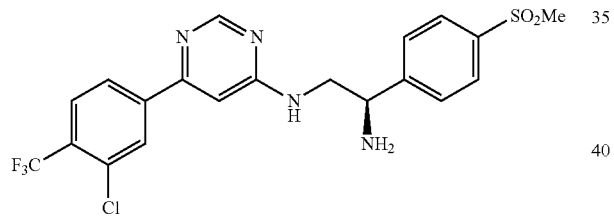

MS (ESI⁺): calcd for $C_{20}H_{18}ClF_3N_4O_2S$ m/z 470.08. found 471.1 (M+H)⁺. ¹H NMR (d₆-DMSO): 8.51 (t, J=6.4 Hz, 1H), 8.25 (d, J=8.0 Hz, 1H), 8.11 (d, J=8.2 Hz, 1H), 7.97 (dd, J=19.1, 7.6 Hz, 2H), 7.85-7.76 (m, 1H), 7.57 (s, 1H), 7.52-7.40 (m, 2H), 7.10 (d, J=7.6 Hz, 1H), 4.14 (t, J=6.5 Hz, 1H), 3.52 (s, 2H), 2.51 (s, 3H).

Example 64

(1R)—N²-1-(4-Fluoro-phenyl)-[6-(3-fluoro-4-trifluoromethoxy-phenyl)-pyrimidin-4-yl]-ethane-1,2-diamine, trifluoroacetic acid salt

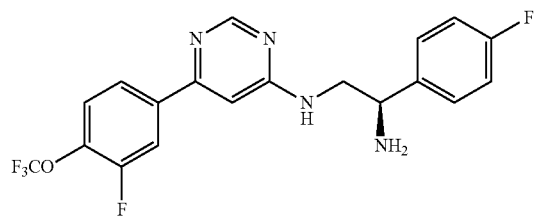 [SMILES: N[C@@H](CNc1cc(-c2ccc(OC(F)(F)F)c(F)c2)ncn1)c1ccc(F)cc1]

MS (ESI⁺): calcd for $C_{19}H_{15}ClF_5N_4O$ m/z 410.12. found 411.1 (M+H)⁺. ¹H NMR (d₆-DMSO): 8.63 (s, 1H), 8.54 (s, 2H), 8.27 (s, 1H), 8.16-8.09 (m, 1H), 8.00 (d, J=8.4 Hz, 1H), 7.75-7.67 (m, 1H), 7.53 (s, 4H), 7.11 (d, J=1.0 Hz, 1H), 4.59 (s, 1H), 3.95-3.86 (m, 1H), 3.83-3.73 (m, 1H).

Example 65

(1R)—N²-1-(4-Fluoro-phenyl)-[6-(3-trifluoromethyl-benzo[d]isoxazol-6-yl)-pyrimidin-4-yl]ethane-1,2-diamine, trifluoroacetic acid salt

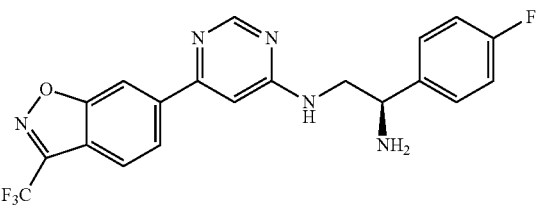 [SMILES: N[C@@H](CNc1cc(-c2ccc3c(C(F)(F)F)noc3c2)ncn1)c1ccc(F)cc1]

MS (ESI⁺): calcd for $C_{20}H_{15}F_4N_5O$ m/z 417.12. found 418.2 (M+H)⁺. ¹H NMR (d₆-DMSO): 8.63 (s, 1H), 8.54 (s, 2H), 8.27 (s, 1H), 8.16-8.09 (m, 1H), 8.00 (d, J=8.4 Hz, 1H), 7.75-7.67 (m, 1H), 7.53 (s, 4H), 7.11 (d, J=1.0 Hz, 1H), 4.59 (s, 1H), 3.95-3.86 (m, 1H), 3.83-3.73 (m, 1H).

The following examples may be synthesized by using synthetic methods analogous to those described in Schemes A and B and exemplified in Examples 1 through 65.

Example 66

(1R)-Phenyl-N²-(6-quinolin-6-yl-pyrimidin-4-yl)-ethane-1,2-diamine

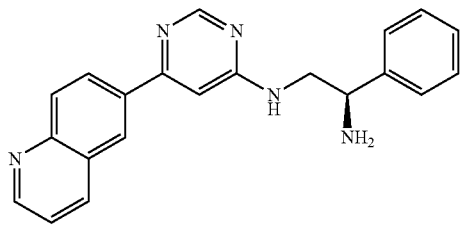 [SMILES: N[C@@H](CNc1cc(-c2ccc3ncccc3c2)ncn1)c1ccccc1]

Example 67

(1R)—N²-[6-(5-Fluoro-benzo[b]thiophen-2-yl)-pyrimidin-4-yl]-1-phenyl-ethane-1,2-diamine

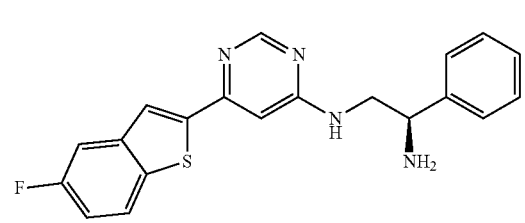 [SMILES: N[C@@H](CNc1cc(-c2cc3cc(F)ccc3s2)ncn1)c1ccccc1]

Example 68

(1R)-Phenyl-$N^2$-[6-(5-trifluoromethyl-benzo[b]thiophen-2-yl)-pyrimidin-4-yl]-ethane-1,2-diamine

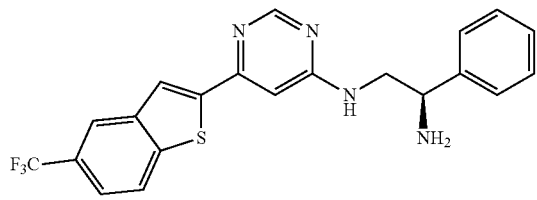 [SMILES: N[C@@H](CNc1cc(-c2cc3cc(C(F)(F)F)ccc3s2)ncn1)c1ccccc1]

Example 69

(1R)-{4-[6-(2-Amino-2-phenyl-ethylamino)-pyrimidin-4-yl]-2-fluoro-phenyl}-ethanol

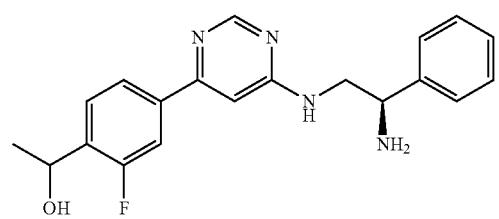 [SMILES: CC(O)c1ccc(-c2cc(NC[C@H](N)c3ccccc3)ncn2)cc1F]

Example 70

(1R)-Phenyl-$N^2$-[6-(6-trifluoromethyl-benzo[b]thiophen-2-yl)-pyrimidin-4-yl]-ethane-1,2-diamine

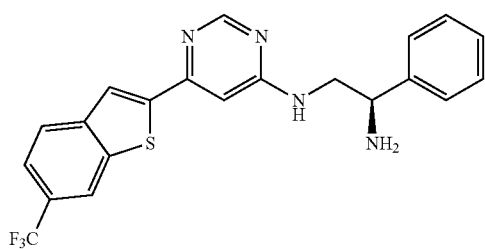 [SMILES: N[C@@H](CNc1cc(-c2cc3ccc(C(F)(F)F)cc3s2)ncn1)c1ccccc1]

Example 71

(1R)—$N^2$-[6-(3-Methyl-benzo[d]isoxazol-6-yl)-pyrimidin-4-yl]-1-phenyl-ethane-1,2-diamine

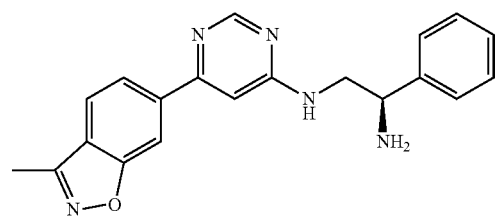 [SMILES: Cc1noc2cc(-c3cc(NC[C@H](N)c4ccccc4)ncn3)ccc12]

Example 72

(1R)—$N^2$-(6-Benzo[b]thiophen-2-yl-pyrimidin-4-yl)-1-phenyl-ethane-1,2-diamine

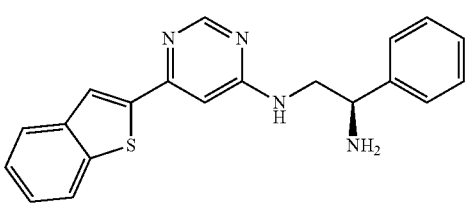 [SMILES: N[C@@H](CNc1cc(-c2cc3ccccc3s2)ncn1)c1ccccc1]

Example 73

(1R)-{5-[6-(2-Amino-2-phenyl-ethylamino)-pyrimidin-4-yl]-thiophen-2-yl}-ethanone

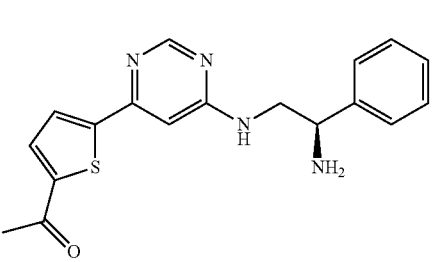 [SMILES: CC(=O)c1ccc(-c2cc(NC[C@H](N)c3ccccc3)ncn2)s1]

Example 74

(1R)—$N^2$-[6-(3,4-Dimethoxy-phenyl)-pyrimidin-4-yl]-1-phenyl-ethane-1,2-diamine

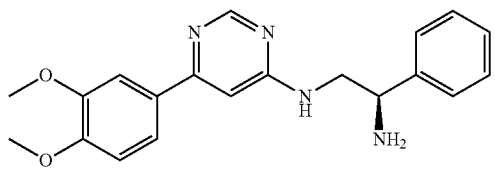 [SMILES: COc1ccc(-c2cc(NC[C@H](N)c3ccccc3)ncn2)cc1OC]

Example 75

(1R)—$N^2$-(6-Benzo[1,3]dioxol-5-yl-pyrimidin-4-yl)-1-phenyl-ethane-1,2-diamine

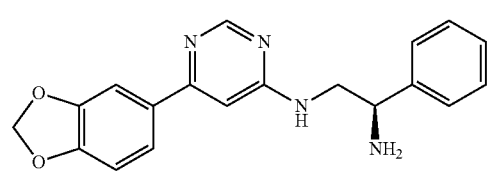 [SMILES: N[C@@H](CNc1cc(-c2ccc3c(c2)OCO3)ncn1)c1ccccc1]

Example 76

(1R)-4-[6-(2-Amino-2-phenyl-ethylamino)-pyrimidin-4-yl]-phenol

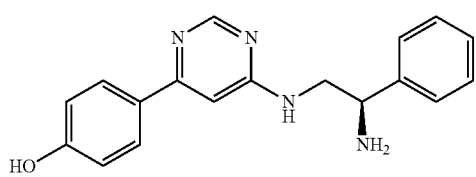 [SMILES: N[C@@H](CNc1cc(-c2ccc(O)cc2)ncn1)c1ccccc1]

Example 77

(1R)—N²-[6-(3-Pentafluoroethyl-benzo[d]isoxazol-6-yl)-pyrimidin-4-yl]-1-phenyl-ethane-1,2-diamine

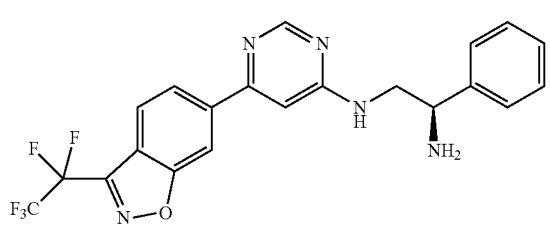 [SMILES: N[C@@H](CNc1cc(-c2ccc3c(C(F)(F)C(F)(F)F)noc3c2)ncn1)c1ccccc1]

Example 78

(1R)—N²-[6-(3,4-Dichloro-phenyl)-pyrimidin-4-yl]-1-phenyl-ethane-1,2-diamine

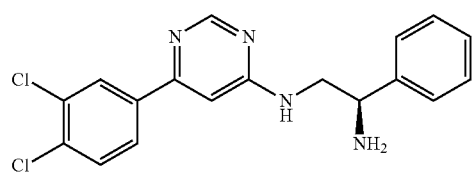 [SMILES: N[C@@H](CNc1cc(-c2ccc(Cl)c(Cl)c2)ncn1)c1ccccc1]

Example 79

(1R)—N²-[6-(4-Methoxy-phenyl)-pyrimidin-4-yl]-1-phenyl-ethane-1,2-diamine

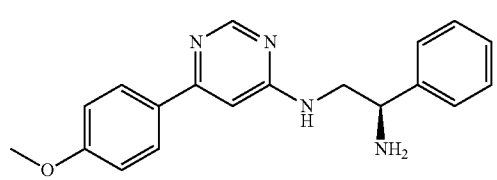 [SMILES: COc1ccc(-c2cc(NC[C@H](N)c3ccccc3)ncn2)cc1]

Example 80

(1R)-4-[6-(2-Amino-2-phenyl-ethylamino)-pyrimidin-4-yl]-N-tert-butyl-benzenesulfonamide

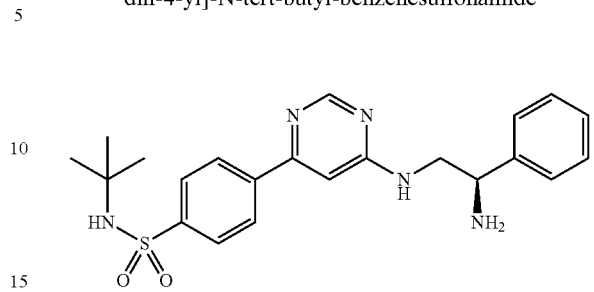

Example 81

(1R)-1-Phenyl-N²-{6-[4-(thiomorpholine-4-sulfonyl)-phenyl]-pyrimidin-4-yl}-ethane-1,2-diamine

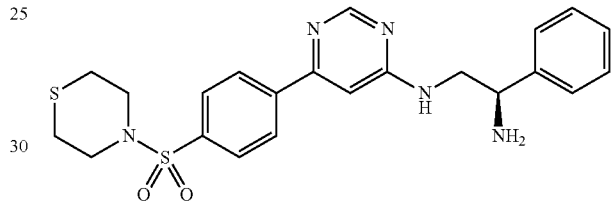

Example 82

(1R)—N²-[6-(3-Chloro-4-trifluoromethyl-phenyl)-pyrimidin-4-yl]-1-thiophen-3-yl-ethane-1,2-diamine

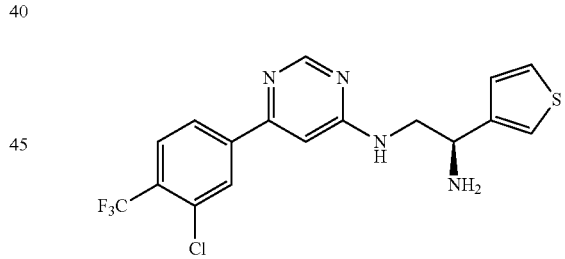

Example 83

(1R)—N²-[6-(3-Chloro-4-trifluoromethyl-phenyl)-pyrimidin-4-yl]-1-thiazol-2-yl-ethane-1,2-diamine

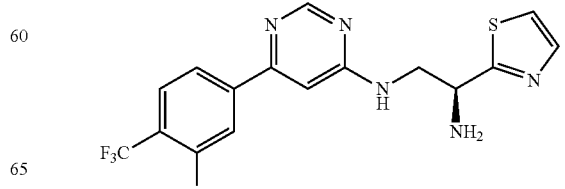

Example 84

(1R)-1-Benzo[b]thiophen-2-yl-N2-[6-(3-chloro-4-trifluoromethyl-phenyl)-pyrimidin-4-yl]-ethane-1,2-diamine

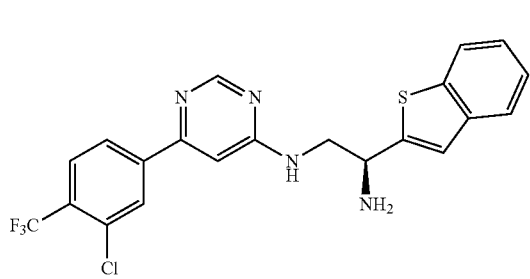 [SMILES: N[C@@H](CNc1cc(-c2ccc(C(F)(F)F)c(Cl)c2)ncn1)c1cc2ccccc2s1]

Example 85

(1R)-1-Benzo[b]thiophen-3-yl-$N^2$-[6-(3-chloro-4-trifluoromethyl-phenyl)-pyrimidin-4-yl]-ethane-1,2-diamine

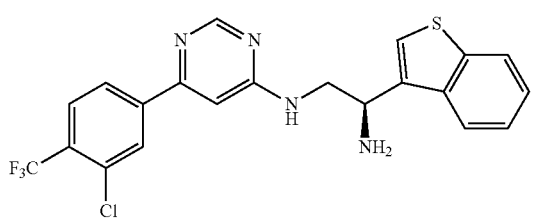 [SMILES: N[C@@H](CNc1cc(-c2ccc(C(F)(F)F)c(Cl)c2)ncn1)c1csc2ccccc12]

Example 86

(1R)—$N^2$-[6-(3-Chloro-4-trifluoromethyl-phenyl)-pyrimidin-4-yl]-1-(3-fluoro-4-trifluoromethyl-phenyl)-ethane-1,2-diamine

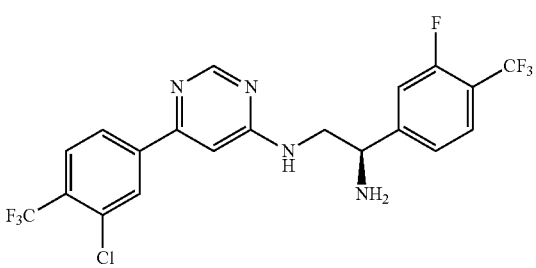 [SMILES: N[C@@H](CNc1cc(-c2ccc(C(F)(F)F)c(Cl)c2)ncn1)c1ccc(C(F)(F)F)c(F)c1]

Example 87

(1R)—$N^2$-[6-(3-Chloro-4-trifluoromethyl-phenyl)-pyrimidin-4-yl]-1-(2,3-dihydro-benzo[1,4]dioxin-6-yl)-ethane-1,2-diamine

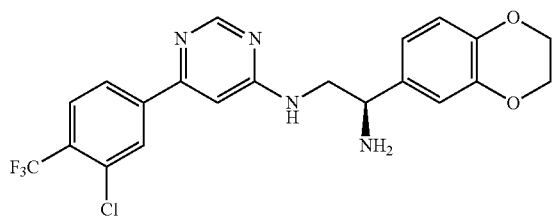 [SMILES: N[C@@H](CNc1cc(-c2ccc(C(F)(F)F)c(Cl)c2)ncn1)c1ccc2c(c1)OCCO2]

Example 88

(1R)—$N^2$-[6-(3-Chloro-4-trifluoromethyl-phenyl)-pyrimidin-4-yl]-1-(4-imidazol-1-yl-phenyl)-ethane-1,2-diamine

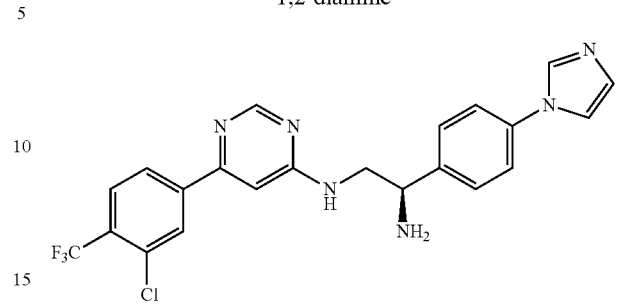

Example 89

(1R)—$N^2$-[6-(3-Chloro-4-trifluoromethyl-phenyl)-pyrimidin-4-yl]-1-(3-trifluoromethylsulfanyl-phenyl)-ethane-1,2-diamine

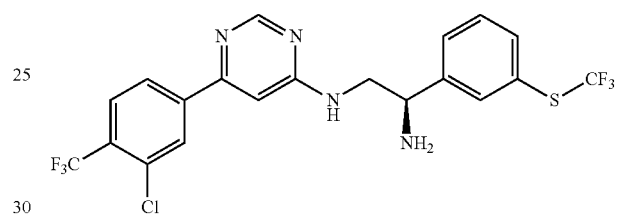

Example 90

(1R)—$N^2$-[6-(3-Chloro-4-trifluoromethyl-phenyl)-pyrimidin-4-yl]-1-(3,4-dimethoxy-phenyl)-ethane-1,2-diamine

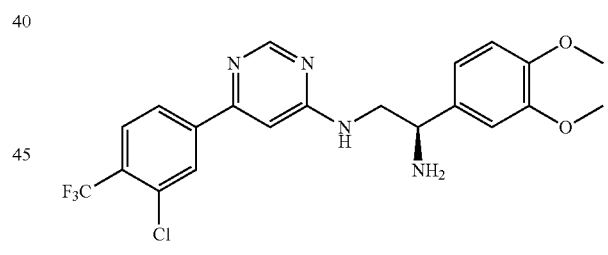

Example 91

(1R)-1-(3-Chloro-4-methoxy-phenyl)-$N^2$-[6-(3-chloro-4-trifluoromethyl-phenyl)-pyrimidin-4-yl]-ethane-1,2-diamine

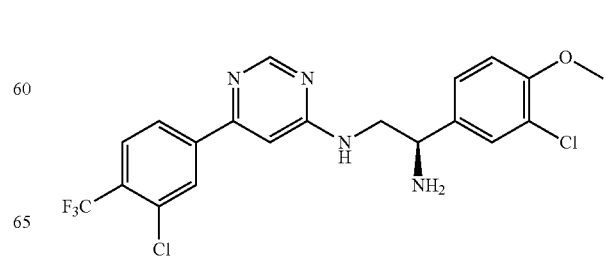

Example 92

(1R)—N²-[6-(3-Chloro-4-trifluoromethyl-phenyl)-pyrimidin-4-yl]-1-(3,4-dihydro-2H-benzo[b][1,4]dioxepin-7-yl)-ethane-1,2-diamine

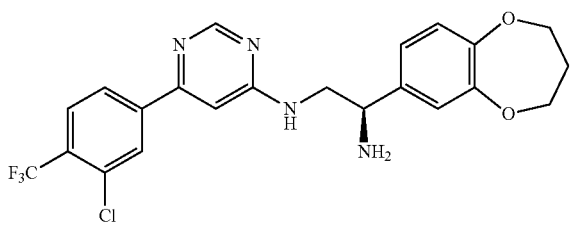 [SMILES: N[C@@H](CNc1cc(-c2ccc(C(F)(F)F)c(Cl)c2)ncn1)c1ccc2c(c1)OCCCO2]

Example 93

(1R)—N²-[6-(3-Chloro-4-trifluoromethyl-phenyl)-pyrimidin-4-yl]-1-(2-difluoromethoxy-phenyl)-ethane-1,2-diamine

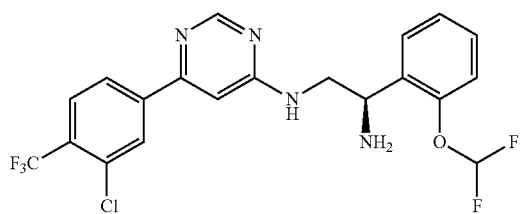 [SMILES: N[C@@H](CNc1cc(-c2ccc(C(F)(F)F)c(Cl)c2)ncn1)c1ccccc1OC(F)F]

Example 94

(1R)—N²-[6-(3-Chloro-4-trifluoromethyl-phenyl)-pyrimidin-4-yl]-1-(2-fluoro-5-trifluoromethyl-phenyl)-ethane-1,2-diamine

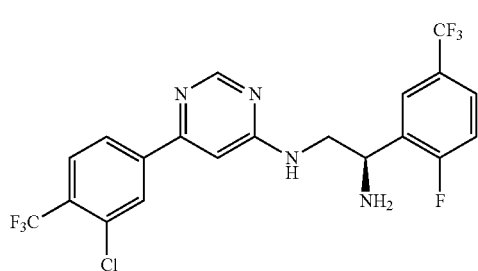 [SMILES: N[C@@H](CNc1cc(-c2ccc(C(F)(F)F)c(Cl)c2)ncn1)c1cc(C(F)(F)F)ccc1F]

Example 95

(1R)—N²-[6-(3-Chloro-4-trifluoromethyl-phenyl)-pyrimidin-4-yl]-1-(4-pyrrolidin-1-yl-phenyl)-ethane-1,2-diamine

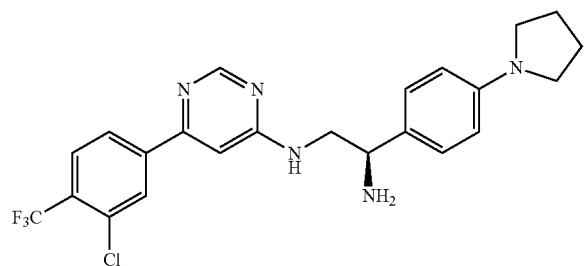 [SMILES: N[C@@H](CNc1cc(-c2ccc(C(F)(F)F)c(Cl)c2)ncn1)c1ccc(N2CCCC2)cc1]

Example 96

(1R)—N²-[6-(3-Chloro-4-trifluoromethyl-phenyl)-pyrimidin-4-yl]-1-(3-phenyl-isoxazol-5-yl)-ethane-1,2-diamine

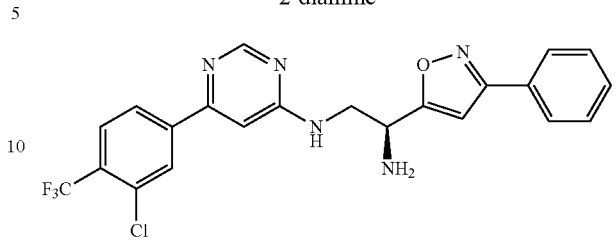

Example 97

(1R)—N²-[6-(3-Chloro-4-trifluoromethyl-phenyl)-pyrimidin-4-yl]-1-(4-pyridin-2-yl-thiophen-2-yl)-ethane-1,2-diamine

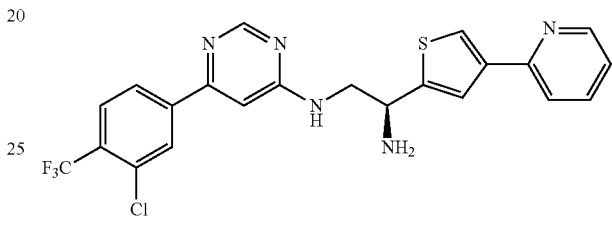

Example 98

(1R)—N²-[6-(3-Chloro-4-trifluoromethyl-phenyl)-pyrimidin-4-yl]-1-(4-pyridin-2-yl-phenyl)-ethane-1,2-diamine

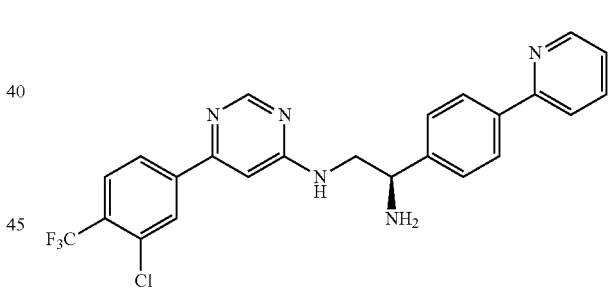

Example 99

(1R)-1-Biphenyl-4-yl-N²-[6-(3-chloro-4-trifluoromethyl-phenyl)-pyrimidin-4-yl]-ethane-1,2-diamine

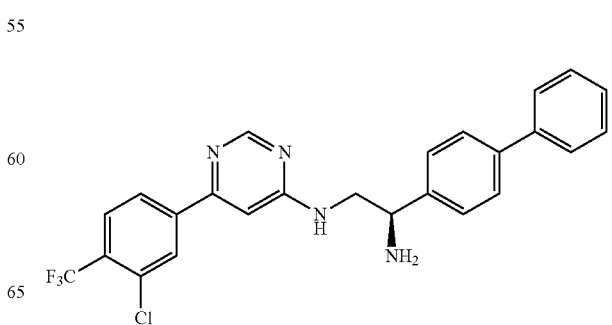

Example 100

(1R)—N²-[6-(3-Chloro-4-trifluoromethyl-phenyl)-pyrimidin-4-yl]-1-(3-trifluoromethyl-phenyl)-ethane-1,2-diamine

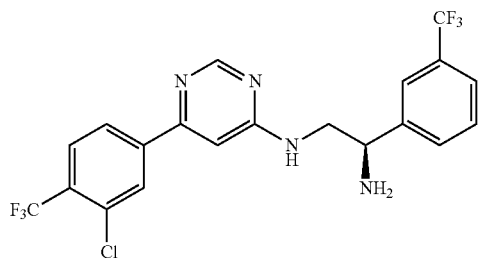 [SMILES: N[C@@H](CNc1cc(-c2ccc(C(F)(F)F)c(Cl)c2)ncn1)c1cccc(C(F)(F)F)c1]

Example 101

(1R)—N²-[6-(3-Chloro-4-trifluoromethyl-phenyl)-pyrimidin-4-yl]-1-(2,6-difluoro-phenyl)-ethane-1,2-diamine

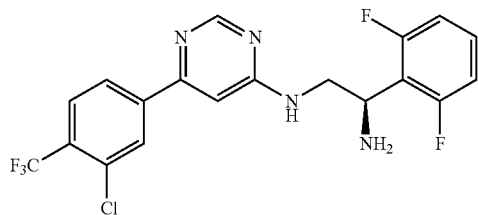 [SMILES: N[C@@H](CNc1cc(-c2ccc(C(F)(F)F)c(Cl)c2)ncn1)c1c(F)cccc1F]

Example 102

(1R)—N²-[6-(3-Chloro-4-trifluoromethyl-phenyl)-pyrimidin-4-yl]-1-(4-thiophen-2-yl-phenyl)-ethane-1,2-diamine

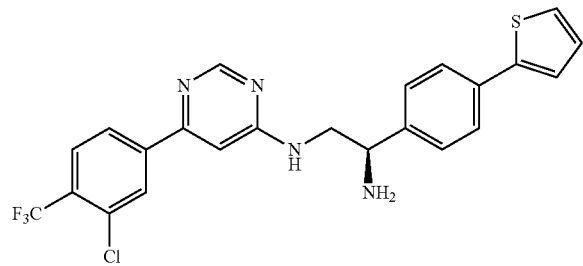 [SMILES: N[C@@H](CNc1cc(-c2ccc(C(F)(F)F)c(Cl)c2)ncn1)c1ccc(-c2cccs2)cc1]

Example 103

(1R)—N²-[6-(3-Chloro-4-trifluoromethyl-phenyl)-pyrimidin-4-yl]-1-(3-trifluoromethoxy-phenyl)-ethane-1,2-diamine

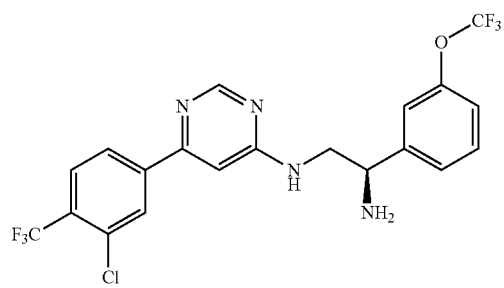 [SMILES: N[C@@H](CNc1cc(-c2ccc(C(F)(F)F)c(Cl)c2)ncn1)c1cccc(OC(F)(F)F)c1]

Biological Testing

Assay Method 1

A. Transfection of Cells with Human FAAH

A 10-cm tissue culture dish with a confluent monolayer of SK-N-MC cells was split 2 days (d) prior to transfection. Using sterile technique, the media was removed and the cells were detached from the dish by the addition of trypsin. One fifth of the cells were then placed onto a new 10-cm dish. Cells were grown in a 37° C. incubator with 5% $CO_2$ in Minimal Essential Media Eagle with 10% Fetal Bovine Serum. After 2 d, cells were approximately 80% confluent. These cells were removed from the dish with trypsin and pelleted in a clinical centrifuge. The pellet was re-suspended in 400 µL complete media and transferred to an electroporation cuvette with a 0.4 cm gap between the electrodes. Supercoiled human FAAH cDNA (1 µg) was added to the cells and mixed. The voltage for the electroporation was set at 0.25 kV, and the capacitance was set at 960 µF. After electroporation, the cells were diluted into complete media (10 mL) and plated onto four 10-cm dishes. Because of the variability in the efficiency of electroporation, four different concentrations of cells were plated. The ratios used were 1:20, 1:10, and 1:5, with the remainder of the cells being added to the fourth dish. The cells were allowed to recover for 24 h before adding the selection media (complete media with 600 µg/mL G418). After 10 d, dishes were analyzed for surviving colonies of cells. Dishes with well-isolated colonies were used. Cells from individual colonies were isolated and tested. The clones that showed the most FAAH activity, as measured by anandamide hydrolysis, were used for further study.

B. Human FAAH Assay

T84 frozen cell pellets or transfected SK-N-MC cells (contents of 1×15 cm culture dishes) were homogenized in 50 mL of FAAH assay buffer (125 mM Tris, 1 mM EDTA, 0.2% Glycerol, 0.02% Triton X-100, 0.4 mM Hepes, pH 9). The assay mixture consisted of 50 µL of the cell homogenate, 10 µL of the test compound, and 40 µL of anandamide [1-3H-ethanolamine] (³H-AEA, Perkin-Elmer, 10.3 $C_i$/mmol), which was added last, for a final tracer concentration of 80 nM. The reaction mixture was incubated at rt for 1 h. During the incubation, 96-well Multiscreen filter plates (catalog number MAFCNOB50; Millipore, Bedford, Mass., USA) were loaded with 25 µL of activated charcoal (Multiscreen column loader, catalog number MACL09625, Millipore) and washed once with 100 µL of MeOH. Also during the incubation, 96-well DYNEX MicroLite plates (catalog number NL510410) were loaded with 100 µL of MicroScint40 (catalog number 6013641, Packard Bioscience, Meriden, Conn., USA). After the 1 h incubation, 60 µL of the reaction mixture were transferred to the charcoal plates, which were then assembled on top of the DYNEX plates using Centrifuge Alignment Frames (catalog number MACF09604, Millipore). The unbound labeled ethanolamine was centrifuged through to the bottom plate (5 min at 2000 rpm), which was preloaded with the scintillant, as described above. The plates were sealed and left at rt for 1 h before counting on a Hewlett Packard TopCount.

Assay Method 2

A. Transfection of Cells with Rat FAAH-1

A 10-cm tissue culture dish with a confluent monolayer of SK-N-MC cells was split 2 days (d) prior to transfection. Using sterile technique, the media was removed and the cells were detached from the dish by the addition of trypsin. One fifth of the cells were then placed onto a new 10-cm dish. Cells were grown in a 37° C. incubator with 5% $CO_2$ in Minimal Essential Media Eagle with 10% Fetal Bovine Serum. After 2 d, cells were approximately 80% confluent. These cells were removed from the dish with trypsin and pelleted in a clinical centrifuge. The pellet was re-suspended in 400 µL complete media and transferred to an electroporation cuvette with a 0.4 cm gap between the electrodes. Supercoiled rat FAAH cDNA (1 µg) was added to the cells and mixed. The voltage for the electroporation was set at 0.25 kV, and the capacitance was set at 960 µF. After electroporation, the cells were diluted into complete media (10 mL) and plated onto four 10-cm dishes. Because of the variability in the efficiency of electroporation, four different concentrations of cells were plated. The ratios used were 1:20, 1:10, and 1:5, with the remainder of the cells being added to the fourth dish. The cells were allowed to recover for 24 h before adding the selection media (complete media with 600 µg/mL G418). After 10 d, dishes were analyzed for surviving colonies of cells. Dishes with well-isolated colonies were used. Cells from individual colonies were isolated and tested. The clones that showed the most FAAH activity, as measured by anandamide hydrolysis, were used for further study.

B. Rat FAAH-1 Assay

T84 frozen cell pellets or transfected SK-N-MC cells (contents of 1×15 cm culture dishes) were homogenized in 50 mL of FAAH assay buffer (125 mM Tris, 1 mM EDTA, 0.2% Glycerol, 0.02% Triton X-100, 0.4 mM Hepes, pH 9). The assay mixture consisted of 50 µL of the cell homogenate, 10 µL of the test compound, and 40 µL of anandamide [1-$^3$H-ethanolamine] ($^3$H-AEA, Perkin-Elmer, 10.3 C$_i$/mmol), which was added last, for a final tracer concentration of 80 nM. The reaction mixture was incubated at rt for 1 h. During the incubation, 96-well Multiscreen filter plates (catalog number MAFCNOB50; Millipore, Bedford, Mass., USA) were loaded with 25 µL of activated charcoal (Multiscreen column loader, catalog number MACL09625, Millipore) and washed once with 100 µL of MeOH. Also during the incubation, 96-well DYNEX MicroLite plates (catalog number NL510410) were loaded with 100 µL of MicroScint40 (catalog number 6013641, Packard Bioscience, Meriden, Conn., USA). After the 1 h incubation, 60 µL of the reaction mixture were transferred to the charcoal plates, which were then assembled on top of the DYNEX plates using Centrifuge Alignment Frames (catalog number MACF09604, Millipore). The unbound labeled ethanolamine was centrifuged through to the bottom plate (5 min at 2000 rpm), which was preloaded with the scintillant, as described above. The plates were sealed and left at rt for 1 h before counting on a Hewlett Packard TopCount.

Results for Example compounds tested in these assays are presented in Table 1. Where activity is shown as greater than (>) a particular value, the value is the solubility limit of the compound in the assay medium or the highest concentration tested in the assay.

TABLE 1

| Ex. | Assay 1 IC$_{50}$ (µM) | Assay 2 IC$_{50}$ (µM) |
|---|---|---|
| 1 | 0.050 | 0.060 |
| 2 | 0.330 | 8.000 |
| 3 | 1.300 | 2.400 |
| 4 | 0.100 | 0.320 |
| 5 | 0.130 | 1.000 |
| 6 | 0.082 | 0.880 |
| 7 | 0.053 | 0.120 |
| 8 | 0.050 | 0.170 |
| 9 | 0.020 | 0.320 |
| 10 | 0.026 | 0.084 |
| 11 | 0.019 | 0.170 |
| 12 | 0.012 | 0.100 |
| 13 | 0.044 | 0.071 |

TABLE 1-continued

| Ex. | Assay 1 IC$_{50}$ (µM) | Assay 2 IC$_{50}$ (µM) |
|---|---|---|
| 14 | 1.000 | >10 |
| 15 | 1.000 | 10.000 |
| 16 | 0.090 | 0.500 |
| 17 | 0.250 | 0.900 |
| 18 | 0.920 | >10 |
| 19 | 0.070 | 1.000 |
| 20 | 0.130 | 2.000 |
| 21 | 0.077 | 0.675 |
| 22 | 0.007 | 0.240 |
| 23 | 0.113 | 1.600 |
| 24 | 0.270 | 1.000 |
| 25 | 0.080 | 0.370 |
| 26 | 1.600 | >10 |
| 27 | 0.033 | 0.060 |
| 28 | 0.600 | 0.900 |
| 29 | 1.400 | 1.700 |
| 30 | 0.160 | 0.052 |
| 31 | 0.630 | 0.770 |
| 32 | 0.030 | 0.011 |
| 33 | 0.570 | 1.000 |
| 34 | 0.077 | 0.130 |
| 35 | 0.170 | 0.280 |
| 36 | 1.000 | 2.600 |
| 37 | 0.039 | 0.110 |
| 38 | 1.600 | 2.200 |
| 39 | 0.066 | 0.040 |
| 40 | 1.000 | 5.000 |
| 41 | 0.020 | 0.060 |
| 42 | 8.000 | 5.000 |
| 43 | 0.200 | 0.095 |
| 44 | 10.000 | 10.000 |
| 45 | 0.080 | 0.070 |
| 46 | 3.000 | 3.000 |
| 47 | 0.120 | 0.115 |
| 48 | 3.000 | 3.000 |
| 49 | 1.000 | 0.770 |
| 50 | 0.120 | 0.115 |
| 51 | 0.125 | 0.040 |
| 52 | 0.130 | 0.240 |
| 53 | 0.200 | 0.095 |
| 54 | 0.220 | 0.150 |
| 55 | 1.000 | 0.770 |
| 56 | 1.200 | 5.999 |
| 57 | 3.000 | 3.000 |
| 58 | 3.000 | 3.000 |
| 59 | 8.000 | 5.000 |
| 60 | 10.000 | 10.000 |
| 61 | 0.180 | 0.130 |
| 62 | 0.320 | 0.300 |
| 63 | >10 | >10 |
| 64 | 0.066 | 0.075 |
| 65 | 0.045 | 0.057 |

While the invention has been illustrated by reference to exemplary and preferred embodiments, it will be understood that the invention is intended not to be limited to the foregoing detailed description, but to be defined by the appended claims as properly construed under principles of patent law.

What is claimed is:

1. A compound of Formula (I):

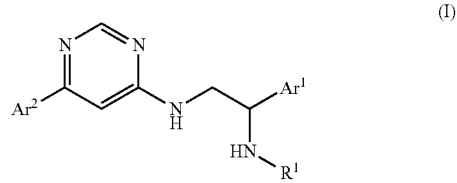

wherein
R$^1$ is —H, —C(O)CF$_3$, or —CO$_2$C(CH$_3$)$_3$;

$Ar^1$ is phenyl, napthyl, a 5 or 6 membered monocyclic heteroaryl group with carbon at the point of attachment, or a 9 or 10 membered bicyclic heteroaryl group with carbon at the point of attachment, each unsubstituted or substituted with;
  (i) one, two, or three $R^c$ moieties,
    where each $R^c$ moiety is independently —$C_{1-4}$alkyl, —$C_{1-4}$alkyl-OH, —$C_{1-4}$alkyl-CN, —OH, —$OC_{1-4}$alkyl, perfluoroalkyl, perfluoroalkoxy, —$S(O)_{0-2}C_{1-4}$alkyl, —$SCF_3$, —$SO_2CF_3$, —CHO, —$COC_{1-4}$alkyl, —$CO_2C_{1-4}$alkyl, —$CO_2H$, —$N(R^d)R^e$, —$SO_2NR^dR^e$, —$NR^dSO_2R^e$, —$C(O)NR^dR^e$, —$NO_2$, —CN, imidazolyl, phenyl, pyridyl, pyrrolidinyl, thiophenyl, or halo,
      where $R^d$ and $R^e$ are each independently H or —$C_{1-4}$alkyl, or taken together $R^d$ and $R^e$ with the nitrogen of attachment form a 4-7 membered heterocycloalkyl ring; or
  (ii) two or three $R^c$ moieties where two $R^c$ moieties are adjacent to each other and together form —$O(CH_2)_{1-3}$O— unsubstituted or substituted with one or two fluoro groups, and the third $R^c$ moiety, when present, is —$C_{1-4}$alkyl, —$C_{1-4}$alkyl-OH, —$C_{1-4}$alkyl-CN, perfluoroalkyl, —OH, —$OC_{1-4}$alkyl, perfluoroalkoxy, —$S(O)_{0-2}C_{1-4}$alkyl, —$SCF_3$, —$SO_2CF_3$, —CHO, —$COC_{1-4}$alkyl, —$CO_2C_{1-4}$alkyl, —$CO_2H$, —$N(R^d)R^e$, —$SO_2NR^dR^e$, —$NR^dSO_2R^e$, —$C(O)NR^dR^e$, —$NO_2$, —CN, or halo,
    where $R^d$ and $R^e$ are each independently —H or —$C_{1-4}$alkyl;

$Ar^2$ is:
  (i) phenyl substituted with;
    one, two, or three $R^g$ moieties each at a meta or para position, and optionally with one or two additional $R^g$ moieties at an ortho position;
    where each $R^g$ moiety is independently halo, OH, —$C_{1-4}$alkyl, —$C_{1-4}$alkyl-OH, —$C_{1-4}$alkyl-CN, perfluoroalkyl, perfluoroalkoxy, —$OC_{1-4}$alkyl, —$OC_{1-4}$alkyl-(monocyclic cycloalkyl), —$S(O)_{0-2}C_{1-4}$alkyl, —$SCF_3$, —$SO_2CF_3$, —CHO, —$COC_{1-4}$alkyl, —$CO_2C_{1-4}$alkyl, —$CO_2H$, —$N(R^h)R^i$, —$SO_2NR^hR^k$, —$NR^hSO_2R^i$, —$C(O)NR^jR^k$, —$NO_2$, —CN; or a phenoxy, benzyl, phenethyl, or benzoyl group unsubstituted or substituted with —$C_{1-4}$alkyl, —$OC_{1-4}$alkyl, perfluoroalkyl, perfluoroalkoxy, —$NO_2$, —CN, or halo; or two adjacent $R^g$ moieties taken together form —$O(CH_2)_{1-2}$O— unsubstituted or substituted with one or two fluoro groups;
    where $R^h$ is H or —$C_{1-4}$alkyl;
    $R^i$ is —$C_{1-4}$alkyl or monoclic cycloalkyl group;
    or $R^h$ and $R^i$ taken together with the atoms to which they are attached form a monocyclic heterocycloalkyl ring;
    $R^j$ is H or —$C_{1-4}$alkyl; and
    $R^k$ is H, —$C_{1-4}$alkyl or monoyclic cycloalkyl group;
    or $R^j$ and $R^k$ taken together with the atoms to which they are attached form a monocyclic heterocycloalkyl ring; or
  (ii) a monocyclic heteroaryl group substituted with one, two, or three $R^g$ moieties; or
  (iii) a naphthyl or bicyclic heteroaryl group unsubstituted or substituted with one, two, or three $R^l$ moieties;

where each $R^l$ moiety is independently —$C_{1-4}$alkyl, —$OC_{1-4}$alkyl, perfluoroalkyl, perfluoroalkoxy, —$NO_2$, —CN, or halo;
or a pharmaceutically acceptable salt of said compound.

2. A compound as defined in claim 1, wherein $Ar^1$ is
  (i) phenyl optionally substituted with one or two $R^c$ moieties selected from halo, —$CF_3$, —CN, —$OCHF_2$, —$OCH_3$, —$OCF_3$, —$CF_3$, —$SCH_3$, —$SCF_3$, —$S(O)(O)CH_3$, imidazolyl, pyrrolidinyl, pyridyl, phenyl, thiophenyl, or two adjacent substituents together form —$O(CH_2)_{2-3}O$—, or —$OCF_2O$—;
  (ii) napthyl;
  (iii) thiophenyl optionally substituted with pyridinyl;
  (iv) thiazolyl;
  (v) benzothiophenyl; or
  (vi) isoxazolyl; and
$Ar^2$ is
  (i) phenyl optionally substituted with one, two, or three $R^g$ moieties each at a meta or para position, wherein each said $R^g$ moiety is independently chloro, fluoro, —$CF_3$, —$CH(OH)CH_3$, —OH, —$OCF_3$, —$OCH_3$, —$OCH_2CH_3$, —$OCH_2CF_3$, —$OCHF_2$, —$SCF_3$, —$SCH_2CH_3$, —$S(O)(O)N(CH_3)_2$, —$S(O)(O)NHC(CH_3)_3$, —$S(O)(O)$-thiomorpholin-4-yl, or two adjacent $R^g$ moieties together form —$OCH_2O$-unsubstituted or substituted with two fluoro atoms;
  (ii) 1-benzothiophen-2-yl optionally substituted at the 5- or 6-position with F, $CF_3$, methyl or trifluoromethoxy;
  (iii) benzo[d]isoxazol-6-yl optionally substituted at the 3 position with —$CF_3$, —$CH_3$, or —$CH_2CF_3$;
  (iv) quinolin-6-yl; or
  (v) 5-acetyl-thiophen-2-yl;
or a pharmaceutically acceptable salt of said compound.

3. A compound as defined in claim 1, wherein $Ar^1$ is
  (i) phenyl optionally substituted with one or two $R^c$ moieties selected from halo, —$CF_3$, —CN, —$SCH_3$, —$SCF_3$, —$S(O)(O)CH_3$, or two adjacent substituents together form —$OCF_2O$—; or
  (ii) napthyl; and
$Ar^2$ is
  (i) phenyl optionally substituted with one, two, or three $R^g$ moieties each at a meta or para position, wherein each said $R^g$ moiety is independently chloro, fluoro, —$CF_3$, —$OCF_3$, —$OCH_2CH_3$, —$OCH_2CF_3$, —$OCHF_2$, —$SCF_3$, —$SCH_2CH_3$, —$S(O)(O)N(CH_3)_2$, or two adjacent $R^g$ moieties together form —$OCF_2O$—;
  (ii) 1-benzothiophen-2-yl substituted at the 5 position with methyl or trifluoromethoxy; or
  (iii) 3-trifluoromethyl-benzo[d]isoxazol-6-yl;
or a pharmaceutically acceptable salt of said compound.

4. A compound as defined in claim 3, wherein $Ar^1$ is phenyl optionally substituted with one or two $R^c$ substitutents selected from halo, —$CF_3$, —CN, —$SCH_3$, —$SCF_3$, —$S(O)(O)CH_3$, or two adjacent substituents together form —$OCF_2O$—.

5. A compound as defined in claim 4, wherein $R^1$ is H.

6. A compound as defined in claim 1, wherein $Ar^1$ is a phenyl group, unsubstituted or substituted with one, two, or three $R^c$ moieties.

7. A compound as defined in claim 6, wherein each $R^c$ moiety is selected from halo, —$CF_3$, —CN, —$SCH_3$, —$SCF_3$, —$S(O)(O)CH_3$, or two adjacent substituents together form —$OCF_2O$—.

8. A compound as defined in claim 1, wherein $Ar^2$ is a phenyl substituted with one, two or three $R^g$ moieties each at a meta or para position.

9. A compound as defined in claim 8, wherein each said $R^g$ moiety is independently chloro, fluoro, —$CF_3$, —$OCF_3$, —$OCH_2CH_3$, —$OCH_2CF_3$, —$OCHF_2$, —$SCF_3$, —$SCH_2CH_3$, —$S(O)(O)N(CH_3)_2$, or two adjacent $R^g$ moieties together form —$OCF_2O$—.

10. A compound as defined in claim 9, wherein $R^1$ is H.

11. A compound as defined in claim 1, wherein $Ar^2$ is 1-benzothiophen-2-yl optionally substituted at the 5 position with methyl or trifluoromethoxy.

12. A compound as defined in claim 1, wherein $Ar^2$ is a thiophenyl, pyridinyl, pyrimidinyl, or pyrazolyl group, each substituted with one, two, or three $R^g$ moieties.

13. A compound as defined in claim 1, wherein $Ar^2$ is a naphthyl, benzoxadiazolyl, indolyl, benzothiophenyl, quinolinyl, or indazolyl, each unsubstituted or substituted with one, two, or three $R^g$ moieties.

14. A compound selected from the group consisting of:
- (1R)—$N^2$-{6-[3-Chloro-4-(trifluoromethyl)phenyl]pyrimidin-4-yl}-1-phenylethane-1,2-diamine;
- (1R)-{2-[6-(3-Chloro-4-trifluoromethyl-phenyl)-pyrimidin-4-ylamino]-1-phenyl-ethyl}-carbamic acid tert-butyl ester;
- (1S)—$N^2$-{6-[3-Chloro-4-(trifluoromethyl)phenyl]pyrimidin-4-yl}-1-phenylethane-1,2-diamine;
- (1R)—$N^2$-{6-[3-Fluoro-4-(trifluoromethyl)phenyl]pyrimidin-4-yl}-1-phenylethane-1,2-diamine;
- (1R)-1-Phenyl-$N^2$-{6-[4-(trifluoromethyl)phenyl]pyrimidin-4-yl}ethane-1,2-diamine;
- (1R)-1-Phenyl-$N^2$-{6-[4-(trifluoromethoxy)phenyl]pyrimidin-4-yl}ethane-1,2-diamine;
- (1R)—$N^2$-{6-[3-Chloro-4-(trifluoromethoxy)phenyl]pyrimidin-4-yl}-1-phenylethane-1,2-diamine;
- (1R)—$N^2$-{6-[3-Fluoro-4-(trifluoromethoxy)phenyl]pyrimidin-4-yl}-1-phenylethane-1,2-diamine;
- (1R)—$N^2$-[6-(5-Methyl-1-benzothiophen-2-yl)pyrimidin-4-yl]-1-phenylethane-1,2-diamine;
- (1R)—$N^2$-{6-[4-Ethoxy-3-(trifluoromethyl)phenyl]pyrimidin-4-yl}-1-phenylethane-1,2-diamine;
- (1R)-1-Phenyl-$N^2$-(6-{4-[(trifluoromethyl)sulfanyl]phenyl}pyrimidin-4-yl)ethane-1,2-diamine;
- (1R)—$N^2$-{6-[4-(Difluoromethoxy)-3,5-difluorophenyl]pyrimidin-4-yl}-1-phenylethane-1,2-diamine;
- (1R)-1-Phenyl-$N^2$-{6-[3-(trifluoromethyl)-1,2-benzisoxazol-6-yl]pyrimidin-4-yl}ethane-1,2-diamine;
- (1R)—$N^2$-[6-(4-Chlorophenyl)pyrimidin-4-yl]-1-phenylethane-1,2-diamine;
- (1R)—$N^2$-[6-(3-Chlorophenyl)pyrimidin-4-yl]-1-phenylethane-1,2-diamine;
- (1R)—$N^2$-[6-(3,4-Dichlorophenyl)pyrimidin-4-yl]-1-phenylethane-1,2-diamine;
- (1R)—$N^2$-{6-[4-Chloro-3-(trifluoromethyl)phenyl]pyrimidin-4-yl}-1-phenylethane-1,2-diamine;
- (1R)-1-Phenyl-$N^2$-{6-[3-(trifluoromethoxy)phenyl]pyrimidin-4-yl}ethane-1,2-diamine;
- (1R)—$N^2$-[6-(4-Ethoxyphenyl)pyrimidin-4-yl]-1-phenylethane-1,2-diamine;
- (1R)-1-Phenyl-$N^2$-{6-[4-(2,2,2-trifluoroethoxy)phenyl]pyrimidin-4-yl}ethane-1,2-diamine;
- (1R)—$N^2$-{6-[3-Fluoro-4-(2,2,2-trifluoroethoxy)phenyl]pyrimidin-4-yl}-1-phenylethane-1,2-diamine;
- (1R)—$N^2$-{6-[4-(Ethylsulfanyl)phenyl]pyrimidin-4-yl}-1-phenylethane-1,2-diamine;
- 4-(6-{[(2R)-2-Amino-2-phenylethyl]amino}pyrimidin-4-yl)-N,N-dimethylbenzenesulfonamide;
- (1R)—$N^2$-[6-(2,2-Difluoro-1,3-benzodioxol-5-yl)pyrimidin-4-yl]-1-phenylethane-1,2-diamine;
- (1R)-1-Phenyl-$N^2$-{6-[5-(trifluoromethoxy)-1-benzothiophen-2-yl]pyrimidin-4-yl}ethane-1,2-diamine;
- N-[(1R)-2-({6-[3-chloro-4-(trifluoromethyl)phenyl]pyrimidin-4-yl}amino)-1-phenylethyl]-2,2,2-trifluoroacetamide;
- (1R)—$N^2$-[6-(3-Chloro-4-trifluoromethyl-phenyl)-pyrimidin-4-yl]-1-(4-fluoro-phenyl)-ethane-1,2-diamine;
- (1S)—$N^2$-[6-(3-Chloro-4-trifluoromethyl-phenyl)-pyrimidin-4-yl]-1-(4-fluoro-phenyl)-ethane-1,2-diamine;
- (1S)—$N^2$-[6-(3-Chloro-4-trifluoromethyl-phenyl)-pyrimidin-4-yl]-1-(4-trifluoromethyl-phenyl)-ethane-1,2-diamine;
- (1R)—$N^2$-[6-(3-Chloro-4-trifluoromethyl-phenyl)-pyrimidin-4-yl]-1-(4-trifluoromethyl-phenyl)-ethane-1,2-diamine;
- (1S)—$N^2$-[6-(3-Chloro-4-trifluoromethyl-phenyl)-pyrimidin-4-yl]-1-(2,2-difluoro-benzo[1,3]dioxol-5-yl)-ethane-1,2-diamine;
- (1R)-[6-(3-Chloro-4-trifluoromethyl-phenyl)-pyrimidin-4-yl]-1-(2,2-difluoro-benzo[1,3]dioxol-5-yl)-ethane-1,2-diamine;
- (1S)-4-{1-Amino-2-[6-(3-chloro-4-trifluoromethyl-phenyl)-pyrimidin-4-ylamino]-ethyl}-benzonitrile;
- (1R)-4-{1-Amino-2-[6-(3-chloro-4-trifluoromethyl-phenyl)-pyrimidin-4-ylamino]-ethyl}-benzonitrile;
- $N^2$-[6-(3-Chloro-4-trifluoromethyl-phenyl)-pyrimidin-4-yl]-1-(2-fluoro-phenyl)-ethane-1,2-diamine;
- (1S)—$N^2$-[6-(3-Chloro-4-trifluoromethyl-phenyl)-pyrimidin-4-yl]-1-(3-fluoro-phenyl)-ethane-1,2-diamine;
- (1R)—$N^2$-[6-(3-Chloro-4-trifluoromethyl-phenyl)-pyrimidin-4-yl]-1-(3-fluoro-phenyl)-ethane-1,2-diamine;
- (1S)—$N^2$-1-(4-Chloro-phenyl)-[6-(3-chloro-4-trifluoromethyl-phenyl)-pyrimidin-4-yl]-ethane-1,2-diamine;
- (1R)—$N^2$-1-(4-Chloro-phenyl)-[6-(3-chloro-4-trifluoromethyl-phenyl)-pyrimidin-4-yl]-ethane-1,2-diamine;
- (1S)—$N^2$-[6-(3-Chloro-4-trifluoromethyl-phenyl)-pyrimidin-4-yl]-1-(3,4-difluoro-phenyl)-ethane-1,2-diamine;
- (1R)—$N^2$-[6-(3-Chloro-4-trifluoromethyl-phenyl)-pyrimidin-4-yl]-1-(3,4-difluoro-phenyl)-ethane-1,2-diamine;
- (1S)—$N^2$-[6-(3-Chloro-4-trifluoromethyl-phenyl)-pyrimidin-4-yl]-1-(3,4-dichloro-phenyl)-ethane-1,2-diamine;
- (1R)—$N^2$-[6-(3-Chloro-4-trifluoromethyl-phenyl)-pyrimidin-4-yl]-1-(3,4-dichloro-phenyl)-ethane-1,2-diamine;
- (1S)—$N^2$-1-(4-Chloro-3-fluoro-phenyl)-[6-(3-chloro-4-trifluoromethyl-phenyl)-pyrimidin-4-yl]-ethane-1,2-diamine;
- (1R)—$N^2$-1-(4-Chloro-3-fluoro-phenyl)-[6-(3-chloro-4-trifluoromethyl-phenyl)-pyrimidin-4-yl]-ethane-1,2-diamine;
- (1S)—$N^2$-1-(3-Chloro-4-fluoro-phenyl)-[6-(3-chloro-4-trifluoromethyl-phenyl)-pyrimidin-4-yl]-ethane-1,2-diamine;
- (1R)—$N^2$-1-(3-Chloro-4-fluoro-phenyl)-[6-(3-chloro-4-trifluoromethyl-phenyl)-pyrimidin-4-yl]-ethane-1,2-diamine;
- (1S)-3-{1-Amino-2-[6-(3-chloro-4-trifluoromethyl-phenyl)-pyrimidin-4-ylamino]-ethyl}-benzonitrile;
- (1R)-3-{1-Amino-2-[6-(3-chloro-4-trifluoromethyl-phenyl)-pyrimidin-4-ylamino]-ethyl}-benzonitrile;
- (1R)—$N^2$-1-(3-Chloro-4-fluoro-phenyl)-[6-(3-chloro-4-trifluoromethyl-phenyl)-pyrimidin-4-yl]-ethane-1,2-diamine;

(1R)—N²-[6-(3-Chloro-4-trifluoromethyl-phenyl)-pyrimidin-4-yl]-1-naphthalen-2-yl-ethane-1,2-diamine;
(1R)-4-{1-Amino-2-[6-(3-chloro-4-trifluoromethyl-phenyl)-pyrimidin-4-ylamino]-ethyl}-2-fluoro-benzonitrile;
(1R)—N²-[6-(3-Chloro-4-trifluoromethyl-phenyl)-pyrimidin-4-yl]-1-(3,4-dichloro-phenyl)-ethane-1,2-diamine;
(1R)—N²-[6-(3-Chloro-4-trifluoromethyl-phenyl)-pyrimidin-4-yl]-1-(4-methylsulfanyl-phenyl)-ethane-1,2-diamine;
(1R)-3-{1-Amino-2-[6-(3-chloro-4-trifluoromethyl-phenyl)-pyrimidin-4-ylamino]-ethyl}-benzonitrile;
(1R)—N²-[6-(3-Chloro-4-trifluoromethyl-phenyl)-pyrimidin-4-yl]-1-(2-methoxy-phenyl)-ethane-1,2-diamine;
(1S)-3-{1-Amino-2-[6-(3-chloro-4-trifluoromethyl-phenyl)-pyrimidin-4-ylamino]-ethyl}-benzonitrile;
(1S)—N²-1-(3-Chloro-4-fluoro-phenyl)-[6-(3-chloro-4-trifluoromethyl-phenyl)-pyrimidin-4-yl]-ethane-1,2-diamine;
(1S)—N²-[6-(3-Chloro-4-trifluoromethyl-phenyl)-pyrimidin-4-yl]-1-(3,4-dichloro-phenyl)-ethane-1,2-diamine;
(1S)—N²-1-(4-Chloro-3-fluoro-phenyl)-[6-(3-chloro-4-trifluoromethyl-phenyl)-pyrimidin-4-yl]-ethane-1,2-diamine;
(1R)—N²-[6-(3-Chloro-4-trifluoromethyl-phenyl)-pyrimidin-4-yl]-1-(4-trifluoromethylsulfanyl-phenyl)-ethane-1,2-diamine;
(1R)-5-{1-Amino-2-[6-(3-chloro-4-trifluoromethyl-phenyl)-pyrimidin-4-ylamino]-ethyl}-2-fluoro-benzonitrile;
(1R)—N²-[6-(3-Chloro-4-trifluoromethyl-phenyl)-pyrimidin-4-yl]-1-(4-methanesulfonyl-phenyl)-ethane-1,2-diamine;
(1R)—N²-1-(4-Fluoro-phenyl)-[6-(3-fluoro-4-trifluoromethoxy-phenyl)-pyrimidin-4-yl]-ethane-1,2-diamine;
(1R)—N²-1-(4-Fluoro-phenyl)-[6-(3-trifluoromethyl-benzo[d]isoxazol-6-yl)-pyrimidin-4-yl]-ethane-1,2-diamine;
(1R)-Phenyl-N²-(6-quinolin-6-yl-pyrimidin-4-yl)-ethane-1,2-diamine;
(1R)—N²-[6-(5-Fluoro-benzo[b]thiophen-2-yl)-pyrimidin-4-yl]-1-phenyl-ethane-1,2-diamine;
(1R)-Phenyl-N²-[6-(5-trifluoromethyl-benzo[b]thiophen-2-yl)-pyrimidin-4-yl]-ethane-1,2-diamine;
(1R)-{4-[6-(2-Amino-2-phenyl-ethylamino)-pyrimidin-4-yl]-2-fluoro-phenyl}-ethanol;
(1R)-Phenyl-N²-[6-(6-trifluoromethyl-benzo[b]thiophen-2-yl)-pyrimidin-4-yl]-ethane-1,2-diamine;
(1R)—N²-[6-(3-Methyl-benzo[d]isoxazol-6-yl)-pyrimidin-4-yl]-1-phenyl-ethane-1,2-diamine;
(1R)—N²-(6-Benzo[b]thiophen-2-yl-pyrimidin-4-yl)-1-phenyl-ethane-1,2-diamine;
(1R)-{5-[6-(2-Amino-2-phenyl-ethylamino)-pyrimidin-4-yl]-thiophen-2-yl}-ethanone;
(1R)—N²-[6-(3,4-Dimethoxy-phenyl)-pyrimidin-4-yl]-1-phenyl-ethane-1,2-diamine;
(1R)—N²-(6-Benzo[1,3]dioxol-5-yl-pyrimidin-4-yl)-1-phenyl-ethane-1,2-diamine;
(1R)-4-[6-(2-Amino-2-phenyl-ethylamino)-pyrimidin-4-yl]-phenol;
(1R)—N²-[6-(3-Pentafluoroethyl-benzo[d]isoxazol-6-yl)-pyrimidin-4-yl]-1-phenyl-ethane-1,2-diamine;
(1R)—N²-[6-(3,4-Dichloro-phenyl)-pyrimidin-4-yl]-1-phenyl-ethane-1,2-diamine;
(1R)—N²-[6-(4-Methoxy-phenyl)-pyrimidin-4-yl]-1-phenyl-ethane-1,2-diamine;
(1R)-4-[6-(2-Amino-2-phenyl-ethylamino)-pyrimidin-4-yl]-N-tert-butyl-benzenesulfonamide;
(1R)-1-Phenyl-N²-{6-[4-(thiomorpholine-4-sulfonyl)-phenyl]-pyrimidin-4-yl}-ethane-1,2-diamine;
(1R)—N²-[6-(3-Chloro-4-trifluoromethyl-phenyl)-pyrimidin-4-yl]-1-thiophen-3-yl-ethane-1,2-diamine;
(1R)—N²-[6-(3-Chloro-4-trifluoromethyl-phenyl)-pyrimidin-4-yl]-1-thiazol-2-yl-ethane-1,2-diamine;
(1R)-1-Benzo[b]thiophen-2-yl-N²-[6-(3-chloro-4-trifluoromethyl-phenyl)-pyrimidin-4-yl]-ethane-1,2-diamine;
(1R)-1-Benzo[b]thiophen-3-yl-N²-[6-(3-chloro-4-trifluoromethyl-phenyl)-pyrimidin-4-yl]-ethane-1,2-diamine;
(1R)—N²-[6-(3-Chloro-4-trifluoromethyl-phenyl)-pyrimidin-4-yl]-1-(3-fluoro-4-trifluoromethyl-phenyl)-ethane-1,2-diamine;
(1R)—N²-[6-(3-Chloro-4-trifluoromethyl-phenyl)-pyrimidin-4-yl]-1-(2,3-dihydro-benzo[1,4]dioxin-6-yl)-ethane-1,2-diamine;
(1R)—N²-[6-(3-Chloro-4-trifluoromethyl-phenyl)-pyrimidin-4-yl]-1-(4-imidazol-1-yl-phenyl)-ethane-1,2-diamine;
(1R)—N²-[6-(3-Chloro-4-trifluoromethyl-phenyl)-pyrimidin-4-yl]-1-(3-trifluoromethylsulfanyl-phenyl)-ethane-1,2-diamine;
(1R)—N²-[6-(3-Chloro-4-trifluoromethyl-phenyl)-pyrimidin-4-yl]-1-(3,4-dimethoxy-phenyl)-ethane-1,2-diamine;
(1R)-1-(3-Chloro-4-methoxy-phenyl)-N²-[6-(3-chloro-4-trifluoromethyl-phenyl)-pyrimidin-4-yl]-ethane-1,2-diamine;
(1R)—N²-[6-(3-Chloro-4-trifluoromethyl-phenyl)-pyrimidin-4-yl]-1-(3,4-dihydro-2H-benzo[b][1,4]dioxepin-7-yl)-ethane-1,2-diamine;
(1R)—N²-[6-(3-Chloro-4-trifluoromethyl-phenyl)-pyrimidin-4-yl]-1-(2-difluoromethoxy-phenyl)-ethane-1,2-diamine;
(1R)—N²-[6-(3-Chloro-4-trifluoromethyl-phenyl)-pyrimidin-4-yl]-1-(2-fluoro-5-trifluoromethyl-phenyl)-ethane-1,2-diamine;
(1R)—N²-[6-(3-Chloro-4-trifluoromethyl-phenyl)-pyrimidin-4-yl]-1-(4-pyrrolidin-1-yl-phenyl)-ethane-1,2-diamine;
(1R)—N²-[6-(3-Chloro-4-trifluoromethyl-phenyl)-pyrimidin-4-yl]-1-(3-phenyl-isoxazol-5-yl)-ethane-1,2-diamine;
(1R)—N²-[6-(3-Chloro-4-trifluoromethyl-phenyl)-pyrimidin-4-yl]-1-(4-pyridin-2-yl-thiophen-2-yl)-ethane-1,2-diamine;
(1R)—N²-[6-(3-Chloro-4-trifluoromethyl-phenyl)-pyrimidin-4-yl]-1-(4-pyridin-2-yl-phenyl)-ethane-1,2-diamine;
(1R)-1-Biphenyl-4-yl-N²-[6-(3-chloro-4-trifluoromethyl-phenyl)-pyrimidin-4-yl]-ethane-1,2-diamine;
(1R)—N²-[6-(3-Chloro-4-trifluoromethyl-phenyl)-pyrimidin-4-yl]-1-(3-trifluoromethyl-phenyl)-ethane-1,2-diamine;
(1R)—N²-[6-(3-Chloro-4-trifluoromethyl-phenyl)-pyrimidin-4-yl]-1-(2,6-difluoro-phenyl)-ethane-1,2-diamine;
(1R)—N²-[6-(3-Chloro-4-trifluoromethyl-phenyl)-pyrimidin-4-yl]-1-(4-thiophen-2-yl-phenyl)-ethane-1,2-diamine;

(1R)—$N^2$-[6-(3-Chloro-4-trifluoromethyl-phenyl)-pyrimidin-4-yl]-1-(3-trifluoromethoxy-phenyl)-ethane-1,2-diamine;

or a pharmaceutically acceptable salt of said compound.

15. A pharmaceutical composition comprising:
(a) a therapeutically effective amount of at least one compound of Formula (I):

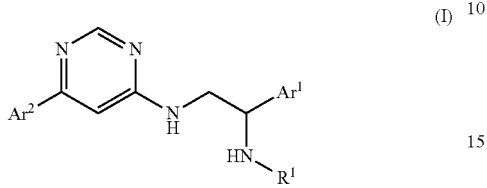

wherein
$R^1$ is —H, —C(O)CF$_3$, or —CO$_2$C(CH$_3$)$_3$;
Ar$^1$ is phenyl, napthyl, a 5 or 6 membered monocyclic heteroaryl group with carbon at the point of attachment, or a 9 or 10 membered bicyclic heteroaryl group with carbon at the point of attachment, each unsubstituted or substituted with;
(i) one, two, or three $R^c$ moieties,
where each $R^c$ moiety is independently —C$_{1-4}$alkyl, —C$_{1-4}$alkyl-OH, —C$_{1-4}$alkyl-CN, —OH, —OC$_{1-4}$alkyl, perfluoroalkyl, perfluoroalkoxy, —S(O)$_{0-2}$C$_{1-4}$alkyl, —SCF$_3$, —SO$_2$CF$_3$, —CHO, —COC$_{1-4}$alkyl, —CO$_2$C$_{1-4}$alkyl, —CO$_2$H, —N(R$^d$)R$^e$, —SO$_2$NR$^d$R$^e$, —NR$^d$SO$_2$R$^e$, —C(O)NR$^d$R$^e$, —NO$_2$, —CN, imidazolyl, phenyl, pyridyl, pyrrolidinyl, thiophenyl, or halo,
where $R^d$ and $R^e$ are each independently H or —C$_{1-4}$alkyl, or taken together $R^d$ and $R^e$ with the nitrogen of attachment form a 4-7 membered heterocycloalkyl ring; or
(ii) two or three $R^c$ moieties where two $R^c$ moieties are adjacent to each other and together form —O(CH$_2$)$_{1-3}$O— unsubstituted or substituted with one or two fluoro groups, and the third $R^c$ moiety, when present, is —C$_{1-4}$alkyl, —C$_{1-4}$alkyl-OH, —C$_{1-4}$alkyl-CN, perfluoroalkyl, —OH, —OC$_{1-4}$alkyl, perfluoroalkoxy, —S(O)$_{0-2}$C$_{1-4}$alkyl, —SCF$_3$, —SO$_2$CF$_3$, —CHO, —COC$_{1-4}$alkyl, —CO$_2$C$_{1-4}$alkyl, —CO$_2$H, —N(R$^d$)R$^e$, —SO$_2$NR$^d$R$^e$, —NR$^d$SO$_2$R$^e$, —C(O)NR$^d$R$^e$, —NO$_2$, —CN, or halo,
where $R^d$ and $R^e$ are each independently —H or —C$_{1-4}$alkyl;
Ar$^2$ is:
(i) phenyl substituted with;
one, two, or three $R^g$ moieties each at a meta or para position, and optionally with one or two additional $R^g$ moieties at an ortho position;
where each $R^g$ moiety is independently halo, OH, —C$_{1-4}$alkyl, —C$_{1-4}$alkyl-OH, —C$_{1-4}$alkyl-CN, perfluoroalkyl, perfluoroalkoxy, —OC$_{1-4}$alkyl, —OC$_{1-4}$alkyl-(monocyclic cycloalkyl), —S(O)$_{0-2}$C$_{1-4}$alkyl, —SCF$_3$, —SO$_2$CF$_3$, —CHO, —COC$_{1-4}$alkyl, —CO$_2$C$_{1-4}$alkyl, —CO$_2$H, —N(R$^h$)R$^i$, —SO$_2$NR$^j$R$^k$, —NR$^h$SO$_2$R$^i$, —C(O)NR$^j$R$^k$, —NO$_2$, —CN; or a phenoxy, benzyl, phenethyl, or benzoyl group unsubstituted or substituted with —C$_{1-4}$alkyl, —OC$_{1-4}$alkyl, perfluoroalkyl, perfluoroalkoxy, —NO$_2$, —CN, or halo; or two adjacent $R^g$ moieties taken together form —O(CH$_2$)$_{1-2}$O— unsubstituted or substituted with one or two fluoro groups;
where $R^h$ is H or —C$_{1-4}$alkyl;
$R^i$ is —C$_{1-4}$alkyl or monocyclic cycloalkyl group;
or $R^h$ and $R^i$ taken together with the atoms to which they are attached form a monocyclic heterocycloalkyl ring;
$R^j$ is H or —C$_{1-4}$alkyl; and
$R^k$ is H, —C$_{1-4}$alkyl or monocyclic cycloalkyl group;
or $R^j$ and $R^k$ taken together with the atoms to which they are attached form a monocyclic heterocycloalkyl ring; or
(ii) a monocyclic heteroaryl group substituted with one, two, or three $R^g$ moieties; or
(iii) a naphthyl or bicyclic heteroaryl group unsubstituted or substituted with one, two, or three $R^l$ moieties;
where each $R^l$ moiety is independently —C$_{1-4}$alkyl, —OC$_{1-4}$alkyl, perfluoroalkyl, perfluoroalkoxy, —NO$_2$, —CN, or halo;
and pharmaceutically acceptable salts of said compounds of Formula (I); and
(b) a pharmaceutically acceptable excipient.

16. A method of treating a subject suffering from or diagnosed with pain, comprising administering to the subject in need of such treatment a therapeutically effective amount of a pharmaceutical composition as defined in claim 15.

* * * * *